US008895543B2

(12) United States Patent
Scott et al.

(10) Patent No.: US 8,895,543 B2
(45) Date of Patent: *Nov. 25, 2014

(54) *VINCA* DERIVATIVES

(75) Inventors: Ian L. Scott, Woodinville, WA (US);
Jeffrey M. Ralph, Niskayuna, NY (US);
Matthew E. Voss, Nassau, NY (US)

(73) Assignee: Albany Molecular Research, Inc.,
Albany, NY (US)

( * ) Notice: Subject to any disclaimer, the term of this patent is extended or adjusted under 35 U.S.C. 154(b) by 1457 days.

This patent is subject to a terminal disclaimer.

(21) Appl. No.: 11/697,415

(22) Filed: Apr. 6, 2007

(65) Prior Publication Data

US 2007/0179171 A1    Aug. 2, 2007

Related U.S. Application Data

(63) Continuation of application No. 11/003,560, filed on Dec. 3, 2004, now Pat. No. 7,238,704.

(60) Provisional application No. 60/526,912, filed on Dec. 4, 2003.

(51) Int. Cl.
*A61K 31/33* (2006.01)
*A61K 31/395* (2006.01)
*C07D 519/04* (2006.01)

(52) U.S. Cl.
CPC .................................. *C07D 519/04* (2013.01)
USPC ........................................................ 514/183

(58) Field of Classification Search
None
See application file for complete search history.

(56) References Cited

U.S. PATENT DOCUMENTS

| | | | |
|---|---|---|---|
| 4,307,100 A | 12/1981 | Langlois et al. | |
| 4,347,249 A | 8/1982 | Potier et al. | |
| 4,388,305 A | 6/1983 | Trouet et al. | |
| 4,430,269 A | 2/1984 | Pearce | |
| 4,639,456 A | 1/1987 | Trouet et al. | |
| 4,737,586 A | 4/1988 | Potier et al. | |
| 4,769,453 A | 9/1988 | Potier et al. | |
| 5,047,528 A | 9/1991 | Kutney et al. | |
| 5,620,985 A | 4/1997 | Jacquesy et al. | |
| 6,127,377 A | 10/2000 | Duflos et al. | |
| RE37,449 E | 11/2001 | Kutney et al. | |
| 6,365,735 B1 | 4/2002 | Rool | |
| 7,235,564 B2 | 6/2007 | Scott et al. | |
| 7,238,704 B2 | 7/2007 | Scott et al. | |
| 7,745,619 B2 * | 6/2010 | Scott et al. | 540/470 |
| 2004/0186286 A1 | 9/2004 | Fukuyama et al. | |
| 2005/0176748 A1 | 8/2005 | Scott et al. | |
| 2007/0179170 A1* | 8/2007 | Scott et al. | 514/283 |
| 2007/0179171 A1 | 8/2007 | Scott et al. | |
| 2008/0051425 A1 | 2/2008 | Scott et al. | |
| 2008/0108644 A1 | 5/2008 | Scott et al. | |
| 2008/0119502 A1 | 5/2008 | Wolf et al. | |
| 2008/0125451 A1 | 5/2008 | Wolf et al. | |

FOREIGN PATENT DOCUMENTS

| | | |
|---|---|---|
| CA | 2458600 | 3/2003 |
| CN | 101108859 A | 1/2008 |
| EP | 0292463 A2 | 11/1988 |
| EP | 1 426 377 A1 | 6/2004 |
| FR | 2707988 A1 | 1/1995 |
| JP | 2003-064084 | 3/2003 |
| WO | 86/05491 A1 | 9/1986 |
| WO | 2005055943 A2 | 6/2005 |
| WO | WO 2005/055943 A2 | 6/2005 |
| WO | 2008/011805 A1 | 1/2008 |
| WO | 2008/033935 A2 | 3/2008 |
| WO | 2008033930 A2 | 3/2008 |

OTHER PUBLICATIONS

"Cancer definition", http://www.medterms.com/script/main/art.asp?articlekey=2580, accessed Nov. 27, 2007.*
Barthe et al., "Optimization of the Separation of *Vinca* Alkaloids by Nonaqueous Capillary Electrophoresis," Journal of Chromatography a 968:241-50 (2002).
International Search Report for International Patent Application No. PCT/US07/78281 (Sep. 3, 2008).
Sheng et al., "Synthesis and Biological Evaluation of C-12' Substituted Vinflunine Derivatives," Shanghai Hengrui Pharmaceutical Co. Ltd. Shanghai China, Poster Presented at 235th ACS National Meeting, New Orleans, LA (Apr. 6-10, 2008).
Berge et al., "Pharmaceutical Salts," *Journal of Pharmaceutical Sciences* 66(1):1-19 (1997).
Boyd, M.R., "Anticancer Drug Development Guide: Preclinical Screening, Clinical Trials, and Approval," Teicher, B. Ed., Humana Press, Totowa, New Jersey, pp. 23-42 (1997).
Fahy, J., "Modifications in the << upper >> or Velbenamine Part of the *Vinca* Alkaloids Have Major Implications for Tubulin Interacting Activities," *Current Pharmaceutical Design* 7:1181-1197 (2001).
Lobert et al., "*Vinca* Alkaloid-Induces Tubulin Spiral Formation Correlates with Cytotoxicity in the Leukemic L1210 Cell Line," *Biochemistry* 39:12053-12062 (2000).
Ram & Kumari, "Natural Products of Plant Origin as Anticancer Agents," *Drug News Perspect* 14(8):465-482 (2001).
Skehan et al., "New Colorimetric Cytotoxicity Assay for Anticancer-Drug Screening," *Journal of the National Cancer Institute* 82(13):1107-1112 (1990).
CAS(R) Registry No. 81600-06-8, Nov. 16, 1984.
CAS(R) Registry No. 123286-01-1; 123286-00-0, Oct. 20, 1999.
CAS(R) Registry No. 67699-41-6; 67699-40-5, Nov. 16, 1984.
Anhydrovinblastine, *Pioneer*, © IMSworld Publications Ltd (2000) (Update Date May 8, 2000).
Vinxaltine; S 12363, *Pioneer*, © IMSworld Publications Ltd (2000 (Update Date May 22, 1995).
Vinflunine; F 12158; L 0070, *Pioneer*, © IMSworld Publications Ltd (2000 (Update Date Apr. 19, 1999).
Napavin, *Pioneer*, © IMSworld Publications Ltd (2000 (Update Date Oct. 25, 1999).
Registry No. 166533-14-8, *SciFinder* (Feb. 28, 2002).
Registry No. 105801-71-6, *SciFinder* (Feb. 28, 2002).
Registry No. 105801-70-5, *SciFinder* (Feb. 28, 2002).
Registry No. 108893-99-8, *SciFinder* (Feb. 28, 2002).
Registry No. 108893-98-7, *SciFinder* (Feb. 28, 2002).
Registry No. 218128-76-8, *SciFinder* (Feb. 28, 2002).
Registry No. 54112-69-5, *SciFinder* (Feb. 28, 2002).
Registry No. 108893-97-6, *SciFinder* (Feb. 28, 2002).

(Continued)

*Primary Examiner* — Noble Jarrell
(74) *Attorney, Agent, or Firm* — LeClairRyan, a Professional Corporation

(57) ABSTRACT

The present invention relates to derivatives of vinca alkaloids. Pharmaceutical compositions containing these compounds as well as processes of preparation and treatment of various conditions are also disclosed.

50 Claims, No Drawings

(56) References Cited

OTHER PUBLICATIONS

Registry No. 108893-96-5, *SciFinder* (Feb. 28, 2002).
Registry No. 90012-98-9, *SciFinder* (Feb. 28, 2002).
Registry No. 90012-97-8, *SciFinder* (Feb. 28, 2002).
Neuss et al., "*Vinca* Alkaloids XXXIII [1]. Microbiological Conversions of Vincaleukoblastine (VLB, Vinblastine), an Antitumor Alkaloid from *Vinca* Rosea. Linn.," Helvetica Chimica Acta 57:1886-90 (1974).
Supplementary European Search Report for European Patent Application No. EP04813012 (May 14, 2009).
Kuehne et al., "Syntheses and Biological Evaluation of Vinblastine Congeners," Organic and Biomolecular Chemistry 1(2):2120-36 (2003).
Patani & Lavoie, "Bioisosterism: A Rational Approach in Drug Design," Chemical Review 96(8):3147-76 (1996).
Yamaguchi et al., "Identification of Novel Metabolites of Vinorelbine in Rat," Xenobiotica 28(3):281-91 (1998).
Merck Index, "Vindesine," 9982, 9986, 9987, and 9989.
Moncrief et al, "Structures of Leurocristine (Vincristine) and Vincaleukoblastine X-Ray Analysis of Leurocristine Methiodide," Journal of American Chemical Society 87(21):4963-64 (1965).
Bau et al., "Crystal Structure of Vinblastine," J. Chem. Soc. Perkin Trans. pp. 2079-82 (2000).
Mangeney et al., "A New Class of Antitumor Compounds: 5'-Nor and 5',6'-Seco Derivatives of Vinblastine-Type Alkaloids," J. Org. Chem. 44(22):3765-68 (1979).
Parish et al., "Circular Dichroism Studies of Bisindole Vinca Alkaloids," Tetrahedron 54(24):15739-58 (1998).

* cited by examiner

VINCA DERIVATIVES

The present invention is a continuation of U.S. patent application Ser. No. 11/003,560, filed Dec. 3, 2004, which claims benefit of U.S. Provisional Patent Application Ser. No. 60/526,912, filed Dec. 4, 2003, which are hereby incorporated by reference in their entirety.

FIELD OF THE INVENTION

The present invention relates to derivatives of the vinca alkaloids which are potent inhibitors of cellular mitosis and proliferation, as well as pharmaceutical compositions, preparation processes, and methods of use for treatment of various conditions.

BACKGROUND OF THE INVENTION

Cellular Proliferation and Cancer

The disruption of external or internal regulation of cellular growth can lead to uncontrolled cellular proliferation and in cancer, tumor formation. This loss of cellular growth control can occur at many levels and, indeed, does occur at multiple levels in most tumors. Under these circumstances, although tumor cells can no longer control their own proliferation, such cells still must use the same basic cellular machinery employed by normal cells to drive their growth and replication.

Mitosis and Spindle Formation

In a process known as mitosis, cancer cells, like all mammalian cells, multiply through replication and segregation of the original chromosomes. Following DNA replication in the S phase, the cells progress in the G2 phase. During the G2 phase, cells continue to increase in mass and prepare for mitosis. If chromosome damage is present in the G2 phase, the affected cell responds by activating the G2 phase checkpoint, which prevents progression into mitosis. In the absence of DNA damage or following repair of damage, the G2 phase cells then enter the M phase in which the identical pairs of chromosomes are separated and transported to opposite ends of the cell. The cell then undergoes division into two identical daughter cells.

In a process known as spindle formation, the cell utilizes the mitotic spindle apparatus to separate and pull apart the chromosomes. This apparatus, in part, consists of a network of microtubules that form during the first stage of mitosis. Microtubules are hollow tubes that are formed by the assembly of tubulin heterodimers from alpha- and beta-tubulin. The assembly of tubulin into microtubules is a dynamic process with tubulin molecules being constantly added and subtracted from each end.

Vinca Compounds as Inhibitors of Mitosis and Cellular Proliferation

In general, vinca compounds are known to be inhibitors of mitosis and cellular proliferation. In particular, the antiproliferative activity of the vinca alkaloid class of drugs has been shown to be due to their ability to bind tubulin. Assembly of tubulin into microtubules is essential for mitosis and the binding of the vincas to tubulin leads to cell cycle arrest in M phase and subsequently to apoptosis. For example, at low concentrations, these compounds interfere with the dynamics of microtubule formation. At higher concentrations, they cause microtubule disassembly, and at still higher concentrations, the formation of tubulin paracrystals.

Moreover, the anti-cancer activity of vinca alkaloids is generally believed to result from a disruption of microtubules resulting in mitotic arrest. However, cytotoxicity of vinca alkaloids also has been demonstrated in non-mitotic cells. Considering the role of microtubules in many cellular processes, the cytotoxic action of vinca alkaloids may involve contributions from inhibition of non-mitotic microtubule-dependent processes.

Cytotoxicity may also be a consequence of changes in membrane structure resulting from the partitioning of vinca alkaloids into the lipid bilayer. Studies with another tubulin binding compound, taxol, have shown that cell cycle arrest was not a precondition for apoptosis by agents of this type. Therefore, the anti-cancer activity of vinca alkaloids may be the result of disruption of a number of distinct microtubule-dependent and possibly microtubule-independent processes.

The assembly of tubulin into microtubules is a complex process involving dynamic instability (i.e. the switching between periods of slow growth and rapid shortening at both ends of the microtubule), and treadmilling (i.e. the addition of tubulin to one end of the microtubule occurring at the same rate as loss of tubulin from the other). Low concentrations of vinca alkaloids have been shown to bind to the ends of the microtubules and suppress both microtubule instability and treadmilling during the metaphase stage of mitosis. For example, vinca alkaloids have been shown to stabilize microtubule plus ends and destabilize microtubule minus ends. Although the spindle is retained under these conditions, there is frequently abnormal alignment of condensed chromosomes. At higher concentrations of vinca alkaloids, the spindle is not present and the chromosome distribution resembles that of prometaphase cells. At both low and high concentrations of vincas, mitotic arrest results from activation of metaphase-anaphase checkpoint. The molecular basis of this checkpoint is a negative signal sent from the kinetochore of chromosomes that are not attached to microtubules. This signal prevents the activation of pathways that result in the initiation of anaphase events.

Although there is a common binding site for the vinca alkaloids on tubulin, the members of this class do behave differently. The relative overall affinities for β-tubulin binding are vincristine>vinblastine>vinorelbine>vinflunine, but there is no significant difference in the affinity of all four drugs for tubulin heterodimers. The discrepancy has primarily been explained by differences in the affinities of vinca-bound heterodimers for spiral polymers and the binding of drug to unliganded polymers. For example, tubulin spirals induced by vinflunine are significantly smaller than those induced by vinorelbine.

In addition, vinca alkaloids also differ in their effects on microtubule dynamics. Vinflunine and vinorelbine suppress dynamic instability through: slowing the microtubule growth rate, increasing the mean duration of a growth event and reducing the duration of shortening. In contrast, vinblastine reduces the rate of shortening and increases the percentage of time the microtubules spend in the attenuated state. Vinblastine, vinorelbine, and vinflunine all suppress treadmilling, with vinblastine displaying the greatest potency.

In Vivo Properties

The vinca derivatives fall into the general class of cytotoxic anti-cancer agents and, as such, suffer from the same problem as all cytotoxics—i.e., toxicity. Vincristine and vinblastine are neurotoxic. Vinorelbine, which is structurally very similar to vinblastine and vincristine and is only slightly less potent, is less neurotoxic. This change in toxicity cannot be explained by examination of the binding affinity of these compounds for tubulin alone. It has been postulated to arise from an increase in sensitivity to changes in microtubule dynamics in tumor cells and, as described above, these compounds have been shown to have subtly different effects. It could also arise from changes in cellular uptake of the drug. Vinflunine is not very potent in vitro yet is active in vivo, and this has been attributed to its superior cellular uptake. There are also quite significant differences in the profile of efficacy of vinca alkaloids. Vincristine has found wide use in the treatment of hematologic malignancies including leukemias and lymphomas. It is also widely used in pediatric solid tumors and, in the past, in small cell lung cancer. Vinblastine is an important component of the combination regimen that is curative for testicular cancer. Vinorelbine is quite different and has found use mainly in breast cancer and non-small cell lung cancer.

There remains a need for novel vinca derivatives with improved pharmacological and therapeutic properties, improved processes for the preparations of such vinca derivative compounds, corresponding pharmaceutical compositions, and methods of use.

The present invention is directed to achieving these objectives.

SUMMARY OF THE INVENTION

The present invention relates to a compound of Formula (I) as follows:

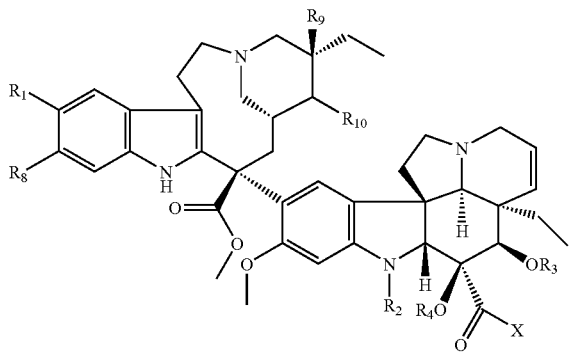

Formula 1 where:
$R_1$ is:
  alkyl;
  alkenyl;
  alkynyl;
  aryl;
  heterocyclyl;
  halogen;
  CN;
  CH(O);
  $COR_5$;
  $C(O)NHR_5$;
  $C(O)NR_5R_6$;
  $C(S)NH_2$;
  $C(O)NHNH_2$;
  $C(O)NR_5NH_2$;
  $C(O)NR_5NHR_6$;
  $C(O)NR_5NR_6R_7$;
  $C(O)NHNHR_5$;
  $C(O)NHNR_5R_6$;
  C(O)NHOH;
  $SO_2NHNH_2$;
  $SO_2NR_5NH_2$;
  $SO_2NR_5NHR_6$;
  $SO_2NR_5NR_6R_7$;
  $SO_2NHNHR_5$;
  $SO_2NHNR_5R_6$;
  $CO_2R_5$;
  $SR_5$;
  $SSR_5$;
  $SO_2NHR_5$;
  $SO_2NR_5R_6$;
  $B(OR_5)_2$;
  $CF_3$;
  SH;
  $SO_2NH_2$;
  $NH_2$;
  $NHR_5$;
  $NHSO_2R_5$;
  $NR_5R_6$;
  $NHCOR_5$;
  $NR_5COR_6$;
  $NR_5SO_2R_6$; or
$R_2$=alkyl or CH(O);
$R_3$=hydrogen, alkyl, or $C(O)R_5$;
$R_4$=hydrogen or $C(O)R_5$;
$R_5$, $R_6$ and $R_7$ each are independently alkyl, alkenyl, alkynyl, aryl, or heterocyclyl;
$R_8$=hydrogen, halogen, alkyl, alkenyl, alkynyl, aryl, heterocyclyl, acyl, or thioalkyl;
$R_9$=OH and $R_{10}$=H or $R_9$ and $R_{10}$ together form a bridging double bond.
$R_5$ and $R_6$ could form a ring as could $R_6$ and $R_7$.
X=$OR_5$, $NR_5R_6$, $NHNH_2$, $NHNHC(O)R_5$, OH; $NHR_5$; $NH_2$; or NHNHC(O)H;
$R_4$ and X may be linked together with intervening atoms to form a ring; $R_1$ and $R_8$ may be linked together; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted, with the proviso that when $R_8$=H, $R_9$=OH, and $R_{10}$=H, then $R_1 \neq$Br, I, OH, or OMe.

More preferably:
$R_9$=OH, $R_{10}$=H as in vincristine and vinblastine
$R_3$=Ac as in vincristine and vinblastine
$R_4$=H as in vincristine and vinblastine
X=Me as in vincristine and vinblastine
$R_1$=alkyl;
  alkenyl;
  alkynyl;
  aryl;
  heterocyclyl;
  halogen;
  CN;
  CH(O);
  $COR_5$;
  $C(O)NHR_5$
  $CO_2R_5$;
  $SR_5$;
  $SSR_5$;
  SH;
  $NH_2$;
  $NHR_5$;
  $NR_5R_6$;

Most preferably:
$R_1$=alkyl;
  alkenyl;
  alkynyl;
  halogen;
  CN;
  $SR_5$;
  $SSR_5$;

SH;
NH₂;
NHR₅;
NR₅R₆; where R₅ and R₆ form a ring

Another aspect of the present invention relates to a process for preparation of a derivative product compound of Formula (I) as follows:

Formula 1

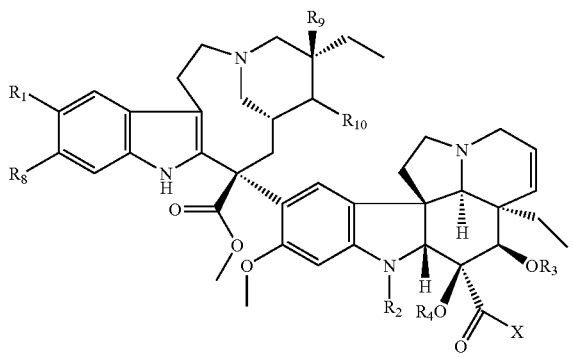

where:
R₁ is:
  alkyl;
  alkenyl;
  alkynyl;
  aryl;
  heterocyclyl;
  CN;
  CH(O);
  COR₅;
  C(O)NR₅R₆;
  C(O)NHR₅;
  C(O)NH₂;
  C(O)NHNH₂;
  C(O)NR₅NH₂;
  C(O)NR₅NHR₆;
  C(O)NR₅NR₆R₇;
  C(O)NHNHR₅;
  C(O)NHNR₅R₆;
  C(O)NHOH;
  SO₂NHNH₂;
  SO₂NR₅NH₂;
  SO₂NR₅NHR₆;
  SO₂NR₅NR₆R₇;
  SO₂NHNHR₅;
  SO₂NHNR₅R₆;
  CO₂R₅;
  SR₅;
  SSR₅;
  SO₂NHR₅;
  SO₂NR₅R₆;
  B(OR₅)₂;
  CF₃;
  SH;
  SO₂NH₂;
  NH₂;
  NHR₅;
  NHCOR₅;
  NHSO₂R₅;
  NR₅R₆;
  NHCOR₅;
  NR₅COR₆; or
  NR₅SO₂R₆;
R₂=alkyl or CH(O);
R₃=hydrogen, alkyl, or C(O)R₅;
R₄=hydrogen or C(O)R₅;
R₅, R₆ and R₇ each are independently alkyl, alkenyl, alkynyl, aryl, or heterocyclyl;
R₈=hydrogen, halogen, alkyl, alkenyl, alkynyl, aryl, heterocyclyl, acyl, or thioalkyl;
R₉=OH and R₁₀=H or R₉ and R₁₀ together form a bridging double bond;
R₅ and R₆ could form a ring or R₆ and R₇ could form a ring;
X=OR₅, NR₅R₆, NHNH₂, NHNHC(O)R₅, OH; NHR₅; NH₂; or NHNHC(O)H;
R₄ and X may be linked together with intervening atoms to form a ring; R₁ and R₈ may be linked together; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted, with the proviso, that when R₈=H, R₉=OH, and R₁₀=H, then R₁≠Br, I, OH, or OMe. The process also involves converting an intermediate compound of formula:

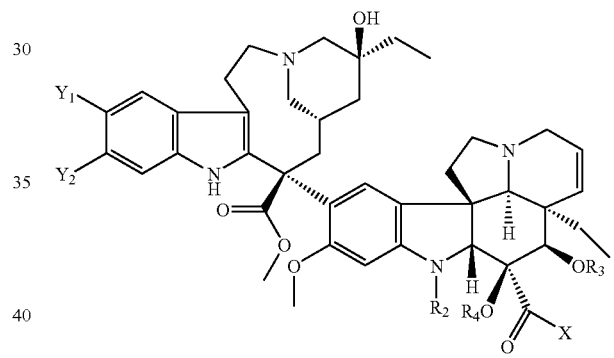

wherein Y₁, is a halogen and Y₂ is halogen or hydrogen, under conditions effective to produce the product compound of Formula (I).

Another aspect of the present invention relates to a process for preparation of a derivative product compound of Formula (I) as follows:

Formula 1

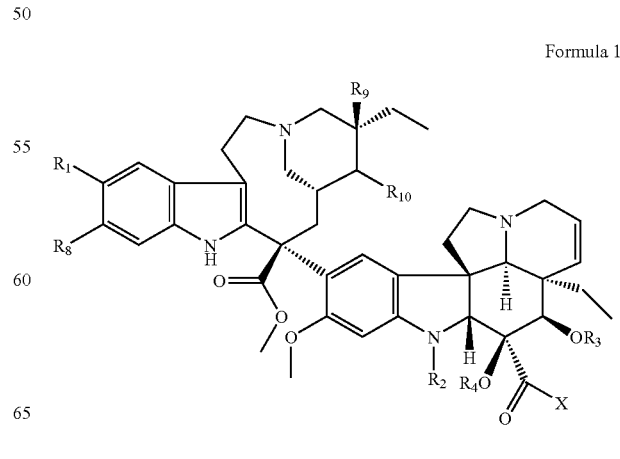

where:
R$_1$ is:
  halogen;
R$_2$=alkyl or CH(O);
R$_3$=hydrogen, alkyl, or C(O)R$_5$;
R$_4$=hydrogen or C(O)R$_5$;
R$_5$, R$_6$ and R$_7$ each are independently alkyl, alkenyl, alkynyl, aryl, or heterocyclyl;
R$_8$=hydrogen, halogen, alkyl, alkenyl, alkynyl, aryl, heterocyclyl, acyl, or thioalkyl;
R$_9$=OH and R$_{10}$=H or R$_9$ and R$_{10}$ together form a bridging double bond;
R$_5$ and R$_6$ could form a ring or R$_6$ and R$_7$ could form a ring;
X=OR$_5$, NR$_5$R$_6$, NHNH$_2$, NHNHC(O)R$_5$, OH; NHR$_5$; NH$_2$; or NHNHC(O)H;
R$_4$ and X may be linked together with intervening atoms to form a ring; R$_1$ and R$_8$ may be linked together; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted, with the proviso, that when R$_8$=H, R$_9$=OH, and R$_{10}$=H, then R$_1$≠Br, I, OH, or OMe. The process also involves halogenating a starting material of the formula:

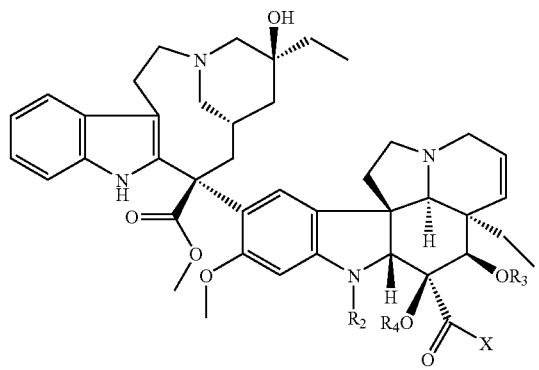

under conditions effective to form the derivative product compound.

The present invention also relates to a method for inhibiting cell proliferation in mammals, which comprises administering a therapeutically effective amount of the compound of Formula (I) to the mammal.

The present invention also relates to a method for treating a condition in mammals, which comprises administering a therapeutically effective amount of the compound of Formula (I) to the mammal. The condition can be bacterial infection, allergy, heart disease, AIDS, Human T-lymphotropic virus 1 infection, Human herpesvirus 3, Human herpesvirus 4, Human papillomavirus, diabetes mellitus, rheumatoid arthritis, Alzheimer's Disease, inflammation, arthritis, asthma, malaria, autoimmune disease, eczema, Lupus erythematosus, psoriasis, rheumatic diseases, Sjogren's syndrome, and viral infection.

The present invention also relates to a pharmaceutical composition of matter, which comprises the compound of Formula (I) and one or more pharmaceutical excipients.

DETAILED DESCRIPTION OF THE INVENTION

The present invention relates to novel derivatives of the vinca alkaloids, corresponding pharmaceutical compositions, preparation processes, and methods of use for treatment of various diseases.

In general, the novel compounds of the vinca family of compounds of the present invention, include derivatives of vincristine, vinblastine, anhydrovinblastine, and anhydrovincristine, etc. In accordance with the present invention, such derivative compounds are represented by the chemical structure of Formula (I) as shown herein.

In particular, the present invention relates to a compound of Formula (I) as follows:

Formula 1

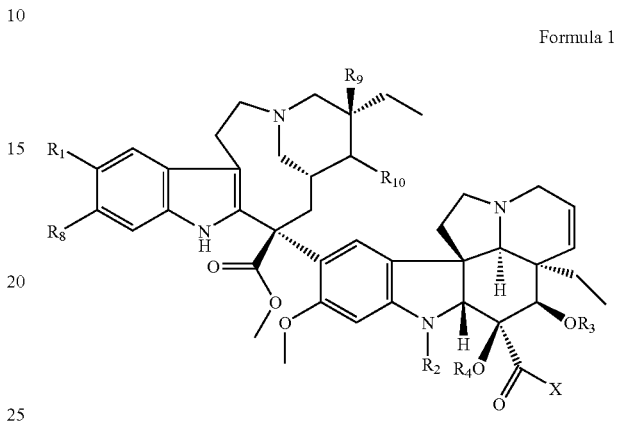

where:
R$_1$=alkyl;
  alkenyl;
  alkynyl;
  aryl;
  heterocyclyl;
  halogen;
  CN;
  CH(O);
  COR$_5$;
  C(O)NR$_5$R$_6$;
  C(O)NHR$_5$;
  C(O)NH$_2$;
  C(O)NHNH$_2$;
  C(O)NR$_5$NH$_2$;
  C(O)NR$_5$NHR$_6$;
  C(O)NR$_5$NR$_6$R$_7$;
  C(O)NHNHR$_5$;
  C(O)NHNR$_5$R$_6$;
  C(O)NHOH;
  SO$_2$NHNH$_2$;
  SO$_2$NR$_5$NH$_2$;
  SO$_2$NR$_5$NHR$_6$;
  SO$_2$NR$_5$NR$_6$R$_7$;
  SO$_2$NHNHR$_5$;
  SO$_2$NHNR$_5$R$_6$;
  CO$_2$R$_5$;
  SR$_5$;
  SSR$_5$;
  SO$_2$NHR$_5$;
  SO$_2$NR$_5$R$_6$;
  B(OR$_5$)$_2$;
  CF$_3$;
  SH;
  SO$_2$NH$_2$;
  NH$_2$;
  NHR$_5$;
  NHSO$_2$R$_5$;
  NR$_5$R$_6$;
  NHCOR$_5$;
  NR$_5$COR$_6$; or NR$_5$SO$_2$R$_6$;
R$_2$=alkyl or CH(O);
R$_3$=hydrogen, alkyl, or C(O)R$_5$;
R$_4$=hydrogen or C(O)R$_5$;
R$_5$, R$_6$ and R$_7$ each are independently alkyl, alkenyl, alkynyl, aryl, or heterocyclyl;
R$_8$=hydrogen, halogen, alkyl, alkenyl, alkynyl, aryl, heterocyclyl, acyl, or thioalkyl;
R$_9$=OH and R$_{10}$=H or R$_9$ and R$_{10}$ together form a bridging double bond;
R$_5$ and R$_6$ could form a ring or R$_6$ and R$_7$ could form a ring;
X=OR$_5$, NR$_5$R$_6$, NHNH$_2$, NHNHC(O)R$_5$, OH; NHR$_5$; NH$_2$; or NHNHC(O)H;
R$_4$ and X may be linked together with intervening atoms to form a ring; or a pharmaceutically acceptable salt thereof, wherein the alkyl and alkenyl groups may be branched, straight, unsubstituted, and/or substituted and wherein the aryl, alkynyl, and heterocyclyl groups are substituted or unsubstituted, with the proviso, that when R$_8$=H, R$_9$=OH, and R$_{10}$=H, then R$_1$≠Br, I, OH, or OMe.

In one embodiment, the present invention relates to a compound where R$_3$=acetyl.

In another embodiment, the present invention relates to a compound where R$_4$=hydrogen.

In another embodiment, the present invention relates to a compound where X=OMe.

In another embodiment, the present invention relates to a compound where R$_3$=acetyl, R$_4$=hydrogen, and X=OMe.

In another embodiment, the present invention relates to a compound where R$_2$=CH(O).

In another embodiment, the present invention relates to a compound where R$_2$=alkyl.

Representative examples of the compounds of Formula (I) are set forth in Table 1 below

TABLE 1

Compounds of Formula (I)

| Example Number | COMPOUND OF FORMULA (I) | NAME OF VINCA COMPOUND |
|---|---|---|
| 5 | | 12'-phenylvincristine |
| 6 | | 12'-phenylvinblastine |
| 7 | | 12'-(4-methoxyphenyl)vincristine |

TABLE 1-continued
Compounds of Formula (I)
| Example Number | COMPOUND OF FORMULA (I) | NAME OF VINCA COMPOUND |
|---|---|---|
| 8 | 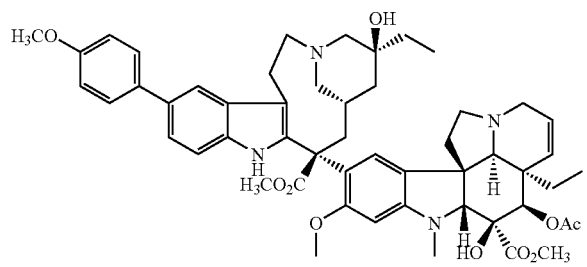 | 12'-(4-methoxyphenyl) vinblastine |
| 9 | 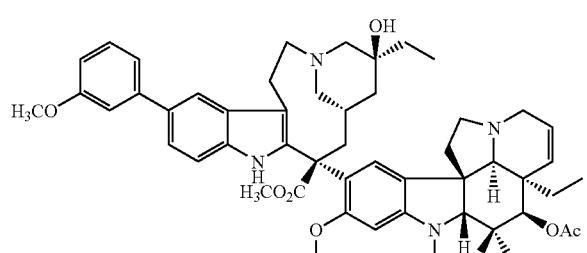 | 12'-(3-methoxyphenyl) vinblastine |
| 10 | 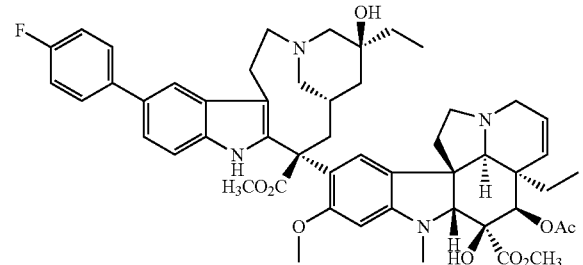 | 12'-(4-fluorophenyl) vinblastine |
| 11 | 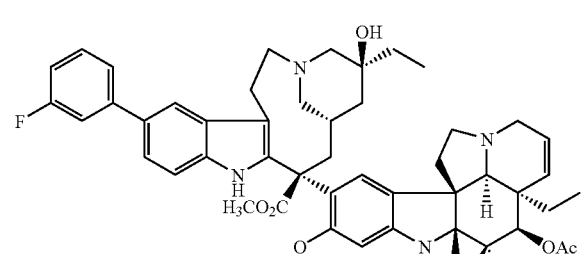 | 12'-(3-fluorophenyl) vinblastine |
| 12 | 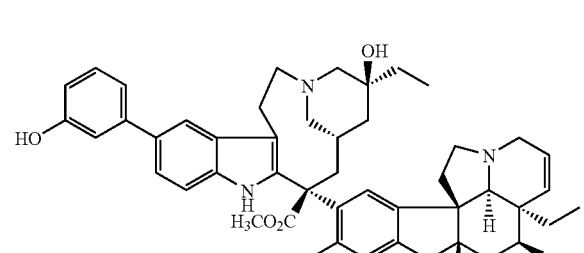 | 12'-(3-hydroxyphenyl) vinblastine |

TABLE 1-continued

Compounds of Formula (I)

| Example Number | COMPOUND OF FORMULA (I) | NAME OF VINCA COMPOUND |
|---|---|---|
| 13 | | 12'-(3-pyridyl)vinblastine |
| 14 | | 12'-(3-thienyl)vinblastine |
| 15 | | 12'-(2-thiazolyl)vinblastine |
| 16 | | 12'-(trimethylsilylethynyl)vinblastine |
| 17 | | 12'-ethynylvinblastine |

TABLE 1-continued
Compounds of Formula (I)
| Example Number | COMPOUND OF FORMULA (I) | NAME OF VINCA COMPOUND |
|---|---|---|
| 18 | 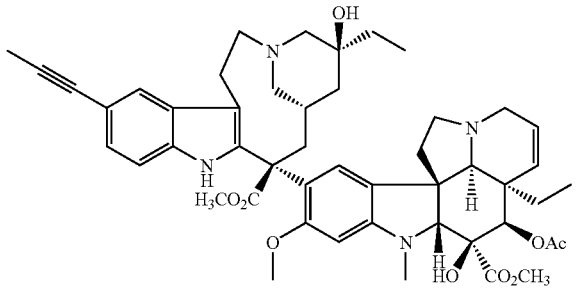 | 12'-propynylvinblastine |
| 19 | 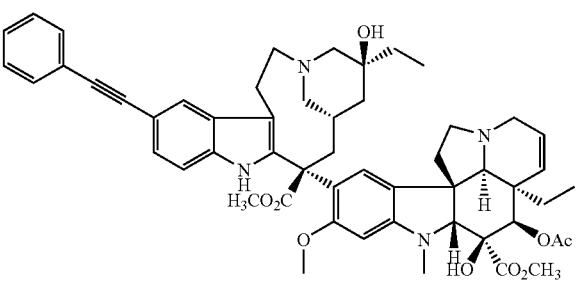 | 12'-(2-phenylethynyl)vinblastine |
| 20 | 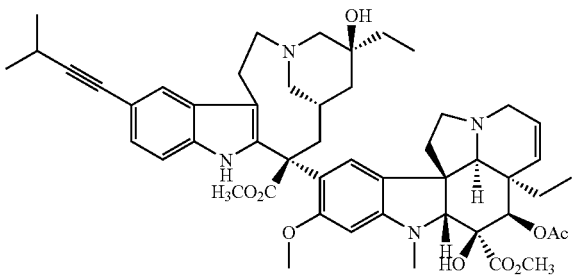 | 12'-(3-methylbutynyl)vinblastine |
| 21 | 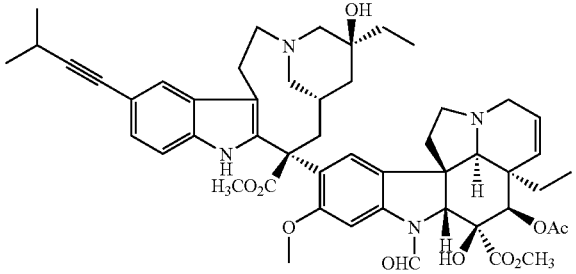 | 12'-(3-methylbutynyl)vincristine |
| 22 | 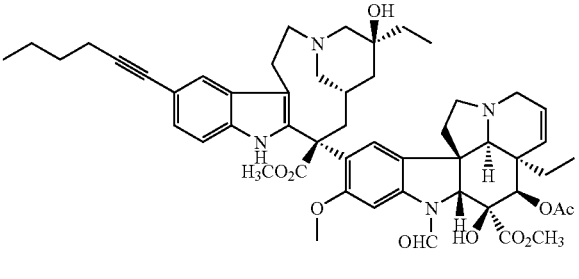 | 12'-hexynylvincristine |

TABLE 1-continued
Compounds of Formula (I)
| Example Number | COMPOUND OF FORMULA (I) | NAME OF VINCA COMPOUND |
|---|---|---|
| 23 | 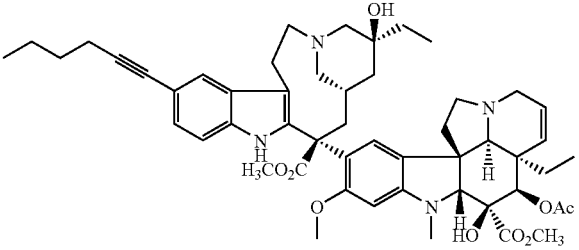 | 12'-hexynylvinblastine |
| 24 | 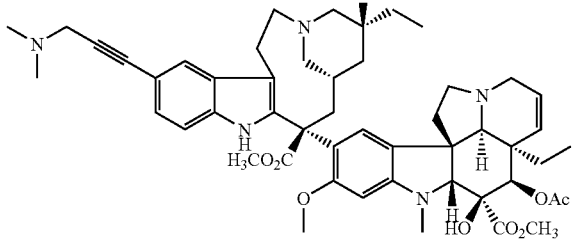 | 12'-(N,N-dimethylamino propynyl)vinblastine |
| 25 | 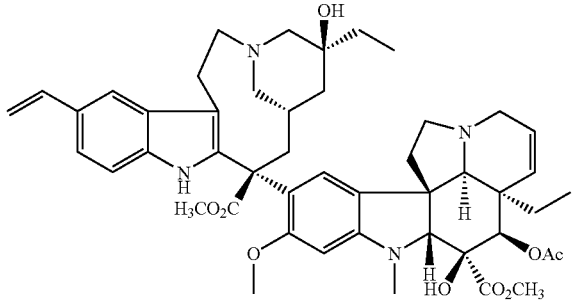 | 12'-vinylvinblastine |
| 26 | 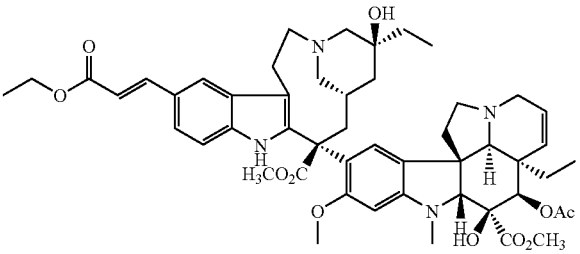 | 12'-(2-ethoxycarbonyl vinyl)vinblastine |
| 27 | 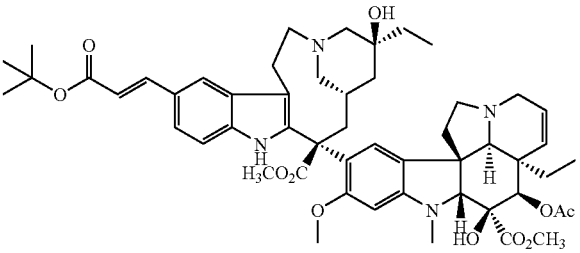 | 12'-(2-tert-butoxycarbonylvinyl)vinblastine |

TABLE 1-continued
Compounds of Formula (I)
| Example Number | COMPOUND OF FORMULA (I) | NAME OF VINCA COMPOUND |
|---|---|---|
| 28 | 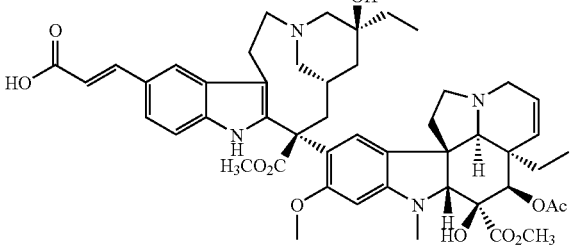 | 12'-(2-carboxylvinyl) vinblastine |
| 29 | 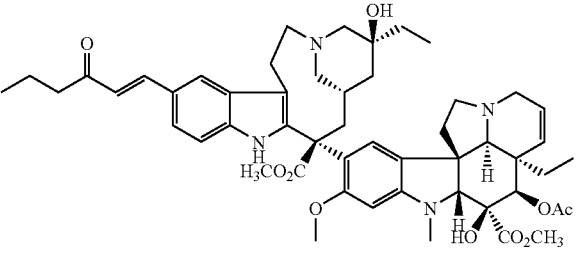 | 12'-(3-oxohex-1-enyl)vinblastine |
| 30 | 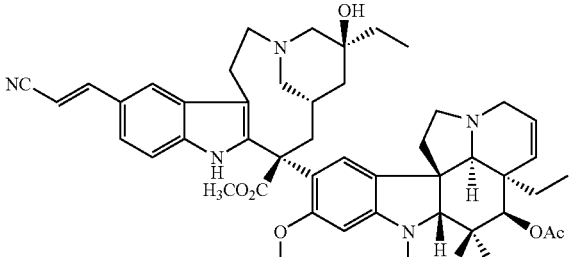 | 12'-(2-cyanovinyl) vinblastine |
| 31 | 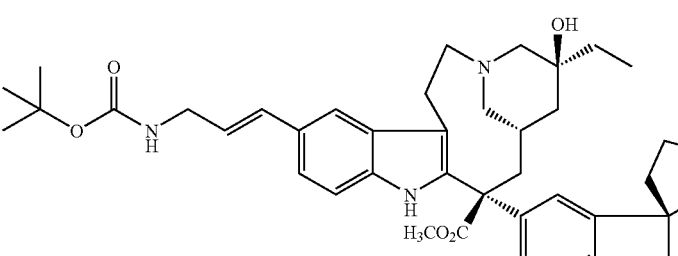 | 12'-(3-tert-butoxycarbonyl aminopropenyl) vinblastine |
| 32 | 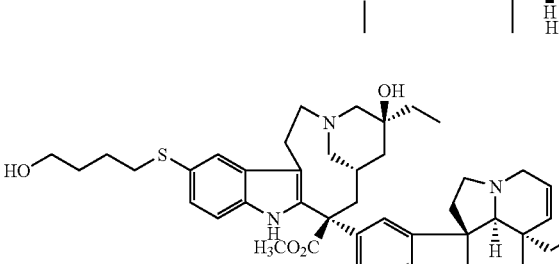 | 12'-(4-hydroxybutyl sulfanyl)vinblastine |

TABLE 1-continued

Compounds of Formula (I)

| Example Number | COMPOUND OF FORMULA (I) | NAME OF VINCA COMPOUND |
|---|---|---|
| 33 | | 12'-(4-hydroxypropyl sulfanyl)vinblastine |
| 34 | | 12'-(4-methanesulfonyl oxypropylsulfanyl) vinblastine |
| 35 | | 12'-(2-hydroxyethyl sulfanyl)vinblastine |
| 36 | | 12'-(4-methoxybenzyl sulfanyl)vinblastine |
| 37 | | 12'-(2-chlorobenzyl sulfanyl)vincristine |

TABLE 1-continued

Compounds of Formula (I)

| Example Number | COMPOUND OF FORMULA (I) | NAME OF VINCA COMPOUND |
|---|---|---|
| 38 | | 12'-(2-fluorobenzyl sulfanyl)vincristine |
| 39 | | 12'-(propylsulfanyl) vinblastine |
| 40 | | 12'-(ethylsulfanyl) vincristine |
| 41 | | 12'-(ethylsulfanyl) vinblastine |
| 42 | | 12'-(methylsulfanyl) vincristine |

TABLE 1-continued

Compounds of Formula (I)

| Example Number | COMPOUND OF FORMULA (I) | NAME OF VINCA COMPOUND |
|---|---|---|
| 43 | | 12'-(methylsulfanyl)vinblastine |
| 44 | | 12'-(tert-butoxycarbonyl methylsulfanyl)vinblastine |
| 45 | | 12'-(carboxymethyl sulfanyl)vinblastine |
| 46 | | 12'-(methylamino carbonylmethyl sulfanyl)vinblastine |
| 47 | | 12'-(methoxycarbonyl ethylsulfanyl)vincristine |

TABLE 1-continued

Compounds of Formula (I)

| Example Number | COMPOUND OF FORMULA (I) | NAME OF VINCA COMPOUND |
|---|---|---|
| 48 | | 12'-(2-(N,N-dimethyl amino)ethyl sulfanyl)vinblastine |
| 49 | | 12'-(3-(morpholin-4-yl)propylsulfanyl) vinblastine |
| 50 | | 12'-(3-(piperidin-1-yl) propylsulfanyl) vinblastine |
| 51 | | 12'-[2-Pyrrolidin-1-yl-ethylsulfanyl]vinblastine |
| 52 | | 12'-(2-(acetylamino) ethylsulfanyl) vinblastine |

TABLE 1-continued

Compounds of Formula (I)

| Example Number | COMPOUND OF FORMULA (I) | NAME OF VINCA COMPOUND |
|---|---|---|
| 53 | | 12'-thiovinblastine |
| 54 | | 12'-(3-hydroxyphenyl sulfanyl)vincristine |
| 55 | | 12'-(2-hydroxyphenyl sulfanyl)vinblastine |
| 56 | | 12'-(2-chlorophenyl sulfanyl)vincristine |
| 57 | | 12'-(methyldisulfanyl) vinblastine |

TABLE 1-continued
Compounds of Formula (I)
| Example Number | COMPOUND OF FORMULA (I) | NAME OF VINCA COMPOUND |
|---|---|---|
| 58 | 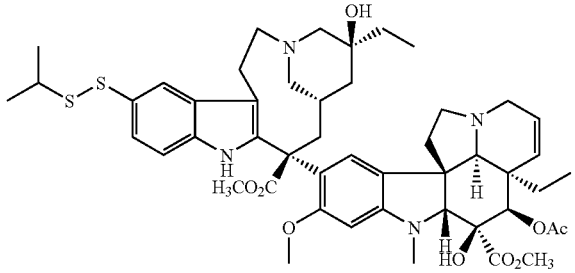 | 12'-(isopropyldisulfanyl)vinblastine |
| 59 | 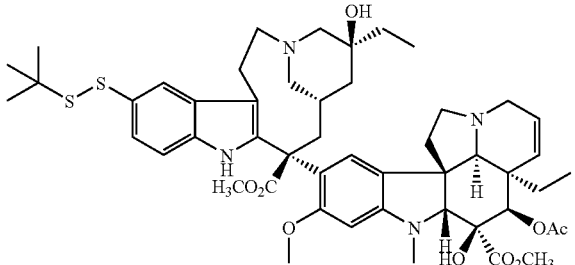 | 12'-(tert-butyldisulfanyl)vinblastine |
| 60 | 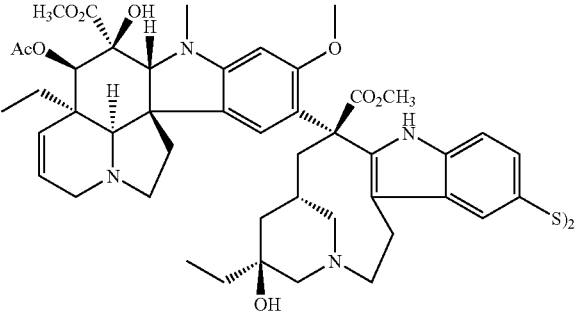 | di(12'-vinblastine) disulfide |
| 61 | 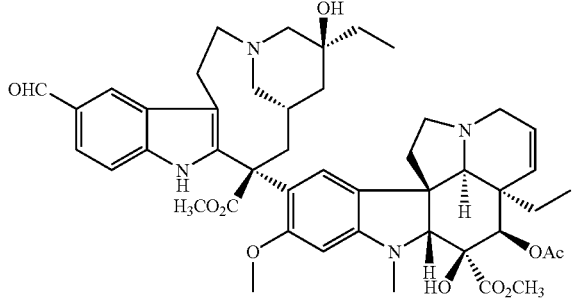 | 12'-formylvinblastine |
| 62 | 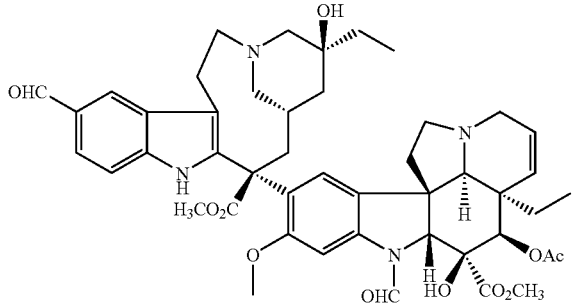 | 12'-formylvincristine |

TABLE 1-continued
Compounds of Formula (I)
| Example Number | COMPOUND OF FORMULA (I) | NAME OF VINCA COMPOUND |
|---|---|---|
| 63 | 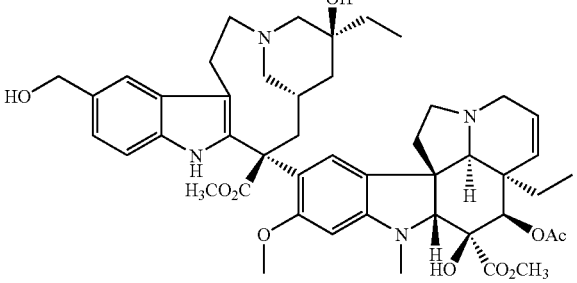 | 12'-(hydroxymethyl)vinblastine |
| 64 | 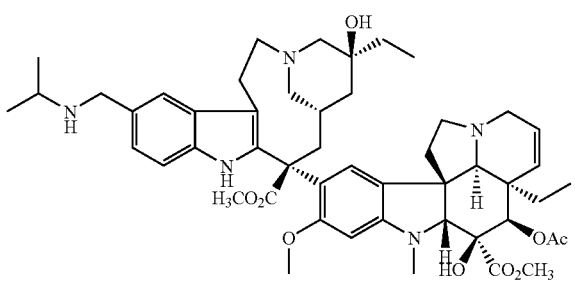 | 12'-(N-isopropylaminomethyl)vinblastine |
| 65 | 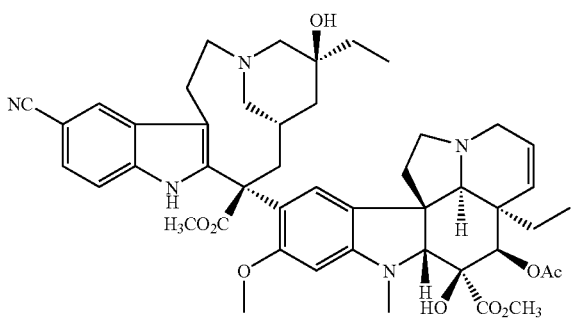 | 12'-cyanovinblastine |
| 66 | 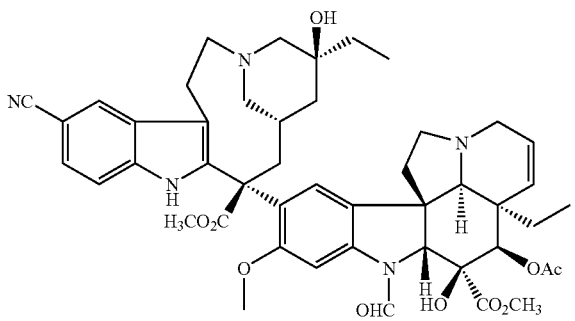 | 12'-cyanovincristine |
| 67 | 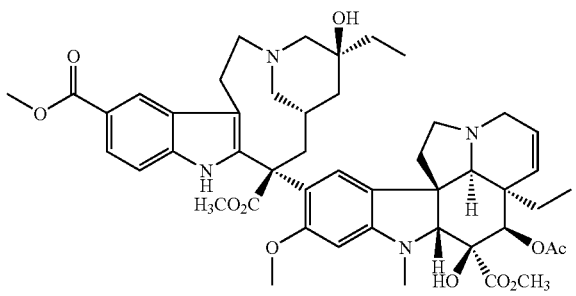 | 12'-(methycarbonyl)vinblastine |

TABLE 1-continued

Compounds of Formula (I)

| Example Number | COMPOUND OF FORMULA (I) | NAME OF VINCA COMPOUND |
|---|---|---|
| 68 | | 12'-(2,2,2-trichloroethyl carbonyl)vinblastine |
| 69 | | 12'-N-(methylamino carbonyl)vinblastine |
| 70 | | 12'-acetylvinblastine |
| 71 | | 12'-(3-methylbutanoyl) vincristine |
| 72 | | 12'-hexanoylvincristine |

TABLE 1-continued

Compounds of Formula (I)

| Example Number | COMPOUND OF FORMULA (I) | NAME OF VINCA COMPOUND |
|---|---|---|
| 73 | [structure] | 12'-(3-methylbutyl)vincristine |
| 74 | [structure] | 12'-hexylvincristine |
| 75 | [structure] | 12'-methylvinblastine |
| 76 | [structure] | 12'-methylvincristine |
| 77 | [structure] | 12'-ethylvinblastine |

TABLE 1-continued
Compounds of Formula (I)
| Example Number | COMPOUND OF FORMULA (I) | NAME OF VINCA COMPOUND |
|---|---|---|
| 78 | 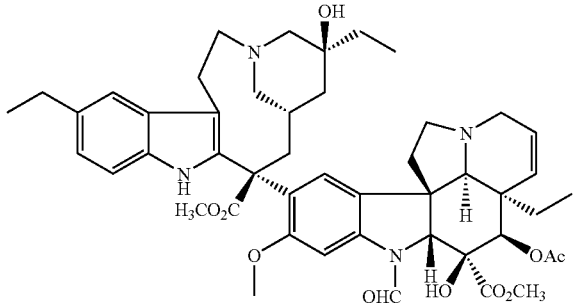 | 12'-ethylvincristine |
| 79 | 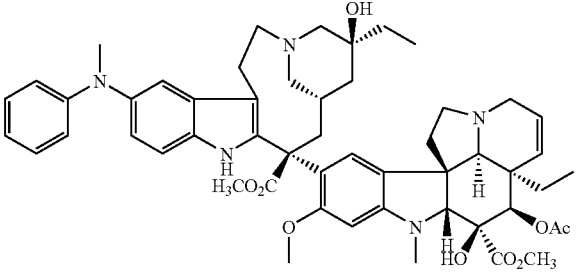 | 12'-(N-methyl-N-phenylamino)vinblastine |
| 80 | 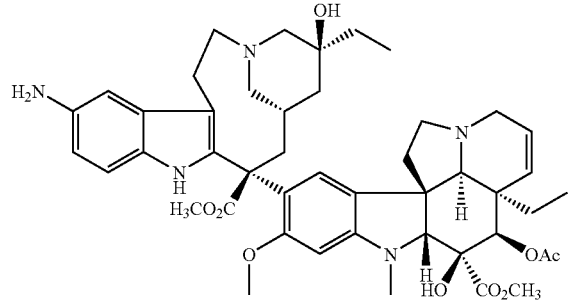 | 12'-aminovinblastine |
| 81 | 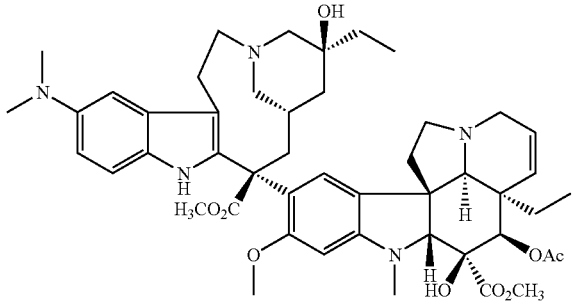 | 12'-(N,N-dimethylamino)vinblastine |
| 82 | 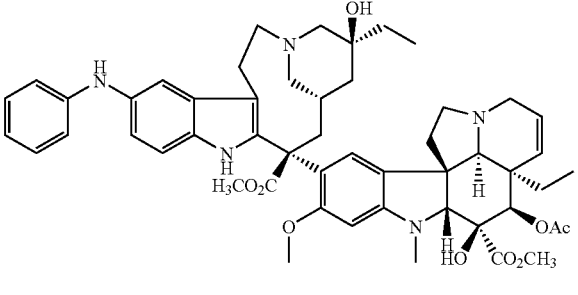 | 12'-(phenylamino)vinblastine |

TABLE 1-continued

Compounds of Formula (I)

| Example Number | COMPOUND OF FORMULA (I) | NAME OF VINCA COMPOUND |
|---|---|---|
| 83 | | 12'-(4-methoxyphenyl amino)vinblastine |
| 84 | | 12'-(4-trifluoromethyl phenylamino)vinblastine |
| 85 | | 12'-(1-piperidinyl) vinblastine |
| 86 | | 12'-(4-morpholino) vinblastine |
| 87 | | 12'-(pyrrolidin-1-yl) vinblastine |

TABLE 1-continued

| | Compounds of Formula (I) | |
|---|---|---|
| Example Number | COMPOUND OF FORMULA (I) | NAME OF VINCA COMPOUND |
| 88 | | 12'-(azetidin-1-yl)vinblastine |
| 89 | | 12'-(3-methylpyrazol-1-yl)vinblastine |
| 90 | | 12',13'-diiodovincristine |
| 91 | | 12',13'-diiodovinblastine |

TABLE 1-continued

Compounds of Formula (I)

| Example Number | COMPOUND OF FORMULA (I) | NAME OF VINCA COMPOUND |
|---|---|---|
| 92 | | 13'-iodo-12'-methyl vincristine |
| 93 | | 12',13'-dimethyl vincristine |
| 94 | | 13'-ethyl-12'-methyl vincristine |
| 95 | | 12',13'-diethylvincristine |

TABLE 1-continued

Compounds of Formula (I)

| Example Number | COMPOUND OF FORMULA (I) | NAME OF VINCA COMPOUND |
|---|---|---|
| 96 | | 13'-acetyl-12'-methyl vincristine |
| 97 | | 12'-bromoanhydro vinblastine |
| 98 | | 12'-iodoanhydro vinblastine |
| 99 | | 12'-bromoanhydro vincristine |

In yet another embodiment of the present invention, a complex can be formed which includes 2 structures of Formula (I) joined together at their $R_1$ groups, where each $R_1$ is —S—.

The synthetic reaction scheme for the preparation of compounds of Formula (I) is depicted below.

A synthetic scheme for preparing compounds of Formula (I) is shown in Scheme 1 below. A vinca alkaloid is treated with either N-bromosuccinimide or N-iodosuccinimide to introduce halogens in the 12' and 13'-positions. Pd-mediated coupling is then used to introduce other functionality at these position. This methodology can be used to introduce alkyl, alkenyl, alkynyl, aryl, heterocyclyl, acyl, cyano, amino, and formyl groups and to form sulphides. Each of these groups can then be subjected to further derivatization following standard methods of organic synthesis

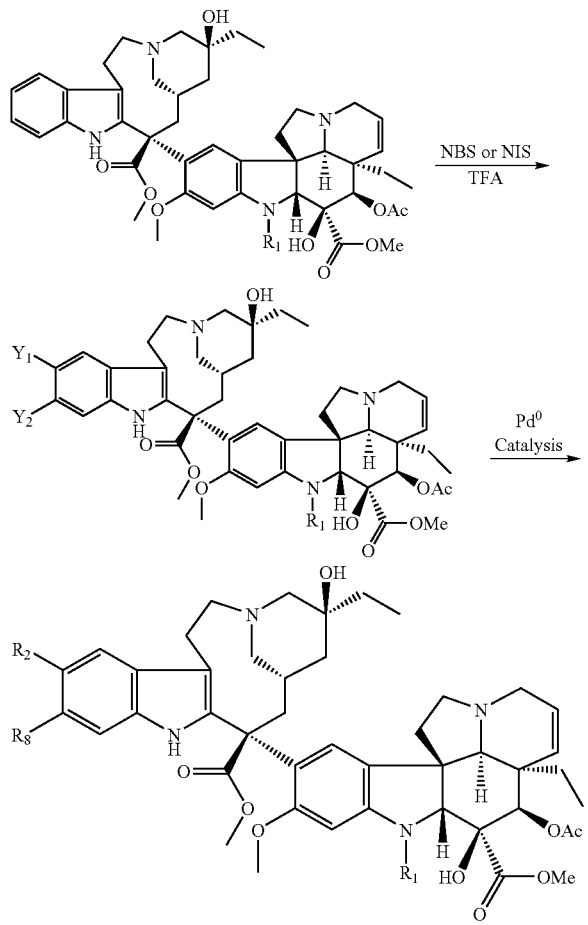

Y = Br, I
$R_2$ = Me, CHO
$R_1$, $R_8$ = previously defined list herein
NBS = N-Bromosuccinimide
NIS = N-Iodosuccinimide In practicing the above process, a variety of catalysts may be utilized, such as palladium chloride, palladium acetate, tris(dibenzylideneacetone)palladium(0), tetrakis(triphenylphosphine)palladium(0), dichlorobis(triphenylphosphine)palladium(II), benzylchlorobis(triphenylphosphine) palladium(II), or [1,1'-bis(diphenylphosphino)ferrocene]dichloropalladium(II).

Based on the results obtained in the standard pharmacological test procedures described below, the compounds of the present invention are useful in inhibiting cellular proliferation in a mammal by administering to such mammal an effective amount of compound(s) of the present invention.

In particular, such vinca compound derivatives are useful as antineoplastic agents. More particularly, the compounds of the present invention are useful for inhibiting the growth of neoplastic cells, causing cell death of neoplastic cells, and eradicating neoplastic cells. The compounds of the present invention are, therefore, useful for treating solid tumors, (e.g., sarcomas), carcinomas, (e.g., astrocytomas), lymphomas, (e.g., adult T-cell lymphoma), different cancer disease types, (e.g., prostate cancer, breast cancer, small cell lung cancer, ovarian cancer), Hodgkin's Disease, and other neoplastic disease states (e.g., leukemias, particularly adult T-cell leukemias).

Since vinca compounds are known to be tubulin inhibitors, the compounds of the present invention would also be expected to be useful in treating the following conditions: bacterial infection; allergy; heart disease; AIDS; Human T-lymphotropic virus 1 infection; Human herpesvirus 3; Human herpesvirus 4; Human papillomavirus; diabetes mellitus; rheumatoid arthritis; Alzheimer's Disease; inflammation; arthritis; asthma; malaria; autoimmune disease; eczema; Lupus erythematosus; psoriasis; rheumatic diseases; Sjogren's syndrome; and viral infection.

The vinca derivative compounds of the present invention can be administered alone, as indicated above, or utilized as biologically active components in pharmaceutical compositions with suitable pharmaceutically acceptable carriers, adjuvants and/or excipients.

In accordance with the present invention, the compounds and/or corresponding compositions can be introduced via different administration routes, which include orally, parenterally, intravenously, intraperitoneally, by intranasal instillation, or by application to mucous membranes, such as, that of the nose, throat, and bronchial tubes.

The active compounds of the present invention may be orally administered, for example, with an inert diluent, or with an assimilable edible carrier, or they may be enclosed in hard or soft shell capsules, or they may be compressed into tablets.

The quantity of the compound administered will vary depending on the patient and the mode of administration and can be any effective amount. The quantity of the compound administered may vary over a wide range to provide in a unit dosage an effective amount of from about 0.01 to 20 mg/kg of body weight of the patient per day to achieve the desired effect. The amount of active compound in such therapeutically useful compositions is such that a suitable dosage will be obtained. Preferred compositions according to the present invention are prepared so that an oral dosage unit contains between about 1 and 250 mg of active compound.

For example, with oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both.

These active compounds and/or pharmaceutical compositions may also be administered parenterally. Solutions of these active compounds and/or compositions can be prepared in water. Dispersions can also be prepared in glycerol, liquid polyethylene glycols, and mixtures thereof in oils.

Illustrative oils are those of animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the pharmaceutical form of the present invention must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds and/or pharmaceutical compositions of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Some of the compounds of the present invention can be in the form of pharmaceutically acceptable acid-addition and/or base salts. All of these forms of salts are within the scope of the present invention.

Pharmaceutically acceptable acid addition salts of the compounds of the present invention include salts derived from nontoxic inorganic acids, such as hydrochloric acid, nitric acid, phosphoric acid, sulfuric acid, hydrobromic acid, hydroiodic acid, hydrofluoric acid, phosphorous acid, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety).

The acid addition salts of said basic compounds are prepared by contacting the free base forms with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N-dibenzylethylenediamine, chloroprocaine, choline, diethanolamine, dicyclohexylamine, ethylenedianline, N-methylglucamine, and procaine (see, for example, Berge S. M. et al., "Pharmaceutical Salts," *Journal of Pharmaceutical Science*, 66:1-19 (1997), which is hereby incorporated by reference in its entirety).

The base addition salts of the acidic compounds are prepared by contacting the free acid form with a sufficient amount of the desired base to produce the salt in the conventional mariner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The present invention can be used in conjunction with other know cancer treatments, including other chemotherapeutic agents and radiation.

EXAMPLES

The following examples are provided to illustrate embodiments of the present invention but are no means intended to limit its scope.

Spectroscopic analysis of products described in the experimental procedures below were performed with conventional or standard scientific instrumentation known in the art. Proton NMR spectra were obtained on a Bruker AC 300 spectrometer at 300 MHz or a Bruker 500 MHz spectrometer at 500 MHz and were referenced to tetramethylsilane as an internal standard. Mass spectra were obtained on either a Shimadzu QP-5000 or a PE Sciex API 150 Mass Spectrometer.

Example 1

Preparation of 12'-Bromovinblastine Trifluoroacetate

A solution of vinblastine sulfate (0.5 g, 0.55 mmol) in trifluoroacetic acid (50 mL) under nitrogen was stirred at room temperature for 20 min. The flask was wrapped with foil to keep the reaction mixture in the dark and a solution of N-bromosuccinimide (103 mg, 0.58 mmol) in trifluoroacetic acid (25 mL) was added dropwise. After stirring for 18 h, the reaction mixture was concentrated under reduced pressure, diluted with dichloromethane, and poured into ice water. The aqueous layer was washed 3× with dichloromethane. The pH of the mixture was adjusted to 11-12 with 3% $NH_3$ (aq). The organic layer was separated and the aqueous layer was extracted with dichloromethane (3×) and the combined organic layers were washed with water, dried ($Na_2SO_4$), and concentrated under reduced pressure. Purification by column chromatography (silica (deactivated by eluting with 10% triethylamine in hexane), EtOAc) gave a mixture of mono and dibromides (0.33 g, 65%). Purification by reversed phase chromatography (C18, acetonitrile/water, 0.05% trifluoroacetic acid) gave 12'-bromovinblastine as a trifluoroacetate (0.42 g, 69%). $^1$H NMR (300 MHz, $CDCl_3$) δ 8.09 (s, 1H), 7.62 (d, J=2 Hz, 1H), 7.21 (dd, J=9, 2 Hz, 1H), 6.97 (d, J=9 Hz, 1H), 6.52 (s, 1H), 6.10 (s, 1H), 5.85 (dd, J=9, 4 Hz, 1H), 5.46 (s, 1H), 5.30 (d, J=9 Hz, 1H), 3.89 (m, 2H), 3.80 (s, 6H), 3.73 (s, 1H), 3.65 (m, 1H), 3.63 (s, 3H), 3.50-2.90 (m, 6H), 2.85 (m, 3H), 2.71 (s, 3H), 2.62 (s, 1H), 2.53-2.38 (m, 2H), 2.36-2.10 (m, 2H), 2.11 (s, 3H), 1.90-1.70 (m, 3H), 1.54-1.25 (m, 7H), 0.89 (t, J=7 Hz, 3H), 0.77 (t, J=7 Hz, 3H); ESI MS m/z 889, 891 [M+H]$^+$.

Example 2

Preparation of 12'-Iodovinblastine

A solution of N-iodosuccinimide (254 mg, 1.13 mmol) in trifluoroacetic acid/methylene chloride (1:1, 16 mL) was cooled to approximately 0° C. in an ice-water jacketed addition funnel then added dropwise to vinblastine hydrogensulfate (1.08 g, 1.19 mmol) in trifluoroacetic acid/methylene chloride (1:1, 32 mL) at −15° C. The temperature was monitored by an internal thermometer and maintained at −15±3° C. during the course of the addition (45 min). After the addition was complete, the reaction mixture was stirred 10 min then poured carefully into a rapidly stirring mixture of 10% sodium sulfite/satd sodium hydrogencarbonate/chloroform (1:2:2, 200 mL). Solid sodium hydrogencarbonate was then added in small portions until gas evolution stopped. The solution was then extracted with chloroform (3×50 mL) and the combined organic extracts were washed with 10% sodium sulfite (50 mL) and brine (50 mL) and dried over magnesium sulfate. The solvent was remove in vacuo to provide 12'-iodovinblastine (1.19 g, quantitative) as a tan foam which was carried forward without further purification: $^1$H NMR (500 MHz, CD$_3$OD) δ 7.75 (d, J=1.1 Hz, 1H), 7.32 (dd, J=8.4, 1.4 Hz, 1H), 7.00 (d, J=8.5 Hz, 1H), 6.56 (s, 1H), 6.31 (s, 1H), 5.83 (dd, J=10.2, 3.9 Hz, 1H), 5.36 (s, 1H), 5.29 (d, J=10.2 Hz, 1H), 3.91-4.07 (m, 2H), 3.81 (s, 3H), 3.76 (s, 3H), 3.64 (s, 3H), 3.58 (s, 1H), 3.36 (d, J=14.3 Hz, 1H), 3.30 (m, 1H), 3.15-3.27 (m, 3H), 2.94 (dd, J=14.8, 4.0 Hz, 1H), 2.71-2.85 (m, 4H), 2.71 (s, 3H), 2.41-2.49 (m, 2H), 2.26 (dd, J=15.6 3.6 Hz, 1H), 2.07 (m, 1H), 2.02 (s, 3H), 1.87 (m, 1H), 1.66 (m, 1H), 1.50 (d, J=14.1 Hz, 1H), 1.41 (m, 2H), 1.32 (q, J=7.4 Hz, 2H), 0.90 (t, J=7.5 Hz, 3H), 0.81 (m, 1H), 0.75 (t, J=7.3 Hz, 3H); ESI MS m/z 937 [M+H]$^+$.

Example 3

Preparation of 12'-Bromovincristine

12'-Bromovincristine was prepared from vincristine following the procedure described in Example 1, yield (1.41 g, 72%). $^1$H NMR (500 MHz, DMSO-d$_6$) δ 11.16 (br s, 1H), 10.63 (br s, 1H), 9.38 (br s, 1H), 7.83 (d, J=Hz, 1H), 7.46 (s, 1H), 7.35 (d, J=9 Hz, 1H), 7.23 (dd, J=9, 1 Hz, 1H), 7.07 (s, 1H), 5.90 (dd, J=11, 6 Hz, 1H), 5.62 (d, J=10 Hz, 1H), 5.18 (br s, 1H), 5.04 (s, 1H), 4.60 (s, 1H), 4.40 (m, 1H), 4.10-3.32 (m), 3.88 (s, 3H), 3.67 (s, 3H), 3.55 (s, 3H), 3.27 (br d, J=15 Hz, 1H), 3.12 (m, 3H), 3.02 (m, 1H), 2.76 (m, 1H), 2.30 (m, 1H), 2.21 (m, 1H), 2.03 (s, 3H), 1.82 (m, 1H), 1.58-1.37 (m, 7H), 1.10 (m, 1H), 0.87 (t, J=7 Hz, 3H), 0.65 (t, J=7 Hz, 3H); ESI MS m/z 903, 905 [M+H]$^+$.

Example 4

Preparation of 12'-Iodovincristine

A solution of N-iodosuccinimide (160 mg, 0.711 mmol) in trifluoroacetic acid/methylene chloride (1:1, 20 mL) was cooled to approximately 0° C. in an ice-water jacketed addition funnel then added dropwise to vinblastine hydrogensulfate (725 mg, 0.785 mmol) in trifluoroacetic acid/methylene chloride (1:1, 30 mL) at −15° C. The temperature was monitored by an internal thermometer and maintained at −15±3° C. during the course of the addition (30 min). The reaction was >97% complete as judged by HPLC (C18, acetonitrile, H$_2$O, 0.5% trifluoroacetic acid). Additional N-iodosuccinimide (8.0 mg, 0.036 mmol) was added and stirred for 10 minutes. HPLC indicated no remaining starting material. The reaction mixture was treated with saturated aqueous sodium bicarbonate, and further neutralized with NaOH (3 N) until a pH of 8 was obtained. The solution was diluted with methylene chloride (150 mL). The organic layer was washed with water and brine then dried over Na$_2$SO$_4$. The solvent was removed in vacuo to provide 12'-iodovincristine (0.68 g, 91%) as a tan powder which was carried forward without further purification: $^1$H NMR (500 MHz, CD$_3$OD) δ 8.93 (s, 1H), 7.77 (d, J=1.0 Hz, 1H), 7.32 (dd, J=8.5, 1.5 Hz, 1H), 7.21 (s, 1H), 7.08 (d, J=8.5 Hz, 1H), 6.86 (s, 1H), 5.83 (dd, J=10.0, 5.0 Hz, 1H), 5.40 (d, J=10.0 Hz, 1H), 5.14 (s, 1H), 4.58 (s, 1H), 4.09-4.01 (m 2H), 3.90 (s, 3H), 3.68 (s, 3H), 3.62 (s, 3H), 3.39 (d, J=14.5 Hz, 1H), 3.35-3.22 (m, 4H), 3.04 (s, 1H), 3.01 (m, 1H), 2.88-2.78 (m, 4H), 2.62 (m, 1H), 2.47 (dd, J=14.5, 4.0 Hz, 1H), 2.32 (dd, J=14.5 4.0 Hz, 1H), 2.08 (m, 1H), 2.00 (s, 3H), 1.76 (m, 1H), 1.54-1.28 (m, 6H), 0.90 (t, J=7.5 Hz, 3H), 0.75 (t, J=7.0 Hz, 3H); ESI MS m/z 937 [M+H]$^+$.

Example 5

Preparation of 12'-Phenylvincristine

A mixture of 12'-bromovincristine (231 mg, 0.256 mmol), cesium carbonate (0.5 g, 1.5 mmol) and phenyl boronic acid (62.5 mg, 0.51 mmol) in 1,4-dioxane (10 mL) was deoxygenated with argon. [1,1'-bis(diphenylphosphino)ferrocene] dichloropalladium(II) (21 mg, 0.026 mmol) was added and the mixture again deoxygenated with an argon purge, then heated at 60° C. for 24 h. After cooling, the reaction mixture was filtered through a short silica column, washing with dichloromethane then EtOAc, and filtrate concentrated under reduced pressure. Purification of the residue by flash chromatography (silica, EtOAc, then 99:1 EtOAc/EtOH) gave 12'-phenylvincristine (185 mg, 80%). $^1$H NMR (300 MHz, CDCl$_3$) δ 9.44 (br s, 1H), 8.77 (s, 1H), 8.21 (s, 1H), 8.17 (br s, 1H), 7.71 (s, 1H), 7.63 (d, J=8 Hz, 2H), 7.47 (t, J=8 Hz, 1H), 7.43 (d, J=8 Hz, 1H), 7.35 (t, J=7 Hz, 1H), 7.25 (d, J=8 Hz, 1H), 6.96 (s, 1H), 6.80 (s, 1H), 5.83 (m, 1H), 5.42 (d, J=10 Hz, 1H), 5.24 (d, J=10 Hz, 1H), 4.75 (s, 1H), 4.55 (s, 1H), 4.10-3.60 (m, 2H), 3.90 (s, 1H), 3.89 (s, 3H), 3.79 (s, 1H), 3.73 (s, 3H), 3.68 (s, 3H), 3.46-3.10 (m, 6H), 2.93 (m, 2H), 2.80 (s, 1H), 2.62 (m, 1H), 2.35 (m, 2H), 2.07 (m, 4H), 1.82-1.55 (m, 3H), 1.50-1.16 (m, 6H), 0.89 (t, J=7 Hz, 6H); ESI m/z 901 [M+H]$^+$.

Example 6

Preparation of 12'-Phenylvinblastine

12'-Phenylvinblastine was prepared 12'-bromobinblastine and phenyl boronic acid following the procedure described in Example 5, yield (45 mg, 19%). $^1$H NMR (300 MHz, CDCl$_3$) δ 9.89 (s, 1H), 8.08 (s, 1H), 7.69 (s, 1H), 7.63 (d, J=8 Hz, 2H), 7.45 (d, J=7 Hz, 1H), 7.42 (t, J=8 Hz, 2H), 7.34 (t, J=7 Hz, 1H), 7.19 (d, J=8 Hz, 1H), 6.66 (s, 1H), 6.11 (s, 1H), 5.87 (dd, J=10, 4 Hz, 1H), 5.48 (s, 1H), 5.30 (d, J=10 Hz, 1H), 3.98 (t, J=13 Hz, 1H), 3.80 (s, 5H), 3.74 (s, 1H), 3.63 (s, 3H), 3.50-

3.10 (m, 6H), 2.90-2.75 (m, 2H), 2.72 (s, 3H), 2.72 (s, 1H), 2.53-2.37 (m, 2H), 2.36-2.10 (m, 2H), 2.11 (s, 3H), 1.90-1.55 (m, 3H), 1.55-1.18 (m, 5H), 2.11 (s, 3H), 0.90 (t, J=7 Hz, 3H), 0.85 (t, J=7 Hz, 3H); ESI MS m/z 887 [M+H]$^+$.

Example 7

Preparation of 12'-(4-Methoxyphenyl)vincristine Trifluoroacetate

The trifluoroacetate of 12'-(4-methoxyphenyl)vincristine was prepared from 12'-bromovincristine and 4-methoxyphenyl boronic acid following the procedure described in Example 5. Purification by reversed phase chromatography (C18, acetonitrile/water, 0.05% trifluoroacetic acid) gave 12'-(4-methoxyphenyl)vincristine trifluoroacetate (135 mg, 87%). $^1$H NMR (300 MHz, CDCl$_3$) δ 8.76 (s, 1H), 8.21 (s, 1H), 8.16 (br s, 1H), 7.80 (s, 1H), 7.53 (d, J=9 Hz, 2H), 7.44 (d, J=8 Hz, 1H), 7.19 (d, J=8 Hz, 1H), 6.99 (d, J=8 Hz, 2H), 6.85 (s, 1H), 5.91 (m, 1H), 5.56 (m, 1H), 5.19 (d, J=15 Hz, 1H), 4.83 (m, 1H), 4.59 (dd, J=15, 10 Hz, 1H), 4.10-3.60 (m, 4H), 3.93 (s, 3H), 3.86 (s, 3H), 3.79 (s, 3H), 3.75 (s, 3H), 3.70 (s, 1H), 3.60-3.00 (m, 8H), 3.11 (br s, 3H), 2.82 (m, 1H), 2.56 (m, 1H), 2.41 (m, 1H), 2.07 (s, 3H), 1.96 (m, 1H), 1.67 (m, 2H), 1.55 (q, J=7 Hz, 2H), 1.47-1.19 (m, 2H), 0.99 (t, J=7 Hz, 3H) 0.76 (m, 3H); ESI m/z 931 [M+H]$^+$.

Example 8

Preparation of 12'-(4-Methoxyphenyl)vinblastine

12'-(4-Methoxyphenyl)vinblastine was prepared from 12'-bromovinblastine and 4-methoxyphenyl boronic acid following the procedure described in Example 5 (39 mg, 26%). $^1$H NMR (300 MHz, CDCl$_3$) δ 8.76 (s, 1H), 8.12 (s, 1H), 7.55 (br s, 1H), 7.53 (d, J=9 Hz, 2H), 7.42 (dd, J=9, 2 Hz, 1H), 7.14 (d, J=9 Hz, 1H), 6.99 (d, J=9 Hz, 2H), 6.53 (s, 1H), 6.13 (s, 1H), 5.87 (dd, J=10, 5 Hz, 1H), 5.45 (d, J=10 Hz, 2H), 5.44 (s, 1H), 4.59 (m, 1H), 4.00 (m, 1H), 3.94 (s, 1H), 3.87 (s, 3H), 3.84 (s, 3H), 3.83 (s, 3H), 3.70 (s, 3H), 3.60-2.80 (m, 12H), 2.71 (s, 3H), 2.63-2.40 (m, 2H), 2.15 (m, 1H), 2.09 (s, 3H), 2.00-1.30 (m, 10H), 0.99 (t, J=7 Hz, 3H), 0.73 (t, J=7 Hz, 3H); ESI m/z 917 [M+H]$^+$.

Example 9

Preparation of 12'-(3-Methoxyphenyl)vinblastine Trifluoroacetate

To a solution of 12'-iodovinblastine (45 mg, 0.05 mmol) in dioxane (1 mL) was added 3-methoxyphenylboronic acid (15 mg, 0.1 mmol) and Cs$_2$CO$_3$ (78 mg, 0.24 mmol). The mixture was deoxygenated with an argon purge, and [1,1'-bis(diphenylphospino)ferrocene]dichloropalladium (5 mg, 0.006 mmol) was added. The resulting mixture was deoxygenated again and then heated to 60° C. for 4 h. The reaction mixture was cooled to room temperature, diluted with CH$_2$Cl$_2$, and filtered through diatomaceous earth. The filtrate was washed with water and brine, and then dried (MgSO$_4$). Purification by column chromatography (silica, 9:1 CH$_2$Cl$_2$/MeOH) followed by preparative TLC (silica, 7:3 EtOAc/MeOH) gave 12'-(3-methoxyphenyl)vinblastine (18.4 mg, 41%). This material was dissolved in CH$_2$Cl$_2$ (1 mL) and treated with a drop of trifluoroacetic acid. The solution was evaporated to give 12'-(3-methoxyphenyl)vinblastine trifluoroacetate (22 mg, quantitative): $^1$H NMR (300 MHz, CD$_3$OD) δ 9.55 (s, 1H), 7.61 (s, 1H), 7.32-7.19 (m, 3H), 7.09 (d, J=8.0 Hz, 1H), 7.04 (dd, J=2.2, 1.8 Hz, 1H), 6.76 (d, J=7.5, 1.8 Hz, 1H), 6.60 (s, 1H), 6.33 (s, 1H), 5.84 (dd, J=10.6, 4.3 Hz, 1H), 5.57 (d, J=10.4 Hz, 1H), 5.27 (s, 1H), 4.61-4.54 (m, 1H), 3.91-3.56 (m, 9H), 3.77 (s, 3H), 3.75 (s, 3H), 3.72 (s, 3H), 3.61 (s, 3H), 3.43-3.29 (m, 2H), 3.15-3.09 (m, 2H), 2.80 (dd, J=14.4, 6.0 Hz, 1H), 2.68 (s, 3H), 2.40 (dd, J=15.0, 4.7 Hz, 1H), 2.31-2.21 (m, 1H), 1.98-1.89 (m, 1H), 1.98 (s, 3H), 1.71-1.62 (m, 1H), 1.58-1.56 (m, 2H), 1.51-1.39 (m, 3H), 1.27-1.25 (m, 1H), 0.88 (t, J=7.4 Hz, 3H), 0.74 (t, J=7.2 Hz, 3H); ESI MS m/z 917 [M+H]$^+$.

Example 10

Preparation of 12'-(4-Fluorophenyl)vinblastine

12'-(4-Fluorophenyl)vinblastine was prepared from 12'-bromovinblastine and 4-fluorophenyl boronic acid following the procedure described in Example 5 (63 mg, 43%). $^1$H NMR (300 MHz, CDCl$_3$) δ 8.15 (s, 1H), 7.60-7.52 (m, 3H), 7.41 (dd, J=8, 1 Hz, 1H), 722-7.08 (m, 3H), 6.99 (d, J=8 Hz, 2H), 6.85 (s, 1H), 5.91 (m, 1H), 5.56 (m, 1H), 5.19 (d, J=15 Hz, 1H), 4.83 (m, 1H), 4.59 (d, J=15, 10 Hz, 1H), 4.10-3.60 (m, 3H), 3.93 (s, 3H), 3.86 (s, 3H), 3.79 (s, 3H), 3.75 (s, 3H), 3.70 (s, 1H), 3.60-3.00 (m, 8H), 3.11 (br s, 3H), 2.82 (m, 1H), 2.56 (m), 2.41 (m, 1H), 2.12 (m, 1H), 2.07 (s, 3H), 1.96 (m, 1H), 1.67 (m, 2H), 1.55 (q, J=7 Hz, 2H), 1.47-1.19 (m, 2H), 0.99 (t, J=7 Hz, 3H) 0.76 (m, 3H); ESI m/z 905 [M+H]$^+$.

Example 11

Preparation of 12'-(3-Fluorophenyl)vinblastine Trifluoroacetate

To a solution of 12'-iodovinblastine (45 mg, 0.05 mmol) in dioxane (1 mL) was added 3-fluorophenylboronic acid (14 mg, 0.1 mmol) and Cs$_2$CO$_3$ (80 mg, 0.25 mmol). The mixture was deoxygenated with an argon purge, and [1,1'-bis(diphenylphospino)ferrocene]dichloropalladium (5 mg, 0.006 mmol) was added. The resulting mixture was deoxygenated again and then heated to 60° C. for 4 h. The reaction mixture was cooled to room temperature, diluted with CH$_2$Cl$_2$ and filtered through diatomaceous earth. The filtrate was washed with water and brine, and then dried (MgSO$_4$). Purification by column chromatography (silica, 9:1 CH$_2$Cl$_2$/MeOH) followed by preparative TLC (silica gel, 7:3 EtOAc/MeOH) gave 12'-(3-fluorophenyl)vinblastine (9.1 mg, 20%). This material was dissolved in CH$_2$Cl$_2$ (1 mL) and treated with a drop of trifluoroacetic acid. The solution was evaporated to give 12'-(3-fluorophenyl)vinblastine trifluoroacetate (11 mg, 80%): $^1$H NMR (300 MHz, CD$_3$OD) δ 9.63 (s, 1H), 7.65 (s, 1H), 7.40-7.25 (m, 5H), 6.94-6.88 (m, 1H), 6.60 (s, 1H), 6.33 (s, 1H), 5.84 (dd, J=10.6, 4.1 Hz, 1H), 5.57 (d, J=10.3 Hz, 1H), 5.27 (s, 1H), 4.61-4.55 (m, 1H), 3.91-3.56 (m, 9H), 3.77 (s, 3H), 3.72 (s, 3H), 3.61 (s, 3H), 3.43-3.30 (m, 2H), 3.15-3.09 (m, 2H), 2.80 (dd, J=14.4, 6.3 Hz, 1H), 2.68 (s, 3H), 2.40 (dd, J=16.3, 4.9 Hz, 1H), 2.31-2.21 (m, 1H), 1.98-1.89 (m, 1H), 1.98 (s, 3H), 1.71-1.62 (m, 1H), 1.58-1.56 (m, 2H), 1.50-1.39 (m, 3H), 1.31-1.25 (m, 1H), 0.88 (t, J=7.3 Hz, 3H), 0.74 (t, J=7.1 Hz, 3H); ESI MS m/z 905 [M+H]$^+$.

Example 12

Preparation of 12'-(3-Hydroxyphenyl)vinblastine

To a solution of 12'-iodovinblastine (39 mg, 0.040 mmol) in dioxane (1 mL) was added 3-hydroxyphenylboronic acid (12 mg, 0.080 mmol) and Cs$_2$CO$_3$ (68 mg, 0.21 mmol). The mixture was deoxygenated with argon, and [1,1'-bis(diphenylphosphino)ferrocene]dichloropalladium(II) (4 mg, 0.0040 mmol) was added. The resulting mixture was deoxygenated with argon again and then heated at 70° C. for 6 h and 80° C. overnight. The reaction mixture was cooled to room temperature, diluted with $CH_2Cl_2$, and filtered through diatomaceous earth. The filtrate was washed with water and brine, and dried. After removal of the solvents, the residue was purified by column chromatography (silica, 9:1 $CH_2Cl_2$/MeOH) followed by preparative TLC (silica, 7:3 EtOAc/MeO) to give 12-(3-hydroxyphenyl)vinblastine (4.2 mg, 12%): $^1$H NMR (500 MHz, $CD_3OD$) δ 7.51 (s, 1H), 7.24 (dd, J=14.0, 2.5 Hz, 1H), 7.14-7.09 (m, 2H), 7.00-6.95 (m, 2H), 6.61 (dd, J=13.5, 7.5 Hz, 1H), 6.53 (s, 1H), 6.23 (s, 1H), 5.75 (dd, J=17.0, 7.0 Hz, 1H), 5.28 (s, 1H), 5.19 (d, J=16.5 Hz, 1H), 4.02-3.87 (m, 2H), 3.72-3.67 (m, 7H), 3.56-3.49 (m, 5H), 3.36-3.31 (m, 1H), 3.20-2.96 (m, 4H), 2.73-2.61 (m, 7H), 2.40-2.31 (m, 2H), 2.25-2.16 (m, 1H), 2.03-1.91 (m, 4H), 1.86-1.78 (m, 1H), 1.64-1.58 (m, 1H), 1.44-1.19 (m, 7H), 0.83-0.69 (m, 6H); ESI MS m/z 903 $[M+H]^+$.

Example 13

Preparation of 12'-(3-Pyridyl)vinblastine

12'-(3-Pyridyl)vinblastine was prepared from 12'-bromovinblastine and 3-pyridyl boronic acid following the procedure described in Example 5 (26 mg, 16%). $^1$H NMR (300 MHz, $CDCl_3$) δ 9.82 (s, 1H), 8.89 (d, J=1.5 Hz, 1H), 8.54 (dd, J=5, 1 Hz, 1H), 8.13 (s, 1H), 7.91 (dt, J=8, 2 Hz, 1H), 7.69 (s, 1H), 7.33-7.39 (m, 2H), 7.22 (d, J=8 Hz, 1H), 6.63 (s, 1H), 6.11 (s, 1H), 5.86 (dd, J=10, 4 Hz, 1H), 5.47 (s, 1H), 5.31 (d, J=10 Hz, 1H), 3.99 (t, J=4 Hz, 1H), 3.80 (s, 3H), 3.79 (s, 3H), 3.74 (s, 1H), 3.68-3.87 (m, 2H), 3.63 (s, 3H), 3.26-3.43 (m, 5H), 3.18 (br s, 1H), 3.14 (br s, 1H), 2.82 (br t, J=8 Hz, 1H), 2.71 (s, 3H), 2.68 (s, 1H), 2.42-2.48 (m, 2H), 2.29 (br d, J=12 Hz, 1H), 2.15-2.22 (m, 1H), 2.11 (s, 3H), 1.74-1.89 (m, 3H), 1.25-1.51 (m, 6H), 0.89 (t, J=7 Hz, 3H), 0.83 (t, J=7 Hz, 3H). ESI m/z 888 $[M+H]^+$.

Example 14

Preparation of 12'-(3-Thienyl)vinblastine

12'-(3-Thienyl)vinblastine was prepared from 12'-bromovinblastine and 3-thienyl boronic acid by following the procedure described in Example 5 and then converted to the free base by treatment with ammonium hydroxide (45 mg, 23%). $^1$H NMR (300 MHz, $CDCl_3$) δ 9.87 (s, 1H), 8.07 (s, 1H), 7.68 (s, 1H), 7.42 (m, 4H), 7.45 (d, J=7 Hz, 1H), 7.14 (d, J=8 Hz, 1H), 6.70 (br s, 1H), 6.11 (s, 1H), 5.87 (dd, J=10, 4 Hz, 1H), 5.47 (s, 1H), 5.30 (obs d, J=10 Hz, 1H), 5.30 (s, 1H), 4.00-3.85 (m, 1H), 3.80 (s, 6H), 3.74 (s, 1H), 3.63 (s, 3H), 3.50-3.10 (m, 6H), 2.90-2.75 (m, 2H), 2.72 (s, 3H), 2.68 (s, 1H), 2.53-2.37 (m, 2H), 2.36-2.00 (m, 2H), 2.11 (s, 3H), 1.90-1.55 (m, 2H), 1.55-1.18 (m), 2.11 (s, 3H), 0.91 (t, J=7 Hz, 3H), 0.82 (t, J=7 Hz, 3H); ESI MS m/z 893 $[M+H]^+$.

Example 15

Preparation of 12'-(2-Thiazolyl)vinblastine solution of 12'-iodovinblastine (298 mg, 0.26 mmol) in THF (3 mL) was deoxygenated with an argon purge. Tetrakis(triphenylphosphine)palladium(0) (24 mg, 0.026 mmol) and 2-thiazolylzinc bromide (1.68 mL, 1.06 mmol) was added and the mixture heated at 60° C. overnight. The reaction mixture was diluted with brine and extracted with dichloromethane. The organic layers were combined and concentrated under reduced pressure. Purification by reversed phase chromatography (C18, acetonitrile/water, 0.05% concentrated ammonium hydroxide) gave 12'-(2-thiazolyl)vinblastine (32.8 mg, 14%). $^1$HNMR (300 MHz, $CD_3OD$) 8.15 (s, 1H), 7.83 (d, J=5 Hz, 1H), 7.72 (dd, J=7, 2 Hz, 1H), 7.53 (d, J=5 Hz, 1H), 7.36 (d, J=7 Hz, 1H), 6.51 (s, 1H), 6.38 (s, 1H), 5.87 (dd, J=10, 3 Hz, 1H), 5.41 (d, J=10 Hz, 1H), 5.34 (s, 1H), 4.66 (m, 1H), 4.23 (t, J=14 Hz, 1H), 3.85 (s, 3H), 3.78 (s, 3H), 3.70 (s, 3H), 3.63 (s, 1H), 3.60-3.10 (m), 3.11-2.84 (m, 3H), 2.81 (s, 3H), 2.61 (m, 1H), 2.51 (dd, J=15, 2 Hz, 1H), 2.17 (m, 1H), 2.15 (s, 1H), 2.09 (s, 3H), 2.05 (m, 1H), 1.84 (m, 1H), 1.68 (m, 3H), 1.55-1.43 (m, 4H), 1.01 (t, J=7 Hz, 3H), 0.74 (t, J=7 Hz, 3H); ESI m/z 894 $[M+H]^+$.

Example 16

Preparation of 12'-(Trimethylsilylethynyl)vinblastine

A solution of 12'-iodovinblastine (310 mg, 0.33 mmol) in toluene (5 mL) and triethylamine (3 mL) was deoxygenated with an argon purge, copper (I) iodide (2.5 mg, 0.013 mmol) and dichlorobis(triphenylphosphine)palladium(II) (10 mg) were added and the mixture deoxygenated again. Trimethylacetylene (0.06 mL, 0.42 mmol) was added and the mixture stirred at 55° C. for 24 h. After cooling, the reaction mixture was diluted with methanol and filtered through diatomaceous earth, concentrated to approximately 30 mL, filtered again and then concentrated to dryness. The mixture was diluted with 1 N HCl and extracted with chloroform. The organic solution was separated and concentrated under reduced pressure. Purification by flash chromatography (silica, 97:3 $CHCl_3$/MeOH) gave 12'-(trimethylsilylethynyl)vinblastine (28 mg, quant). 1H NMR (300 MHz, MeOD) δ 7.64 (s, 1H), 7.13 (s, 2H), 6.56 (s, 1H), 6.32 (s, 1H), 5.64 (dd, J=10, 4 Hz, 1H), 5.35 (s, 1H), 5.29 (d, J=10 Hz, 1H), 4.02 (t, J=13 Hz, 1H), 3.78 (s, 3H), 3.76 (s, 3H), 3.64 (s, 3H), 3.64 (m, 1H), 3.58 (s, 1H), 3.42 (d, J=13 Hz, 1H), 3.23-3.12 (m), 3.05 (d, J=13 Hz, 1H), 2.92-2.67 (m, 3H), 2.70 (s, 3H), 2.56-2.25 (m, 3H), 2.02 (s, 3H), 1.92-1.25 (m, 6H), 0.90 (t, J=7 Hz, 3H), 0.75 (t, J=7 Hz, 3H), 0.22 (s, 9H); ESI m/z 907 $[M+H]^+$.

Example 17

Preparation of 12'-Ethynylvinblastine

To a solution of 12'-(trimethylsilylethynyl)vinblastine (0.088 g, 0.097 mol) in methanol (1.8 mL) was added potassium carbonate (1.3 mg, 0.01 mmol) and the mixture stirred at room temperature for 4 h. The mixture was concentrated under reduced pressure, diluted with dichloromethane, washed with water and saturated sodium bicarbonate, dried ($Na_2SO_4$) and concentrated under reduced pressure. Purification by reversed phase chromatography (C18, acetonitrile/water, 0.05% concentrated ammonium hydroxide) gave 12'-(ethynyl)vinblastine 24.4 mg, 30%).

$^1$H NMR (300 MHz, MeOD) δ 7.60 (s, 1H), 7.16 (d, J=8 Hz, 1H), 7.13 (d, J=8 Hz, 1H), 6.58 (s, 1H), 6.32 (s, 1H), 5.82 (dd, J=10, 4 Hz, 1H), 5.36 (s, 1H), 5.29 (d, J=10 Hz, 1H), 4.01 (t, J=13 Hz, 1H), 3.95 (m, 1H), 3.81 (s, 3H), 3.76 (s, 3H), 3.66 (m, 1H), 3.65 (s, 3H), 3.58 (s, 1H), 3.45-3.12 (m), 3.02 (d, J=13 Hz, 1H), 2.88-2.67 (m, 4H), 2.71 (s, 3H), 2.47 (m, 2H), 2.38 (dd, J=13, 3 Hz, 1H), 2.03 (s, 3H), 1.87 (m, 1H), 1.66 (m, 1H), 1.56-1.25 (m, 5H), 0.90 (t, J=7 Hz, 3H), 0.76 (t, J=7 Hz, 3H); ESI m/z 835 $[M+H]^+$.

Example 18

Preparation 12'-Propynylvinblastine Trifluoroacetate

Propynylmagnesium bromide (0.5 M in THF, 0.30 mL, 0.15 mmol) was added to zinc bromide (0.5 M in THF, 0.30 mL, 0.15 mmol) in anhydrous 1,4-dioxane (2 mL) under nitrogen. After 10 min [1,1'-bis(diphenylphosphino)ferrocene]dichloropalladium (II) (6.1 mg, 0.008 mmol) was added followed by 12'-Iodovinblastine (71 mg, 0.076 mmol) in anhydrous 1,4-dioxane (1 mL). The reaction mixture was heated at 45° C. for 45 min then quenched by the addition of saturated aqueous $NaHCO_3$ (5 mL). After extraction with chloroform (3×8 mL) the combined organic extracts were washed with brine (5 mL), dried over $MgSO_4$, and evaporated to dryness in vacuo. The residue was purified by reverse phase chromatography (C18, acetonitrile/water, 0.05% trifluoroacetic acid) to provide 12'-propynylvinblastine trifluoroacetate (38.6 mg, 47%) as a white powder after lyophilization: $^1H$ NMR (500 MHz, $CD_3OD$) δ 9.71 (s, 1H), 7.56 (s, 1H), 7.20 (d, J=8.4 Hz, 1H), 7.12 (dd, J=8.4, 1.1 Hz, 1H), 6.66 (s, 1H), 6.42 (s, 1H), 5.94 (dd, J=10.4, 4.4 Hz, 1H), 5.65 (d, J=10.7 Hz, 1H), 5.36 (s, 1H), 4.84 (m, 1H), 4.63 (dd, J=16.9, 11.5, 1H), 3.96-3.56 (m, 7H), 3.86 (s, 3H), 3.82 (s, 3H), 3.69 (s, 3H), 3.48 (d, J=15.9 Hz, 1H), 3.19 (m, 3H), 2.88 (dd, J=14.4, 6.3 Hz, 1H), 2.77 (s, 3H), 2.47 (dd, J=16.6, 4.7 Hz, 1H), 2.35 (m, 1H), 2.07 (s, 3H), 2.04 (m, 2H), 2.01 (s, 3H), 1.74 (m, 1H), 1.66 (m, 2H), 1.52 (m, 3H), 1.38 (m, 1H), 0.97 (t, J=7.4 Hz, 3H), 0.79 (t, J=7.3 Hz, 3H); ESI MS m/z 849 $[M+H]^+$.

Example 19

Preparation of 12'-(2-Phenylethynyl)vinblastine

12'-(Phenylethynyl)vinblastine was prepared from 12'-iodovinblastine and phenylacetylene following the procedure described in Example 16 except that the reaction was run at room temperature (23 mg, 17%). $^1H$ NMR (300 MHz, MeOD) δ 7.55 (s, 1H), 7.40 (dd, J=8, 2 Hz, 2H), 7.25 (m, 3H), 7.14 (d, J=8 Hz, 1H), 7.08 (d, J=8 Hz, 1H), 6.50 (s, 1H), 6.22 (s, 1H), 5.75 (dd, J=10, 4 Hz, 1H), 5.27 (s, 1H), 5.20 (d, J=10 Hz, 1H), 4.53 (br s, 1H), 3.98 (t, J=14 Hz, 1H), 3.91 (m, 1H), 3.72 (s, 3H), 3.66 (s, 3H), 3.55 (s, 3H), 3.49 (s, 1H), 3.32 (d, J=14 Hz, 1H), 3.25-3.05 (m, 5H), 2.95 (d, J=14 Hz, 1H), 2.70 (m, 2H), 2.65 (s, 1H), 2.62 (s, 1H), 2.37 (m, 2H), 2.07 (dm, J=14 Hz, 1H), 2.00 (m, 1H), 1.93 (s, 3H), 2.77 (m, 1H), 1.57 (m, 1H), 1.50-1.15 (m, 5H), 0.78 (t, J=7 Hz, 3H), 0.68 (t, J=7 Hz, 3H); ESI m/z 911 $[M+H]^+$.

Example 20

Preparation of 12'-(3-Methylbutynyl)vinblastine Trifluoroacetate

12'-Iodovinblastine (52.7 mg, 0.056 mmol), copper(I) iodide (1.6 mg, 0.0084 mmol), dichlorobis(triphenylphosphine)palladium(II) (3.9 mg, 0.0056 mmol), toluene (1.2 mL), and triethylamine (0.8 mL) were combined in a resealable glass test tube and argon was bubbled through the solution for 10 min. 3-Methylbut-1-yne (22.9 mg, 0.33 mmol) was added, the test tube sealed, and the mixture was heated at 55° C. for 1.5 h. Saturated aqueous $NaHCO_3$ (5 mL) was added and the mixture was extracted with ethyl acetate (3×5 mL). The combined organic extracts were washed with brine (5 mL), dried over $MgSO_4$, and evaporated to dryness in vacuo. The residue was purified by reverse phase chromatography (C18, acetonitrile/water, 0.05% trifluoroacetic acid) to provide 12'-(3-methylbut-1-yne)vinblastine trifluoroacetate (24.0 mg, 40%) as a white solid after lyophilization: 1H NMR (300 MHz, $CD_3OD$) 37.56 (s, 1H), 7.20 (d, J=8.5 Hz, 1H), 7.13-7.11 (m, 1H), 6.59 (s, 1H), 6.40 (s, 1H), 5.91 (q, J=10.5, 6.0 Hz, 1H), 5.57-5.55 (m, 1H), 5.35 (s, 1H), 4.84-4.81 (m, 1H), 4.67-4.59 (m, 1H), 3.97-3.80 (m, 9H), 3.68-3.58 (m, 6H), 3.43-3.28 (m, 2H), 3.19-3.17 (m, 2H), 3.03-2.98 (m, 1H), 2.91-2.86 (m, 1H), 2.78-2.74 (m, 4H), 2.50-2.47 (m, 1H), 2.33-2.28 (m, 1H), 2.07-1.94 (m, 5H), 1.78-1.68 (m, 3H), 1.58-1.49 (m, 3H), 1.42-1.38 (m, 1H), 1.24 (d, J=7.0 Hz, 6H), 0.97 (t, J=7.5 Hz, 3H), 0.77 (t, J=7.0 Hz, 3H); ESI MS m/z 877 $[M+H]^+$.

Example 21

Preparation of 12'-(3-Methylbutynyl)vincristine

A solution of 12'-iodovincristine (210 mg, 0.22 mmol) and triethylamine (3 mL) in THF (3 mL) was deoxygenated with argon for 20 min. Dichlorobis(triphenylphosphine)palladium (II) (9 mg, 0.01 mmol) and copper(I) iodide was added, and the reaction mixture was again degassed with argon for 10 min followed by addition of 3-methyl-1-butyne (0.05 mL). The reaction mixture was heated at 60° C. overnight, cooled to room temperature, and quenched by the addition of 1 N HCl. The reaction mixture was extracted with methylene chloride and the organic layer was dried (sodium sulfate), filtered, and concentrated under reduced pressure to give a light orange solid. Purification by flash column chromatography (silica, 97:3 to 95: % $CH_2Cl_2$/MeOH) gave 12'-(3-methyl-butynl)vincristine (22 mg, 11%) as an orange solid: $^1H$ NMR (300 MHz, $CD_3OD$) δ 8.99 (s, 1H), 7.45 (s, 1H), 7.21-7.15 (m, 2H), 7.06 (d, J=7 Hz, 1H), 6.90 (s, 1H), 5.90 (m, 1H), 5.40 (d, J=6 Hz, 1H), 4.13-4.03 (m, 3H), 3.89 (s, 3H), 3.88 (m, 1H), 3.74 (m, 1H), 3.71 (s, 3H), 3.62 (s, 3H), 3.40 (m), 3.01 (m, 3H), 2.90-2.74 (m, 5H), 2.63 (m, 1H), 2.41 (m, 1H), 2.27 (m, 1H), 2.07 (m, 5H), 1.78 (m, 1H), 1.51-1.30 (m,), 1.28 (d, J=7 Hz, 6H), 0.89 (t, J=7 Hz, 3H), 0.76 (t, J=7 Hz, 3H); ESI MS m/z 891 $[M+]^+$.

Example 22

Preparation of 12'-(Hexynyl)vincristine

12'-(Hexynyl)vincristine was prepared from 12'-iodovinblastine following the procedure described in Example 16 (12 mg, 44%). $^1H$ NMR (300 MHz, $CD_3OD$) δ 8.95 (s, 1H), 7.54 (s, 1H), 7.24 (s, 1H), 7.23 (d, J=8 Hz, 1H), 7.11 (d, J=8 Hz, 1H), 6.86 (s, 1H), 5.88 (d, J=10, 5 Hz, 1H), 5.41 (d, J=10 Hz, 1H), 5.14 (s, 1H), 4.57 (s, 1H), 4.40 (dd, J=16, 11 Hz, 1H), 3.98 (t, J=15 Hz, 1H), 3.92 (s, 3H), 3.88 (s, 1H), 3.70 (s, 3H), 3.62 (s, 3H), 3.52 (m, 2H), 3.40-2.84 (m, 5H), 2.77 (m, 1H), 2.40 (m, 1H), 2.40 (t, J=7 Hz, 2H), 2.12 (m, 1H), 2.01 (m, 1H), 2.00 (s, 3H), 1.83 (m, 1H), 1.66-1.20 (m, 14H), 0.96 (t, J=7 Hz, 3H), 0.93 (t, J=7 Hz, 3H), 0.76 (t, J=7 Hz, 3H); ESI MS m/z 905 $[M+H]^+$.

Example 23

Preparation of 12'-(Hexynyl)vinblastine

12'-(Hexynyl)vinblastine was prepared from 12'-iodovinblastine following the procedure described in Example 16 (19 mg, 14%). $^1H$ NMR (300 MHz, $CD_3OD$) 37.77 (s, 1H), 7.26 (d, J=8 Hz, 1H), 7.14 (d, J=8 Hz, 1H), 6.32 (s, 1H), 6.25 (s, 1H), 5.83 (d, J=10, 5 Hz, 1H), 5.77 (d, J=5 Hz, 1H), 5.30 (s, 1H), 5.23 (d, J=10 Hz, 1H), 4.41 (s, 1H), 3.85 (s, 3H), 3.77 (m, 1H), 3.75 (s, 3H), 3.73 (s, 3H), 3.58 (s, 1H), 3.41 (m, 2H), 3.20 (m, 1H), 3.06 (m, 1H), 2.71 (s, 3H), 2.70-2.44 (m, 3H), 2.41 (t, J=7 Hz, 2H), 2.26 (m, 1H), 2.05 (m, 3H), 2.01 (s, 3H), 1.90 (br s, 1H), 1.79 (m, 1H), 1.66-1.20 (m, 10H), 0.96 (t, J=7 Hz, 3H), 0.93 (t, J=7 Hz, 3H), 0.76 (t, J=7 Hz, 3H); ESI MS m/z 859 [M+H]$^+$.

Example 24

Preparation of 12'-(N,N-Dimethylaminopropynyl)vinblastine Trifluoroacetate

12'-iodovinblastine (52.8 mg, 0.057 mmol), copper(I) iodide (1.6 mg, 0.0086 mmol), dichlorobis(triphenylphosphine)palladium(II) (4.0 mg, 0.0057 mmol), toluene (1.2 mL), and triethylamine (0.8 mL) were combined in a resealable glass test tube and argon was bubbled through the solution for 10 min. 1-Dimethylamino-2-propyne (36.7 μL, 0.33 mmol) was added, the test tube sealed, and the mixture was heated at 55° C. for 1.5 h. Saturated aqueous NaHCO$_3$ (5 mL) was added, and the mixture was extracted with ethyl acetate (3×5 mL). The combined organic extracts were washed with brine (5 mL), dried over MgSO$_4$, and evaporated to dryness in vacuo. The residue was purified by reverse phase chromatography (C18, acetonitrile/water, 0.05% trifluoroacetic acid) to provide 12'-(N,N-dimethylaminopropynyl)vinblastine trifluoroacetate (22.4 mg, 33%), which was a white solid after lyophilization: $^1$H NMR (300 MHz, CD$_3$OD) δ 9.91 (br s, 1H), 7.76 (s, 1H), 7.30-7.26 (m, 2H), 6.58 (s, 1H), 6.38 (s, 1H), 5.90 (t, J=10.5, 6.0 Hz, 1H), 5.52 (d, J=9.0 Hz, 1H), 5.33 (s, 1H), 4.90-4.81 (m, 1H), 4.66-4.61 (m, 1H), 4.27 (s, 2H), 3.96-3.84 (m, 5H), 3.79 (s, 3H), 3.69-3.62 (m, 7H), 3.55-3.48 (m, 1H), 3.33-2.29 (m, 1H), 3.20-3.16 (m, 3H), 3.00 (s, 6H), 2.89-2.85 (m, 1H), 2.75 (s, 3H), 2.50-2.45 (m, 1H), 2.24-2.21 (m, 1H), 2.05 (s, 3H), 2.03 (s, 1H), 1.97-1.89 (m, 1H), 1.74-1.67 (m, 3H), 1.57-1.49 (m, 3H), 1.40-1.45 (m, 1H), 0.96 (t, J=7.5 Hz, 3H), 0.75 (t, J=7.5 Hz, 3H); ESI MS m/z 892 [M+H]$^+$.

Example 25

Preparation of 12'-vinylvinblastine

A solution of 12'-iodovinblastine (39 mg, 0.042 mmol) in DME (0.5 mL) and water (0.2 mL) was deoxygenated with argon for 3 minutes. The reaction vessel was charged with 2,4,6-trivinylcyclotriboroxane pyridine complex (11 mg, 0.46 mmol), tetrakis(triphenylphosphine)palladium(0) (6.3 mg, 0.050 mmol), K$_2$CO$_3$ (6.4 mg, 0.046 mmol) and the mixture was heated to 80-90° C. After 2 h, the reaction appeared complete by ESI mass spectral analysis. The reaction mixture was diluted with saturated aqueous NaHCO$_3$ (8 mL) and extracted with EtOAc (2×2 mL). The combined extracts were dried (Na$_2$SO$_4$) and concentrated to a brown solid which was purified by flash chromatography (silica, [CHCl$_3$/MeOH/NH$_4$OH (40:18:2)]/CH$_2$Cl$_2$, 1:99 to 10:90) to yield 12'-vinylvinblastine (14 mg, 31%) as a white solid: $^1$H NMR (500 MHz, CD$_3$OD) δ 9.63 (br s, 1H), 7.51 (s, 1H), 7.33-7.31 (m, 1H), 7.23 (d, J=8.5 Hz, 1H), 6.81 (dd, J=17.5, 4.4 Hz, 1H), 6.67 (s, 1H), 6.42 (s, 1H), 5.97-5.92 (m, 1H), 5.70-5.64 (m, 2H), 5.35 (s, 1H), 5.08 (d, J=11.5 Hz, 1H), 4.67-460 (m, 1H), 3.97-3.88 (m, 2H), 2.87-2.81 (m, 6H), 3.75-3.58 (m, 6H), 3.50-3.47 (m, 1H), 3.37-3.33 (m, 1H), 3.23-3.17 (m, 3H), 2.91-2.88 (m, 1H), 2.78-2.77 (m, 4H), 2.49-2.44 (m, 1H), 2.37-2.32 (m, 1H), 2.08-2.00 (m, 5H), 1.78-1.67 (m, 3H), 1.57-1.36 (m, 5H), 0.97 (t, J=7.5 Hz, 3H), 0.81 (t, J=7.5 Hz, 3H); ESI MS m/z 837 [M+H]$^+$.

Example 26

Preparation of 12'-(2-Ethoxycarbonylvinyl)vinblastine

A solution of 12'-iodovinblastine (0.248 g, 0.26 mmol) in toluene (2 mL) was deoxygenated with argon. Palladium acetate (3 mg, 0.013 mmol), triphenylphosphine (32 mg, 0.12 mmol), and triethylamine (0.05 mL, 0.36 mmol) were added and the mixture deoxygenated again. After heating to 70° C., ethyl acrylate (0.058 mL, 0.53 mmol) was added and the mixture stirred overnight. The mixture was then cooled to room temperature, diluted with dichloromethane, filtered through diatomaceous earth, and concentrated under reduced pressure. Ethyl acetate was added and the mixture filtered through diatomaceous earth and concentrated under reduced pressure. Purification by reversed phase chromatography (C18, acetonitrile/water, 0.05% concentrated ammonium hydroxide) gave 12'-(2-ethoxycarbonylvinyl)vinblastine (24.3 mg, quant.). $^1$H NMR (300 MHz, MeOD) δ 7.80 (d, J=16 Hz, 1H), 7.62 (s, 1H), 7.41 (d, J=8 Hz, 1H), 7.21 (d, J=8 Hz, 1H), 6.58 (s, 1H), 6.39 (d, J=16 Hz, 1H), 6.32 (s, 1H), 5.80 (dd, J=10, 4 Hz, 1H), 5.36 (s, 1H), 5.30 (d, J=10 Hz, 1H), 4.23 (q, J=7 Hz, 2H), 4.05 (t, J=13 Hz, 1H), 3.95 (m, 1H), 3.81 (s, 3H), 3.76 (s, 3H), 3.66 (m, 1H), 3.65 (s, 3H), 3.58 (s, 1H), 3.02 (d, J=14 Hz, 1H), 3.34-3.15 (m, 4H), 3.07 (br d, J=13 Hz, 1H), 2.88-2.65 (m, 4H), 2.72 (s, 3H), 2.46 (m, 2H), 2.38 (dd, J=16, 5 Hz, 1H), 2.08 (m, 2H), 2.03 (s, 3H), 1.87 (m, 1H), 1.66 (m, 1H), 1.56-1.25 (m, 5H), 1.32 (t, J=7 Hz, 3H), 0.90 (t, J=7 Hz, 3H), 0.77 (t, J=7 Hz, 3H); ESI m/z 909 [M+H]$^+$.

Example 27

Preparation of 12'-(2-tert-Butoxycarbonylvinyl)vinblastine

To a solution of 12'-iodovinblastine (114 mg, 0.122 mmol) in toluene (2 mL) was added palladium acetate (2 mg, 0.009 mmol), triphenylphosphine (3.1 mg, 0.005 mmol), triethylamine (24 μL, 0.172 mmol) and the reaction mixture was deoxygenated with an argon purge. Tert-butyl acrylate (36 μL, 0.246 mmol) was added and the reaction mixture was heated to 70° C. After 1 h, HPLC analysis indicated that 12'-iodovinblastine was present so another equivalent of all reagents except 12'-iodovinblastine were added and the reaction mixture was heated to 70° C. for an additional 17 h. The reaction was cooled to room temperature, the mixture diluted with CH$_2$Cl$_2$ (15 mL) and then filtered through diatomaceous earth. The filtrate was concentrated to dryness, and the resulting residue was triturated with 9:1 ethyl acetate/methanol and the solid was removed by filtration. The filtrate was concentrated and the residue purified by column chromatography (silica, 9:1 EtOAc/MeOH) to give an orange solid which was further purified by reverse phase chromatography (C18, acetonitrile/water, 0.05% concentrated ammonium hydroxide) to give 12'-(2-tert-butoxycarbonylviny)vinblastine as a tan solid (13 mg, 11%): $^1$H-NMR (300 MHz, CD$_3$OD) δ 7.62 (d, J=15.9 Hz, 1H), 7.57 (s, 1H), 7.31 (d, J=8.5 Hz, 1H), 7.13 (d, J=8.8 Hz, 1H), 6.51 (s, 1H), 6.26 (d, J=15.8 Hz, 1H), 6.25 (s, 1H), 5.77 (dd, J=10.2, 4.2 Hz, 1H), 5.29 (s, 1H), 5.23 (d, J=10.2 Hz, 1H), 4.02-3.86 (m, 2H), 3.74 (s, 3H), 3.69 (s, 3H), 3.57 (s, 3H), 3.51 (s, 1H), 3.34-3.13 (m, 3H), 3.02-2.96 (m, 1H), 2.79-2.64 (m, 3H), 2.64 (s, 3H), 2.40-2.31 (m, 2H), 2.24-2.19 (m, 1H), 2.06-1.95 (m, 2H), 1.95 (s, 3H), 1.84-1.74

(m, 1H), 1.67-1.55 (m, 1H), 1.46 (s, 9H), 1.46-1.21 (m, 8H), 0.83 (t, J=5.0 Hz, 3H), 0.70 (t, J=6.9 Hz, 3H); ESI MS m/z 938 [M$_1$+H]$^+$.

Example 28

Preparation of 12'-(2-Carboxyvinyl)vinblastine

A mixture of 12'-(2-tert-butoxycarbonylvinyl)vinblastine (17 mg, 0.018 mmol) in CH$_2$Cl$_2$ (1 mL) was treated with trifluoroacetic acid (45 µL, 0.069 mmol) at room temperature. After 3.5 h, HPLC indicated that the reaction was complete. The reaction was quenched with saturated aqueous sodium bicarbonate, diluted with CH$_2$Cl$_2$ and the layers were separated. The aqueous phase was extracted with CH$_2$Cl$_2$ (2×10 mL). The combined organics were dried over MgSO$_4$, filtered and concentrated to give 12'-(2-carboxyvinyl)vinblastine as a brown solid (9.4 mg, 59%): $^1$H NMR (300 MHz, CD$_3$OD) δ 7.49 (s, 1H), 7.44 (d, J=15.9 Hz, 1H), 7.26 (d, J=8.5 Hz, 1H), 7.11-7.02 (m, 2H), 6.50 (s, 1H), 6.34 (d, J=15.8 Hz, 1H), 6.22 (s, 1H), 5.75 (dd, J=10.2, 4.6 Hz, 1H), 5.27 (s, 1H), 5.20 (d, J=9.9 Hz, 1H), 4.75-4.65 (m, 1H), 4.00-3.85 (m, 2H), 3.71 (s, 3H), 3.65 (s, 3H), 3.55 (s, 3H), 3.47 (s, 2H), 3.33 (d, J=14.3 Hz, 1H), 2.99 (d, J=13.3 Hz, 1H), 2.61 (s, 3H), 2.77-2.52 (m, 6H), 2.39-2.34 (m, 2H), 2.23-2.17 (m, 2H), 1.93 (s, 3H), 1.84-1.74 (m, 1H), 1.62-1.53 (m, 1H), 1.47-1.18 (m, 6H), 0.81 (t, J=7.1 Hz, 3H), 0.69 (t, J=7.0 Hz, 3H); ESI MS m/z 881 [M+H]$^+$.

Example 29

Preparation of 12'-(3-Oxohex-1-enyl)vinblastine

12'-(3-Oxohex-1-enyl)vinblastine was prepared from 12'-iodovinblastine and hexen-3-one following the procedure described in Example 26, yield (90 mg, 42%). $^1$H NMR (300 MHz, MeOD) δ 7.80 (d, J=16 Hz, 1H), 7.73 (s, 1H), 7.45 (d, J=8 Hz, 1H), 7.22 (d, J=8 Hz, 1H), 6.39 (d, J=16 Hz, 1H), 6.58 (s, 1H), 6.32 (s, 1H), 5.84 (dd, J=10, 4 Hz, 1H), 5.49 (s, 1H), 5.34 (d, J=10 Hz, 1H), 4.06 (t, J=13 Hz, 1H), 3.95 (m, 1H), 3.81 (s, 3H), 3.76 (s, 3H), 3.65 (s, 3H), 3.64 (m, 1H), 3.58 (s, 1H), 3.39 (d, J=14 Hz, 1H), 3.36-3.15 (m, 4H), 3.07 (br d, J=14 Hz, 1H), 2.88-2.54 (m, 3H), 2.70 (s, 3H), 2.69 (t, J=7 Hz, 2H), 2.42 (m, 2H), 2.28 (dd, J=16, 5 Hz, 1H), 2.08 (m, 2H), 2.03 (s, 3H), 1.87 (m, 1H), 1.68 (sex, J=7 Hz, 2H), 1.66 (m, 1H), 1.56-1.25 (m, 6H), 0.99 (t, J=7 Hz, 3H), 0.88 (t, J=7 Hz, 3H), 0.77 (t, J=7 Hz, 3H); ESI m/z 907 [M+H]$^+$.

Example 30

Preparation of 12'-(2-Cyanovinyl)vinblastine

12'-(2-cyanovinyl)vinblastine was prepared from 12'-iodovinblastine and acrylonitrile following the procedure described in Example 26, yield (10 mg, 4%): $^1$H NMR (300 MHz, MeOD) δ 7.67 (s, 1H), 7.62 (d, J=17 Hz, 1H), 7.37 (d, J=8 Hz, 1H), 7.24 (d, J=8 Hz, 1H), 6.57 (s, 1H), 6.31 (s, 1H), 6.06 (d, J=17 Hz, 1H), 6.29 (m, 1H), 5.84 (dd, J=10, 4 Hz, 1H), 5.35 (s, 1H), 5.31 (d, J=10 Hz, 1H), 4.00 (m, 2H), 3.81 (s, 3H), 3.75 (s, 3H), 3.64 (s, 3H), 3.64 (m, 1H), 3.58 (s, 1H), 3.38 (d, J=14 Hz, 1H), 3.36-3.15 (m, 2H), 3.07 (br d, J=14 Hz, 1H), 2.88-2.54 (m, 2H), 2.73 (s, 1H), 2.72 (s, 3H), 2.45 (m, 2H), 2.27 (br d, J=14 Hz, 1H), 2.08 (m, 2H), 2.03 (s, 3H), 1.84 (m, 1H), 1.66 (m, 1H), 1.56-1.25 (m, 6H), 0.90 (t, J=7 Hz, 3H), 0.75 (t, J=7 Hz, 3H); ESI m/z 862 [M+H]$^+$.

Example 31

Preparation of 12'-(3-tert-Butoxycarbonylaminopropenyl)vinblastine

12'-(3-tert-Butoxycarbonylaminopropenyl)vinblastine was prepared from 12'-iodovinblastine and t-butyl-N-allyl-carbonate following the procedure described in Example 26, yield (24 mg, 9%): $^1$H NMR (300 MHz, MeOD) δ 7.41 (s, 1H), 7.20 (d, J=8 Hz, 1H), 7.08 (d, J=8 Hz, 1H), 6.60 (d, J=15 Hz, 1H), 6.60 (s, 1H), 6.33 (s, 1H), 6.10 (dt, J=15, 6 Hz, 1H), 5.84 (dd, J=10, 4 Hz, 1H), 5.49 (s, 1H), 5.36 (s, 1H), 5.28 (d, J=10 Hz, 1H), 4.22 (d, J=5 Hz, 2H), 4.04 (m, 2H), 3.81 (s, 3H), 3.81 (m, 1H), 3.76 (s, 3H), 3.64 (s, 3H), 3.58 (s, 1H), 3.42 (d, J=15 Hz, 1H), 3.36-3.15 (m, 4H), 3.04 (br d, J=15 Hz, 1H), 2.78 (m, 2H), 2.73 (s, 1H), 2.71 (s, 3H), 2.44 (m, 2H), 2.28 (br d, J=14 Hz, 1H), 2.08 (m, 1H), 2.03 (s, 3H), 1.87 (m, 1H), 1.66 (m, 1H), 1.56-1.25 (m, 6H), 1.48 (s, 9H), 0.90 (t, J=7 Hz, 3H), 0.78 (t, J=7 Hz, 3H); ESI m/z 966 [M+H]$^+$.

Example 32

Preparation of 12'-(4-Hydroxybutylsulfanyl)vinblastine

A flask containing compound 12'-iodovinblastine (200 mg, 0.214 mmol), tris(dibenzylideneacetone)dipalladium(0) (19.6 mg, 0.0214 mmol) and 1,1'-bis(diphenylphosphino)ferrocene (47.5 mg, 0.0856 mmol) was flushed with argon. Triethylamine (47 µL, 0.428 mmol), N-methylpyrrolidine (4 mL) and 4-mercaptobutan-1-ol (44 µL, 0.428 mmol) were added by syringe and the mixture was heated at 60° C. for 2 d. After cooling, the mixture was diluted with dichloromethane and washed with brine. The aqueous layer was extracted with dichloromethane and the combined organic layers concentrated under reduced pressure and dried under high vacuum. Purification by reversed phasechromatography (C18, acetonitrile/water, 0.05% concentrated ammonium hydroxide) gave 12'-(4-hydroxybutylsufanyl)vinblastine (0.030 g, 15%). $^1$H NMR (300 MHz, CDCl$_3$) δ 9.83 (s, 1H), 8.04 (s, 1H), 7.60 (s, 1H), 7.23 (dd, J=8, 1 Hz, 1H), 7.04 (d, J=7 Hz, 1H), 6.58 (s, 1H), 6.09 (s, 1H), 5.87 (dd, J=10, 4 Hz, 1H), 5.46 (s, 1H), 5.29 (d, J=10 Hz, 1H), 3.97 (t, J=15 Hz, 1H), 3.80-3.60 (m, 3H), 3.79 (s, 6H), 3.73 (s, 1H), 3.62 (s, 3H), 3.38-3.29 (m, 4H), 3.09 (m, 2H), 2.93 (m, 2H), 2.85 (s, 1H), 2.84 (s, 3H), 2.80 (br s, 2H), 2.65 (s, 1H), 2.43 (m, 2H), 2.25 (d, J=15 Hz, 1H), 2.21 (m, 1H), 2.11 (s, 3H), 1.90-1.20 (m), 1.48-1.28 (m, 6H), 0.89 (t, J=7 Hz, 3H), 0.76 (t, J=7 Hz, 3H); ESI MS m/z 915 [M+H]$^+$.

Example 33

Preparation of 12'-(4-Hydroxypropylsulfanyl)vinblastine

12'-(4-Hydroxypropylsufanyl)vinblastine was prepared from 12'-iodovinblastine and 3-mercaptopropan-1-ol following the procedure described in Example 33, yield (16 mg, 8%): $^1$H NMR (300 MHz, CDCl$_3$) δ 9.68 (s, 1H), 8.74 (s, 1H), 7.42 (s, 1H), 7.24 (d, J=8 Hz, 1H), 7.06 (dd, J=8, 1 Hz, 1H), 6.54 (s, 1H), 6.36 (s, 1H), 5.78 (dd, J=10, 4 Hz, 1H), 5.29 (d, J=10 Hz, 1H), 5.14 (s, 1H), 4.48 (t, J=5 Hz, 1H), 4.01 (m, 2H), 3.74 (s, 3H), 3.67 (s, 3H), 3.55 (s, 3H), 3.53 (s, 1H), 3.45 (q, J=6 Hz, 1H), 3.40-3.30 (m, 5H), 2.95-2.60 (m, 7H), 2.87 (t, J=7 Hz, 2H), 2.65 (s, 3H), 2.55-2.30 (m, 5H), 2.02 (m, 1H), 2.01 (s, 3H), 1.64 (m, 2H), 1.53 (m, 1H), 1.31 (m, 1H), 1.19 (m, 2H), 0.78 (t, J=7 Hz, 3H), 0.66 (t, J=7 Hz, 3H); ESI MS m/z 901 [M+H]$^+$.

Example 34

Preparation of 12'-(3-Methanesulfonyloxypropylsulfanyl)vinblastine

A mixture of 12'-(3-hydroxypropylthio)vinblastine (77 mg, 0.085 mmol) and triethylamine (24 μL, 0.17 mmol) in dichloromethane (2.0 mL) was treated with methanesulfonyl chloride (7.6 μL, 0.097 mmol) at 0° C. and the reaction was stirred at room temperature for 4 h. The reaction mixture was diluted with dichloromethane and the mixture was washed with saturated NaHCO$_3$ and brine. The organic layer was dried over MgSO$_4$ and then concentrated to afford an orange solid. Purification by column chromatography (silica gel, CH$_2$Cl$_2$/CH$_3$OH, 39:1) gave 12'-(3-methanesulfonyloxypropylsulfanyl)vinblastine as an off-white solid (40 mg, 48%): $^1$H NMR (300 MHz, CD$_3$OD) δ 7.59 (s, 1H), 7.22 (dd, J=8.4, 1.4 Hz, 1H), 7.16 (d, J=8.3 Hz, 1H), 6.62 (s, 1H), 6.33 (s, 1H), 5.86 (dd, J=9.9, 3.7 Hz, 1H), 5.38 (s, 1H), 5.31, (d, J=10.2 Hz, 1H), 4.35 (t, J=6.1 Hz, 2H), 4.15-4.06 (m, 1H), 4.01-3.91 (m, 1H), 3.82 (s, 3H), 3.78 (s, 3H), 3.65 (s, 3H), 3.70-3.60 (m, 1H), 3.43 (m, 10H), 3.08-2.93 (m, 2H), 3.02 (s, 3H), 2.87-2.70 (m, 2H), 2.73 (s, 3H), 2.49-2.54 (m, 1H), 2.32-2.25 (m, 1H), 2.15-1.84 (m, 3H), 2.04 (s, 3H), 1.73-1.64 (m, 1H), 1.54-1.21 (m, 6H), 0.91 (t, J=7.3 Hz, 3H), 0.79 (t, J=7.2 Hz, 3H); ESI MS m/z 979 [M+H]$^+$.

Example 35

Preparation of 12'-(2-Hydroxyethylsulfanyl)vinblastine

12'-(2-Hydroxyethylsulfanyl)vinblastine was prepared from 12'-iodovinblastine and 2-mercaptoethanol following the procedure described in Example 33, yield (33 mg, 17%) as an off-white powder: 1H NMR (300 MHz, DMSO-d$_6$) δ 10.05 (br s, 1H), 8.97 (br s, 1H), 7.64 (s, 1H), 7.31 (d, J=8 Hz, 1H), 7.18 (dd, J=8, 1 Hz, 1H), 6.40 (s, 1H), 5.81 (dd, J=10, 4 Hz, 1H), 5.34 (br s, 1H), 5.01 (m, 2H), 4.82 (m, 1H), 4.34 (m, 1H), 3.85 (t, J=15 Hz, 1H), 3.80-3.10 (m), 3.77 (s, 3H), 3.66 (s, 3H), 3.60 (s, 3H), 3.02-2.98 (m, 4H), 2.71 (m, 3H), 2.15 (m, 2H), 2.01 (s, 3H), 1.73 (m, 1H), 1.60-1.35 (m, 6H), 1.16 (m, 1H), 0.88 (t, J=8 Hz, 3H), 0.67 (t, J=8 Hz, 3H); ESI MS m/z 887 [M+H]$^+$.

Example 36

Preparation of 12'-(4-Methoxybenzylsulfanyl)vinblastine

A mixture of 12'-iodovinblastine (200 mg, 0.214 mmol), 1,1'-bis(diphenylphosphino)ferrocene (48 mg, 0.09 mmol), and tris(dibenzylideneacetone)dipalladium(0) (20 mg, 0.02 mmol) in NMP (4 mL) was deoxygenated with argon for 10 min. Triethylamine (47 μL) and thiol (66 mg, 0.428 mmol) were added and the reaction mixture was heated to 60° C. for 72 h. The reaction mixture was cooled to room temperature, and partitioned between brine and methylene chloride. The organic layer was separated and concentrated under reduced pressure. The resulting residue was purified by chromatography (silica, 9:1 CH$_2$Cl$_2$/MeOH), then further purified by reverse phase chromatography (C18, acetonitrile/water, 0.05% concentrated ammonium hydroxide) to provide 12'-(4-methoxybenzylsulfanyl)vinblastine (3 mg, 1%) as a white solid: 1H NMR (300 MHz, CDCl$_3$) δ 8.08 (br s, 1H), 7.45 (s, 1H), 7.22 (d, J=9 Hz, 2H), 7.03 (d, J=9 Hz, 1H), 6.85 (d, J=8 Hz, 2H), 6.39 (s, 1H), 6.09 (s, 1H), 5.90 (dd, J=10, 4 Hz, 1H), 5.39 (m, 2H), 4.46 (m, 1H), 4.11 (s, 2H), 3.89-3.35 (m), 3.68 (s, 3H), 3.28 (m, 2H), 3.09-2.84 (m, 5H), 2.47 (d, J=16 Hz, 1H), 2.27 (m, 1H), 2.13 (s, 3H), 2.00-1.20 (m), 0.99 (t, J=8 Hz, 3H), 0.73 (t, J=7 Hz, 3H); ESI MS m/z 963 [M+H]$^+$.

Example 37

Preparation of 12'-(2-Chlorobenzylsulfanyl)vincristine solution of 11'-iodovincristine (60 mg, 0.063 mmol) in NMP (3 mL) was deoxygenated with argon for 10 minutes. The reaction vessel was charged with 1,1'-bis(diphenylphosphino)ferrocene (20 mg, 0.035 mmol), tris(dibenzylideneacetone)dipalladium(0) (9 mg, 0.009 mmol) and Et$_3$N (13 mg, 0.13 mmol). The mixture was stirred for 10 min at room temperature; 2-chlorobenzenmethane-thiol (20 mg, 0.126 mmol) was added and then the mixture stirred at 60° C. overnight. The mixture was cooled to room temperature, diluted with methylene chloride (100 mL) and washed with saturated aqueous NH$_4$Cl (3×10 mL) and brine (3×10 mL). The organic layer was dried (Na$_2$SO$_4$), filtered and concentrated. The residue was purified by flash chromatography (silical, 10:1 CH$_2$Cl$_2$/MeOH) and then reverse phase chromatography (C-18, acetonitrile/water, 0.05% trifluoroacetic acid) to give 12 mg of white solid. This solid was dissolved in 10 mL of EtOAc and stirred with 50 mg of solid NaHCO$_3$ for 1 h. The mixture was filtered, concentrated to give 12'-(2-chlorobenzylsulfanyl)vincristine (9.7 mg, 15%) as an off-white solid: mp 168-170° C.; 1H NMR (500 MHz, CD$_3$OD) δ 8.95 (s, 1H), 7.46 (s, 1H), 7.37 (d, J=8.0 Hz, 1H), 7.36 (s, 1H), 7.25 (d, J=8.5 Hz, 1H), 7.20-7.11 (m, 4H), 6.98 (s, 1H), 5.97 (dd, J=11.0, 5.0 Hz, 1H), 5.74 (d, J=10.5 Hz, 1H), 5.48 (s, 1H), 5.18 (s, 1H), 4.67 (s, 1H), 4.64 (dd, J=17.0, 11.0 Hz, 1H), 4.15 (q, J=11.0 Hz, 2H), 4.08 (s, 1H), 3.99-3.94 (m, 2H), 3.92 (s, 3H), 3.68-3.81 (m, 3H), 3.73 (s, 3H), 3.68 (s, 3H), 3.57 (dd, J=11.2, 6.5 Hz, 1H), 3.54-3.49 (m, 2H), 3.34 (dd, J=7.5, 5.0 Hz, 1H), 3.22 (dd, J=17.5, 6.5 Hz, 1H), 3.16 (s, 1H), 2.84 (dd, J=14.5, 3.6 Hz, 1H), 2.51-2.47 (m, 1H), 2.42-2.34 (m, 1H), 2.02 (s, 3H), 1.99-1.92 (m, 1H), 1.67-1.60 (m, 3H), 1.51 (q, J=7.5 Hz, 3H), 1.32-1.28 (m, 1H), 0.96 (t, J=7.0 Hz, 3H), 0.80 (t, J=7.5 Hz, 3H); ESI MS m/z 981 [M+H]$^+$.

Example 38

Preparation of 12'-(2-Fluorobenzylsulfanyl)vincristine Trifluoroacetate

A solution of 12'-iodovincristine (50 mg, 0.053 mmol) in NMP (1.5 mL) was deoxygenated with argon for 10 minutes. The reaction vessel was charged with 1,1'-bis(diphenylphosphino)ferrocene (20 mg, 0.035 mmol), tris(dibenzylideneacetone)dipalladium(0) (10 mg, 0.011 mmol) and Et$_3$N (13 mg, 0.13 mmol). The mixture was stirred for 20 min at room temperature, 2-fluorophenylmethane-thiol (20 mg, 0.14 mmol) was added and then the mixture stirred at 60° C. overnight. The mixture was cooled to room temperature, diluted with EtOAc (100 mL) and washed with saturated aqueous NH$_4$Cl (3×10 mL) and brine (3×10 mL). The organic layer was dried (Na$_2$SO$_4$), filtered and concentrated. The residue was purified by chromatography (silica, 4:1 CH$_2$Cl$_2$/MeOH), then further purified by reverse phase chromatography (C-18, acetonitrile/water, 0.05% trifluoroacetic acid) to give 12'-(2-fluorobenzylsulfanyl)vincristine (8 mg, 15%) as a light brown solid: 1H NMR (500 MHz, CD$_3$OD) δ 9.98 (s, 1H), 8.99 (s, 1H), 7.46 (s, 1H), 7.34 (s, 1H), 7.28-7.13 (m, 4H), 7.04-6.99 (m, 3H), 5.98 (dd, J=10.5, 5.5 Hz, 1H), 5.73 (d, J=10.0 Hz, 1H), 5.18 (s, 1H), 4.67 (s, 1H), 4.64 (dd, J=17.5, 11.0 Hz, 1H), 4.09-4.04 (m, 3H), 3.99-3.94 (m, 5H), 3.86-3.79 (m, 2H), 3.76-3.73 (m, 1H), 3.72 (s, 3H), 3.67 (s, 3H), 3.58-3.50 (m, 3H), 3.40-3.37 (m, 1H), 3.23 (dd, J=7.5, 5.5 Hz, 1H), 3.18 (s, 2H), 2.83 (dd, J=14.0, 6.0 Hz, 1H), 2.49-2.46 (m, 1H), 2.40-2.36 (m, 1H), 2.08-1.93 (m, 4H), 1.66-1.60 (m, 3H), 1.53-1.49 (m, 3H), 1.32-1.28 (m, 1H), 0.96 (t, J=7.0 Hz, 3H), 0.80 (t, J=7.0 Hz, 3H); ESI MS m/z 965 [M+H]$^+$.

Example 39

Preparation of 12'-(Propylsulfanyl)vinblastine

A stirred solution of 12'-iodovinblastine (200 mg, 0.214 mmol), 1,1'-bis(diphenylphosphino)ferrocene (48 mg, 0.09 mmol), tris(dibenzylideneacetone)dipalladium(0) (20 mg, 0.02 mmol) in NMP (2 mL) was deoxygenated with argon for 10 min followed by the addition of triethylamine (47 μL, 0.428 mmol) and 1-propanethiol (39 μL, 0.428 mmol). The reaction mixture was heated to 60° C. for 5 h, cooled to room temperature, and then partitioned between methylene chloride and brine. The organic layer was concentrated under reduced pressure and the residue purified by chromatography (silica, 85:15 MeOH/CH$_2$Cl$_2$), then further purified by reverse phase chromatography (C18, acetontrile/water, 0.05% concentrated ammonium hydroxide) to give 12'-(propylsulfanyl)vinblastine (36 mg, 19%) as a tan solid: 1H NMR (300 MHz, CDCl$_3$) δ 8.21 (br s, 1H), 7.57 (s, 1H), 7.29 (dd, J=9, 1 Hz, 1H), 7.05 (d, J=9 Hz, 1H), 6.63 (s, 1H), 6.11 (s, 1H), 5.90 (dd, J=10, 4 Hz, 1H), 5.49 (d, J=10 Hz, 1H), 5.39 (s, 1H), 4.53 (m, 1H), 4.14 (m, 2H), 4.10 (m, 1H), 3.83 (s, 3H), 3.82 (s, 3H), 3.63 (s, 3H), 3.89-3.56 (m, 5H), 3.41 (br s, 1H), 3.30 (d, J=15 Hz, 1H), 3.17 (m, 2H), 2.87 (t, J=7 Hz, 4H), 2.82 (m, 2H), 2.70-2.25 (m), 2.08 (s, 3H), 1.82-1.21 (m, 10H), 1.05 (m, 6H), 0.72 (t, J=7 Hz, 3H); ESI MS m/z 885 [M+H]$^+$.

Example 40

Preparation of 12'-(Ethylsulfanyl)vincristine L-Tartrate

12'-iodovincristine (650 mg, 0.684 mmol), tris(dibenzylideneacetone)dipalladium(0) (94 mg, 0.10 mmol), 1,1'-bis(diphenylphosphino)ferrocene (227 mg, 0.410 mmol), 1-methyl-2-pyrrolidinone (6 mL), and triethylamine (0.23 mL) were combined in a resealable glass test tube. Argon was bubbled through the solution for 10 min, then ethanethiol (0.25 mL, 3.4 mmol) was added, the test tube sealed, and the mixture was heated to 60° C. After 4 h, additional ethanethiol (0.25 mL, 3.4 mmol) was added, and the mixture was heated to 60° C. overnight. After cooling, the mixture was diluted with ethyl acetate (250 mL), washed with saturated aqueous NH$_4$Cl (3×20 mL), water and brine, then dried (Na$_2$SO$_4$) and evaporated to dryness under vacuum. The residue was purified by reverse phase chromatography (C18, acetonitrile/water, 0.05% trifluoroacetic acid) to provide 12'-(ethylsulfanyl)vincristine trifluoroacetate (130 mg, 17%) as a white powder after lyophilization. After conversion to the free base, treatment with 2 equivalents of L-tartaric acid gave 12'-(ethylsulfanyl)vincristine as a salt of L-tartrate:

$^1$H NMR (500 MHz, CD$_3$OD) δ 8.95 (s, 1H), 7.61 (s, 1H), 7.28-7.26 (m, 2H), 7.22 (dd, J=8.5, 1.5 Hz, 1H), 6.90 (s, 1H), 5.92 (dd, J=10.0, 4.5 Hz, 1H), 5.48 (d, J=10.0 Hz, 1H), 5.14 (s, 1H), 4.64-4.59 (m, 2H), 4.42 (s, 4H), 3.40-3.89 (m, 4H), 3.80 (d, J=16.0 Hz, 1H), 3.72-3.57 (m, 9H), 3.47 (dd, J=16.0, 5.0 Hz, 2H), 3.40-3.38 (m, 1H), 3.33-3.27 (m, 1H), 3.20 (d, J=14.0 Hz, 1H), 3.10 (d, J=14.0 Hz, 1H), 3.00 (d, J=16.0 Hz, 1H), 2.88-2.83 (m, 4H), 2.47 (d, J=11.5 Hz, 1H), 2.17-2.08 (m, 1H), 2.00 (s, 3H), 1.88-1.79 (m, 1H), 1.64-1.40 (m, 7H), 1.21 (t, J=7.5 Hz, 3H), 0.96 (t, J=7.5 Hz, 3H), 0.78 (t, J=7.5 Hz, 3H); ESI MS m/z 885 [M+H]$^+$.

Example 41

Preparation of 12'-(Ethylsulfanyl)vinblastine Trifluoroacetate

12'-iodovinblastine (100 mg, 0.10 mmol), tris(dibenzylideneacetone)dipalladium(0) (14 mg, 0.015 mmol), 1,1'-bis(diphenylphosphino)ferrocene (33 mg, 0.060 mmol), 1-methyl-2-pyrrolidinone (1 mL), and triethylamine (34 μL) were combined in a resealable glass test tube. Argon was bubbled through the solution for 10 min, then ethanethiol (37 μL, 0.50 mmol) was added, the test tube sealed, and the mixture was heated to 60° C. After 4 h, additional ethanethiol (75 μL, 1.0 mmol) was added, and the mixture was heated to 60° C. overnight. After cooling, the mixture was diluted with ethyl acetate (100 mL), washed with saturated aqueous NH$_4$Cl (3×15 mL), water and brine, then dried (Na$_2$SO$_4$) and evaporated to dryness under vacuum. The residue was purified by reverse phase chromatography (C18, acetonitrile/water, 0.05% trifluoroacetic acid) to provide 12'-(ethylsulfanyl)vinblastine trifluoroacetate (10 mg, 11%) as a white powder after lyophilization: 1H NMR (500 MHz, CD$_3$OD) δ 9.75 (br s, 1H), 7.61 (s, 1H), 7.26-7.21 (m, 2H), 6.70 (s, 1H), 6.42 (s, 1H), 5.95 (dd, J=10.5, 5.0 Hz, 1H), 5.66 (d, J=10.0 Hz, 1H), 5.35 (s, 1H), 4.64 (dd, J=17.5, 11.5, 1H), 3.97-3.91 (m, 3H), 3.86 (s, 3H), 3.82 (s, 3H), 3.77-3.57 (m, 8H), 3.49 (d, J=16.0 Hz, 1H), 3.34-3.31 (m, 1H), 3.27-3.16 (m, 3H), 2.89 (dd, J=14.5, 6.5 Hz, 1H), 2.85 (q, J=7.5 Hz, 2H), 2.78 (s, 3H), 2.46 (dd, J=15.5, 4.5 Hz, 1H), 2.37-2.31 (m, 1H), 2.07 (s, 2H), 2.05-1.99 (m, 2H), 1.78-1.50 (m, 6H), 1.39-1.32 (m, 1H), 1.21 (t, J=7.5 Hz, 3H), 0.97 (t, J=7.5 Hz, 3H), 0.80 (t, J=7.5 Hz, 3H); ESI MS m/z 871 [M+H]$^+$.

Example 42

Preparation of 12'-(Methylsulfanyl)vincristine Trifluoroacetate

12'-iodovincristine (85 mg, 0.089 mmol), tris(dibenzylideneacetone)dipalladium(0) (12 mg, 0.013 mmol), 1,1'-bis(diphenylphosphino)ferrocene (30 mg, 0.053 mmol), 1-methyl-2-pyrrolidinone (1 mL), and triethylamine (31 μL) were combined in a resealable glass test tube. Argon was bubbled through the solution for 10 min, and methanethiol (0.22 mL of a 4 N solution in NMP, 0.89 mmol) was added, the test tube sealed, and the mixture was heated to 65° C. After 3 h, additional methanethiol (0.22 mL of a 4 N solution in NMP, 0.89 mmol) was added, and the mixture was heated to 65° C. overnight. After cooling, the mixture was diluted with ethyl acetate (100 mL), washed with saturated aqueous NH$_4$Cl (3×15 mL), water and brine, then dried (Na$_2$SO$_4$) and evaporated to dryness in vacuo. The residue was purified by reverse phase chromatography (C18, acetonitrile/water, 0.05% trifluoroacetic acid) to provide 12'-(methylsulfanyl)vincristine trifluoroacetate (9 mg, 9%) as a white powder after lyophilization: ¹H NMR (500 MHz, CD₃OD) δ 9.91 (br s, 1H), 8.99 (s, 1H), 7.55 (s, 1H), 7.34 (s, 1H), 7.29 (d, J=8.5 Hz, 1H), 7.19 (d, J=8.5 Hz, 1H), 6.96 (s, 1H), 5.98 (dd, J=10.0, 5.0 Hz, 1H), 5.74 (d, J=10.0 Hz, 1H), 5.19 (s, 1H), 4.69-4.67 (m, 2H), 4.03-3.76 (m, 11H), 3.73 (s, 3H), 3.67 (s, 3H), 3.52 (d, J=16.0 Hz, 1H), 3.36-3.32 (m, 1H), 3.17 (s, 2H), 2.84 (dd, J=14.0, 5.5 Hz, 1H), 2.54-2.46 (m, 1H), 2.45 (s, 3H), 2.44-2.36 (m, 1H), 2.05 (s, 3H), 2.03-1.93 (m, 1H), 1.68-1.58 (m, 3H), 1.54-1.47 (m, 3H), 1.31-1.29 (m, 1H), 0.97 (t, J=7.5 Hz, 3H), 0.83 (t, J=7.5 Hz, 3H); ESI MS m/z 871 [M+H]⁺.

Example 43

Preparation of 12'-(Methylsulfanyl)vinblastine Trifluoroacetate

12'-iodovinblastine (45 mg, 0.048 mmol), tris(dibenzylideneacetone)dipalladium(0) (9.0 mg, 0.0096 mmol), 1,1'-bis(diphenylphosphino)ferrocene (21 mg, 0.038 mmol), 1-methyl-2-pyrrolidinone (0.5 mL), and triethylamine (17 µL) were combined in a resealable glass test tube. Argon was bubbled through the solution for 10 min, then methanethiol was bubbled through for 10 sec, the test tube sealed, and the mixture was heated to 60° C. for 5 h. After cooling, the mixture was diluted with ethyl acetate (75 mL), washed with saturated aqueous NH₄Cl (3×15 mL), water and brine, then dried (Na₂SO₄) and evaporated to dryness under vacuum. The residue was purified by reverse phase chromatography (C18, acetonitrile/water, 0.05% trifluoroacetic acid) to provide 12'-(methylsulfanyl)vinblastine trifluoroacetate (3.5 mg, 7%) as a white powder after lyophilization: 1H NMR (500 MHz, CD₃OD) δ 7.54 (s, 1H), 7.24 (d, J=8.5 Hz, 1H), 7.18 (dd, J=8.5, 1.5 Hz, 1H), 6.67 (s, 1H), 6.42 (s, 1H), 5.94 (dd, J=10.5, 5.0 Hz, 1H), 5.66 (d, J=10.5 Hz, 1H), 5.35 (s, 1H), 4.63 (dd, J=17.0, 11.0 Hz, 1H), 3.97-3.90 (m, 3H), 3.86 (s, 3H), 3.82 (s, 3H), 3.79-3.58 (m, 8H), 3.49 (d, J=15.5 Hz, 1H), 3.34-3.30 (m, 1H), 3.27-3.16 (m, 3H), 2.89 (dd, J=14.5, 6.0 Hz, 1H), 2.78 (s, 3H), 2.53-2.47 (m, 1H), 2.45 (s, 3H), 2.38-2.32 (m, 1H), 2.07 (s, 3H), 2.05-2.01 (m, 2H), 1.78-1.64 (m, 3H), 1.56-1.50 (m, 3H), 1.39-1.36 (m, 1H), 0.97 Hz, 3H), 0.80 (t, J=7.5 Hz, 3H); ESI MS m/z 857 [M+H]⁺.

Example 44

Preparation of 12'-(tert-Butoxycarbonylmethylsulfanyl)vinblastine Trifluoroacetate tert-Butyl thioglycolate (160 mg, 1.08 mmol), 12'-iodovinblastine (101 mg, 0.108 mmol), triethylamine (218 mg, 2.15 mmol), tris(dibenzylideneacetone)dipalladium(0) (9.8 mg, 0.011 mmol) and 1,1'bis(diphenylphosphino)ferrocene (24 mg, 0.043 mmol) were combined in N-methyl-2-pyrrolidinone (2.5 mL) and the reaction mixture was deoxygenated by bubbling argon through the solution for 30 min. The mixture was heated at 60° C. for 2 h then diluted with ethyl acetate (20 mL). The organic solution was washed with water (5 mL), saturated NaHCO₃ (5 mL) and brine (5 mL), dried over MgSO₄, and evaporated to dryness in vacuo. The residue was purified by reverse phase chromatography (C18, acetonitrile/water, 0.05% trifluoroacetic acid) to provide 12'-(tert-butoxycarbonylmethylsulfanyl)vinblastine trifluoroacetate (55 mg, 43%), which was a white powder after lyophilization: 1H NMR (500 MHz, CD₃OD) δ 9.80 (br s, 1H), 7.69 (s, 1H), 7.26 (m, 2H), 6.68 (s, 1H), 6.42 (s, 1H), 5.94 (dd, J=10.4, 4.2 Hz, 1H), 5.65 (d, J=10.4 Hz, 1H), 5.35 (s, 1H), 4.83 (m, 1H), 4.64 (dd, J=17.1, 11.2, 1H), 3.97-3.54 (m, 6H), 3.86 (s, 3H), 3.81 (s, 3H), 3.69 (s, 3H), 3.46 (m, 3H), 3.33 (m, 1H), 3.21 (m, 1H), 3.18 (s, 2H), 2.88 (m, 1H), 2.77 (s, 3H), 2.47 (dd, J=16.3, 4.7 Hz, 1H), 2.34 (m, 1H), 2.07 (s, 3H), 2.02 (m, 2H), 1.74 (m, 1H), 1.66 (m, 2H), 1.54 (m, 3H), 1.38 (s, 9H), 0.97 (t, J=7.4 Hz, 3H), 0.79 (t, J=7.2 Hz, 3H); ESI MS m/z 957 [M+H]⁺.

Example 45

Preparation of 12'-(Carboxymethylsulfanyl)vinblastine Trifluoroacetate

12'-tert-Butoxy carbonylmethylsulfanylvinblastine (26 mg, 0.022 mmol) was taken up in methylene chloride (1 mL) and cooled to 0° C. Trifluoroacetic acid (2 mL) was added dropwise and the reaction mixture was stirred at 0° C. for 20 min then at room temperature for 30 min. The reaction mixture was evaporated to dryness in vacuo and the residue was taken up in deionized water (1 mL) and lyophilized to provide 12'-(carboxymethylsulfanyl)vinblastine trifluoroacetate (25 mg, quantitative yield) as a white powder: 1H NMR (500 MHz, CD₃OD) δ 9.77 (br s, 1H), 7.71 (s, 1H), 7.28 (m, 2H), 6.69 (s, 1H), 6.42 (s, 1H), 5.94 (dd, J=10.3, 4.1 Hz, 1H), 5.65 (d, J=10.5 Hz, 1H), 5.35 (s, 1H), 4.82 (m, 1H), 4.65 (dd, J=16.1, 11.4 Hz, 1H), 3.96-3.44 (m, 8H), 3.86 (s, 3H), 3.81 (s, 3H), 3.69 (s, 3H), 3.33 (m, 1H), 3.24 (m, 2H), 3.18 (s, 2H), 2.88 (dd, J=14.6, 6.1 Hz, 1H), 2.77 (s, 3H), 2.57 (m, 1H), 2.34 (m, 1H), 2.07 (s, 3H), 2.04 (m, 2H), 1.72 (m, 1H), 1.65 (m, 2H), 1.53 (m, 3H), 1.37 (m, 1H), 0.97 (t, J=7.4 Hz, 3H), 0.79 (t, J=7.2 Hz, 3H); ESI MS m/z 901 [M+H]⁺.

Example 46

Preparation of 12'-(Methylaminocarbonylmethylsulfanyl)vinblastine Trifluoroacetate 12'-tert-Butoxy carbonylmethylsulfanylvinblastine (19 mg, 0.016 mmol) was taken up in methylene chloride (1 mL) and cooled to 0° C. Trifluoroacetic acid (2 mL) was added dropwise and the reaction mixture was stirred at 0° C. for 20 min then at room temperature for 30 min. The reaction mixture was evaporated to dryness in vacuo, taken up in DMF (1 mL), then HATU (9 mg, 0.024 mmol), methyl amine (40% aqueous, 14 µL, 0.16 mmol), and triethylamine (22 mL, 0.16 mmol) were added. Then reaction mixture was stirred under nitrogen for 24 h then the solvent was removed in vacuo. The residue was purified by reverse phase chromatography (C, 18, acetonitrile/water, 0.05% trifluoroacetic acid) to provide 12'-(methylaminocarbonylmethylsulfanyl)vinblastine trifluoroacetate (1.6 mg, 9%) as a white powder after lyophilization: ¹H NMR (500 MHz, CD₃OD) δ 9.75 (br s, 1H), 7.99 (br s, 1H), 7.68 (s, 1H), 7.24 (m, 2H), 6.63 (s, 1H), 6.41 (s, 1H), 5.93 (dd, J=9.8, 3.9 Hz, 1H), 5.60 (d, J=9.4 Hz, 1H), 5.35 (s, 1H), 4.86 (m, 1H), 4.62 (m, 1H), 3.96-3.54 (m, 6H), 3.85 (s, 3H), 3.81 (s, 3H), 3.68 (s, 3H), 3.51 (s, 2H), 3.37 (m, 1H), 3.18 (m, 3H), 3.08 (m, 1H), 2.87 (m, 1H), 2.77 (s, 3H), 2.69 (s, 3H), 2.47 (m, 1H), 2.31 (m, 1H), 2.07 (s, 3H), 1.98 (m, 2H), 1.72 (m, 1H), 1.66 (m, 2H), 1.52 (m, 3H), 1.31 (m, 1H), 0.97 (t, J=7.4 Hz, 3H), 0.78 (t, J=7.1 Hz, 3H); ESI MS m/z 914 [M+H]⁺.

Example 47

12'-(Methoxycarbonylethylsulfanyl)vincristine

12'-iodovincristine (200 mg, 0.210 mmol), 1,1'-bis(diphenylphosphino)ferrocene (47 mg, 0.085 mmol), tris(dibenzylideneacetone)dipalladium(0) (21 mg, 0.023 mmol), triethylamine (0.050 mL, 0.36 mmol), and methyl 3-mercaptopropionate (0.050 mL, 0.45 mmol) were combined in N-methylpyrrolidinone (4 mL) and heated at 60° C. under argon for 16 h. After cooling, the mixture was diluted with methylene chloride (10 mL) and washed with brine (10 mL). The aqueous layer was extracted with methylene chloride (2×10 mL), and the combined organic layers were dried (Na$_2$SO$_4$) and evaporated to dryness in vacuo. The residue was dissolved in ethyl acetate (50 mL), washed with water (3×20 mL) and brine (20 mL), dried over Na$_2$SO$_4$ and evaporated to dryness in vacuo. Purification by reverse phase chromatography (C, 18, methanol/water) gave 12'-(methoxycarbonylethylsulfanyl)vincristine (29.7 mg, 15%) as an off-white powder:

$^1$H NMR (300 MHz, CD$_3$OD) δ 8.93 (s, 1H), 7.83-7.15 (m, 4H), 6.93 (s, 1H), 5.89 (dd, J=9.7, 4.9 Hz, 1H), 5.41 (d, J=9.9 Hz, 1H), 5.15 (s, 1H), 4.58 (s, 1H), 4.15-3.94 (m, 2H), 3.90 (s, 3H), 3.67 (s, 3H), 3.63 (s, 6H), 3.39-3.23 (m, 6H), 3.07-3.01 (m, 4H), 2.90-2.72 (m, 3H), 2.62-2.52 (m, 3H), 2.43-2.27 (m, 2H), 2.11-1.95 (m, 4H), 1.80-1.76 (m, 1H), 1.52-1.37 (m, 3H), 1.32-1.29 (m, 3H), 0.89 (t, J=7.2 Hz, 3H), 0.78 (t, J=7.0 Hz, 3H); ESI MS m/z 943 [M+H]$^+$.

Example 48

12'-(2-(N,N-Dimethylamino)ethylsulfanyl)vinblastine Trifluoroacetate

To a mixture of 12'-iodovinblastine (47 mg, 0.05 mmol), tris(dibenzylideneacetone)-dipalladium(0) (4.6 mg, 0.005 mmol), 1,1'-bis(diphenylphosphino)ferrocene (11 mg, 0.02 mmol), triethylamine (28 µL, 0.2 mmol) and 1-methyl-2-pyrrolidinone (2 mL) was added 2-(dimethylamino) ethanethiol hydrochloride (14.2 mg, 0.1 mmol). After the addition was complete, the reaction mixture was deoxygenated with an argon purge and was then heated to 70° C. for 6 h. An additional 0.5 equivalents of all the reagents, except 12-iodovinblastine, were added to the reaction mixture at room temperature. The resulting mixture was deoxygenated again and then heated to 70° C. for an additional 20 h. The reaction mixture was cooled to room temperature, diluted with water and extracted with CH$_2$Cl$_2$ (2×20 mL). The combined organics were washed with water and brine, and then dried (MgSO$_4$). Purification by flash column chromatography (silica, 97:2:1 CH$_2$Cl$_2$/CH$_3$OH/Et$_3$N) followed by preparative TLC (silica, 2:3 CH$_2$Cl$_2$/CH$_3$OH) afforded 12'-(2-dimethylaminoethylsulfanyl)vinblastine as a tan solid (15 mg, 33%). The solid was dissolved in CH$_2$Cl$_2$ (1 mL) and treated with a drop of trifluoroacetic acid. The solution was evaporated to give the 12'-(2-(N,N-dimethylamino)ethylsulfanyl)vinblastine trifluoroacetate (15 mg, 73%): $^1$H NMR (300 MHz, CD$_3$OD) δ 9.84 (s, 1H), 7.67 (s, 1H), 7.22 (s, 2H), 6.61 (s, 1H), 6.33 (s, 1H), 5.84 (dd, J=10.5, 3.9 Hz, 1H), 5.58, (d, J=10.5 Hz, 1H), 5.26 (s, 1H), 4.60-4.54 (m, 1H), 3.89-3.81 (m, 3H), 3.76 (s, 3H), 3.72 (s, 3H), 3.70 (s, 2H), 3.63 (s, 2H), 3.58 (s, 3H), 3.44-3.37 (m, 2H), 3.14-3.09 (m, 5H), 3.03-2.96 (m, 1H), 2.85 (s, 2H), 2.83-2.79 (m, 2H), 2.77 (s, 6H), 2.69 (s, 3H), 2.38-2.33 (m, 1H), 2.33-2.25 (m, 1H), 1.98-1.89 (m, 1H), 1.98 (s, 3H), 1.69-1.61 (m, 1H), 1.57-1.56 (m, 2H), 1.51-1.40 (m, 3H), 0.88 (t, J=7.3 Hz, 3H), 0.67 (t, J=7.1 Hz, 3H); ESI MS m/z 914 [M+H]$^+$.

Example 49

Preparation of 12'-[3-(Morpholin-4-yl)propylsulfanyl]vinblastine Trifluoroacetate A mixture of 12'-(3-mesyloxypropylsulfanyl)vinblastine (75 mg, 0.077 mmol) and morpholine (33.4 µL, 0.38 mmol) in THF (2 mL) was heated to reflux for 24 h and then cooled to room temperature. The reaction mixture was diluted with water and extracted with CH$_2$Cl$_2$ (2×20 mL). The combined organics were washed with water and brine, and then dried (MgSO$_4$). Purification by column chromatography (silica, 9:1 CH$_2$Cl$_2$/CH$_3$OH) followed by preparative TLC (silica, 4:1 CH$_2$Cl$_2$/CH$_3$OH) gave 12'-[3-(morpholin-4-ylpropylsulfanyl]vinblastine as a solid (29 mg, 39%). The solid was dissolved in CH$_2$Cl$_2$ (1 mL) and treated with a drop of trifluoroacetic acid. The solution was evaporated to give 12'-[3-(morpholin-4-yl)propylsulfanyl]vinblastine trifluoroacetate (33.4 mg, 87%): $^1$H NMR (300 MHz, CD$_3$OD) δ 9.83 (s, 1H), 7.71 (s, 1H), 7.29 (s, 2H), 6.73 (s, 1H), 6.44 (s, 1H), 5.96 (dd, J=10.1, 4.5 Hz, 1H), 5.68, (d, J=10.4 Hz, 1H), 5.37 (s, 1H), 4.74-4.60 (m, 1H), 4.05-3.67 (m, 13H), 3.87 (s, 3H), 3.83 (s, 3H), 3.70 (s, 3H), 3.58-3.05 (m, 11H), 2.96 (t, J=6.7 Hz, 2H), 2.80 (s, 3H), 2.50-2.29 (m, 2H), 2.09 (s, 3H), 2.08-1.96 (m, 3H), 1.80-1.67 (m, 3H), 1.61-1.51 (m, 3H), 1.39-1.37 (m, 1H), 0.99 (t, J=7.3 Hz, 3H), 0.81 (t, J=7.0 Hz, 3H); ESI MS m/z 970 [M+H]$^+$.

Example 50

Preparation of 12'-[3-(Piperidin-1-yl)propylsulfanyl] vinblastine Trifluoroacetate A mixture of 12'-(3-mesyloxypropylsulfanyl)vinblastine (100 mg, 0.102 mmol) and piperidine (51 µL, 0.51 mmol) in THF (3 mL) was heated to reflux for 72 h and then cooled to room temperature. The reaction mixture was diluted with water and extracted with CH$_2$Cl$_2$ (2×20 mL). The combined organics were washed with water and brine, and then dried (MgSO$_4$). Purification by preparative TLC (silica, 4:1 acetone/CH$_3$OH) followed by ion exchange chromatography (Isolute SCX-2 column, 3:1 MeOH/NH$_4$OH) gave 12'-[3-(piperidin-1-yl)propylsulfanyl]vinblastine as a solid (37 mg, 37%). The solid was dissolved in CH$_2$Cl$_2$ (1 mL) and treated with a drop of trifluoroacetic acid. The solution was evaporated to give 12'-[3-(piperidin-1-yl)propylsulfanyl]vinblastine trifluoroacetate (45 mg, 90%): $^1$H NMR (300 MHz, CD$_3$OD) δ 9.84 (s, 1H), 7.70 (s, 1H), 7.29 (s, 2H), 6.73 (s, 1H), 6.44 (s, 1H), 5.96 (dd, J=10.4, 4.3 Hz, 1H), 5.68, (d, J=10.4 Hz, 1H), 5.37 (s, 1H), 4.74-4.60 (m, 1H), 4.01-3.91 (m, 3H), 3.87 (s, 3H), 3.83 (s, 3H), 3.75 (s, 1H), 3.70 (s, 3H), 3.68-3.63 (m, 1H), 3.56-3.40 (m, 4H), 3.28-3.05 (m, 4H), 2.98-2.87 (m, 5H), 2.80 (s, 3H), 2.53-2.30 (m, 2H), 2.09 (s, 3H), 2.08-1.32 (m, 20H), 0.99 (t, J=7.3 Hz, 3H), 0.82 (t, J=7.2 Hz, 3H); ESI MS m/z 968 [M+H]$^+$.

Example 51

Preparation of 12'-[2-Pyrrolidin-1-yl-ethylsulfanyl] vinblastine Trifluoroacetate To a mixture of 12'-iodovinblastine (176 mg, 0.17 mmol), tris(dibenzylideneacetone)dipalladium(0) (15 mg, 0.016 mmol), 1,1'-bis(diphenylphosphino)ferrocene (18 mg, 0.030 mmol), triethylamine (81 µL, 0.59 mmol) and 1-methyl-2-pyrrolidinone (2 mL) was added 2-pyrrolidin-1-yl-ethanethiol (28 mg, 0.50 mmol). After the addition was complete, the reaction mixture was deoxygenated with an argon purge and was then heated to 70° C. for 16 h. After cooling to room temperature, the reaction mixture was diluted with water and extracted with EtOAc (2×20 mL). The combined organics were washed with H$_2$O and brine, and then dried (Na$_2$SO$_4$) and concentrated. Purification by reverse phase chromatography (C18, acetonitrile/water, 0.05% trifluoroacetic acid) gave 12'-(2-pyrrolidin-1-yl-ethylsulfanyl)vinblastine trifluoroacetate (33 mg, 21%): $^1$H NMR (500 MHz, CD$_3$OD) δ 9.93 (m, 1H), 7.75 (s, 1H), 7.31 (s, 2H), 6.71 (s, 1H), 6.42 (s, 1H), 5.93 (dd, J=10.5, 3.0 Hz, 1H), 5.67 (dd, J=10.5, 3.0 Hz, 1H), 5.35 (s, 1H), 4.70-4.67 (m, 1H), 3.97-3.90 (m, 3H), 3.84 (s, 3H), 3.82-3.80 (m, 4H), 3.75-3.72 (m, 2H), 3.69-3.62 (m, 7H), 3.52-3.48 (m, 1H), 3.36-3.27 (m, 3H), 3.19-3.16 (m, 4H), 3.06-3.02 (m, 2H), 2.89 (d, J=14.5, 6.0 Hz, 1H), 2.77 (s, 3H), 2.48-2.44 (m, 1H), 2.37-2.32 (m, 1H), 2.11-1.98 (m, 6H), 2.07 (s, 3H), 1.77-1.72 (m, 1H), 1.65 (d, J=4.0 Hz, 2H), 1.59-1.50 (m, 3H), 1.40-1.36 (m, 1H), 0.97 (t, J=7.5 Hz, 3H), 0.79 (t, J=7.5 Hz, 3H); ESI MS m/z 940 [M+H]$^+$.

Example 52

Preparation of 12'-[2-(Acetylamino)ethylsulfanyl] vinblastine Trifluoroacetate

To a mixture of 12'-iodovinblastine (39 mg, 0.04 mmol), tris(dibenzylideneacetone)dipalladium(0) (3.6 mg, 0.004 mmol), 1,1'-bis(diphenylphosphino)ferrocene (9.1 mg, 0.016 mmol), triethylamine (12 μL, 0.08 mmol) and 1-methyl-2-pyrrolidinone (1 mL) was added N-(2-mercaptoethyl)acetamide (9 μL, 0.08 mmol). After the addition was complete, the reaction mixture was deoxygenated with an argon purge and was then heated to 70° C. for 2 h and then cooled to room temperature. The reaction mixture was diluted with water and extracted with CH$_2$Cl$_2$ (2×20 mL). The combined organics were washed with H$_2$O and brine, and then dried (MgSO$_4$). Purification by preparative TLC (silica, 92.5:7.5 CH$_2$Cl$_2$/CH$_3$OH) gave an orange solid. The solid was further purified by prep-TLC (silica gel, CH$_3$OH/acetone, 4:1) to afford 12'-[2-(acetylamino)ethylsulfanyl]vinblastine as off-white solid (19 mg, 50%). The solid was dissolved in CH$_2$Cl$_2$ (1 mL) and treated with a drop of trifluoroacetic acid. The solution was evaporated to give 12'-[2-acetylaminoethylsulfanyl]vinblastine trifluoroacetate (19 mg, 80%): $^1$H NMR (300 MHz, CD$_3$OD) δ 9.75 (s, 1H), 7.72 (s, 1H), 7.27 (s, 2H), 6.72 (s, 1H), 6.44 (s, 1H), 5.96 (dd, J=10.4, 4.3 Hz, 1H), 5.68, (d, J=10.4 Hz, 1H), 5.38 (s, 1H), 4.70-4.61 (m, 1H), 3.98-3.64 (m, 8H), 3.87 (s, 3H), 3.84 (s, 3H), 3.71 (s, 3H), 3.60-3.48 (m, 1H), 3.44-3.25 (m, 1H), 3.21 (s, 2H), 2.95 (t, J=6.9 Hz, 3H), 2.80 (s, 3H), 2.48 (dd, J=6.2, 4.5 Hz, 1H), 2.42-2.32 (m, 1H), 2.09 (s, 3H), 2.05-1.99 (m, 1H), 1.93 (s, 3H), 1.81-1.68 (m, 3H), 1.61-1.48 (m, 3H), 1.42-1.25 (m, 4H), 0.99 (t, J=7.5 Hz, 3H), 0.82 (t, J=7.2 Hz, 3H); ESI MS m/z 928 [M+H]$^+$.

Example 53

Preparation of 12'-Thiovinblastine Trifluoroacetate

12'-Iodovinblastine (60 mg, 0.064 mmol), thiotriisopropylsilyl potassium salt (44 mg, 0.192 mmol), and tetrakis(triphenylphosphine) palldium(0) (15 mg, 0.012 mmol) were combined in benzene/tetrahydrofuran (4 mL, 3:1) and the reaction mixture was deoxygenated by bubbling argon through the solution for 30 min. The mixture was heated at 65° C. for 1.5 h then diluted with ethyl acetate (15 mL). The organic solution was washed with water (5 mL), saturated aqueous NaHCO$_3$ (5 mL) and brine (5 mL), dried over MgSO$_4$, and evaporated to dryness in vacuo. The residue was purified by reverse phase chromatography (C18, acetonitrile/water, 0.05% trifluoroacetic acid) to provide 12'thiovinblastine trifluoroacetate (18.9 mg, 28%) which was a white powder after lyophilization: $^1$H NMR (500 MHz, CD$_3$OD) δ 9.62 (br s, 1H), 7.51 (s, 1H), 7.18 (d, J=8.4 Hz, 1H), 7.10 (dd, J=8.4, 1. Hz, 1H), 6.64 (s, 1H), 6.41 (s, 1H), 5.94 (dd, J=10.3, 4.0 Hz, 1H), 5.63 (d, J=10.5 Hz, 1H), 5.35 (s, 1H), 4.84 (m, 1H), 4.61 (dd, J=16.6, 11.2 Hz, 1H), 3.95-3.56 (m, 7H), 3.85 (s, 3H), 3.81 (s, 3H), 3.69 (s, 3H), 3.44 (m, 2H), 3.27 (m, 1H), 3.18 (m, 3H), 2.88 (dd, J=14.2, 6.0 Hz, 1H), 2.77 (s, 3H), 2.47 (dd, J=15.8, 4.3 Hz, 1H), 2.34 (m, 1H), 2.07 (s, 3H), 2.04 (m, 1H), 1.78-1.62 (m, 3H), 1.52 (q, J=7.6 Hz, 2H), 1.38 (m, 1H), 0.96 (t, J=7.4 Hz, 3H), 0.79 (t, J=7.3 Hz, 3H); ESI MS m/z 843 [M+H]$^+$.

Example 54

12'-(3-Hydroxyphenylsulfanyl)vincristine

A solution of 12'-iodovincristine (158 mg, 0.17 mmol), tris(dibenzylideneacetone)dipalladium(0) (18 mg, 0.02 mmol), triethylamine (0.05 mL) in N-methylpyrrolidine (4 mL) was deoxygenated with argon for 10 min, then 3-hydroxythiophenol (0.05 mL) was added and the reaction mixture was heated to 60° C. overnight. After this time, additional tris(dibenzylideneacetone)dipalladium(0) (15 mg) was added and heating was continued for another 24 h. The reaction mixture was cooled to room temperature and diluted with CH$_2$Cl$_2$. The organic layer was washed with brine, dried (sodium sulfate), filtered, and concentrated under reduced pressure to give a dark brown solid. Purification by flash column chromatography (silica, 94.5:5:0.5 CH$_2$Cl$_2$/MeOH/NH$_4$OH) followed by reverse phase chromatography (C18, MeOH/water) gave 12'-(3-hydroxyphenylsulfide)vincristine (2.8 mg, 2%) as an off-white solid: 1H NMR (300 MHz, CD$_3$OD) δ 8.94 (s, 1H), 7.78 (s, 1H), 7.30 (d, J=8 Hz, 1H), 7.22 (s, 1H), 7.20 (d, J=8 Hz, 1H), 7.00 (t, J=8 Hz, 1H), 6.94 (s, 1H), 6.53 (d, J=8 Hz, 1H), 6.48 (d, J=8 Hz, 1H), 6.45 (s, 1H), 5.91 (dd, J=10, 5 Hz, 1H), 5.43 (d, J=10 Hz, 1H), 5.16 (s, 1H), 4.58 (s, 1H), 4.10 (t, J=15 Hz, 1H), 4.00 (m, 1H), 3.90 (s, 3H), 3.87 (s, 1H), 3.72 (s. 1H), 3.69 (s, 3H), 3.63 (s, 3H), 3.47-3.13 (m), 3.09 (s, 1H), 3.04 (m, 1H), 2.90 (d, J=17 Hz, 1H), 2.81 (m, 2H), 2.67 (tm, J=10 Hz, 1H), 2.44 (d, J=11 Hz, 1H), 2.30 (d, J=11 Hz, 1H), 2.09 (m, 1H), 2.03 (s, 3H), 1.75 (m, 1H), 1.60-1.48 (m, 3H), 1.34 (q, J=7 Hz, 2H), 0.89 (t, J=7 Hz, 3H), 0.79 (t, J=7 Hz, 3H); ESI MS m/z 949 [M+H]$^+$.

Example 55

Preparation of 12'-(2-Hydroxyphenylsulfanyl)vinblastine

A solution of iodovinblastine (200 mg, 0.214 mmol), 1,1'bis(diphenylphosphino)ferrocene (48 mg, 0.09 mmol), tris(dibenzylideneacetone)dipalladium(0) (20 mg, 0.02 mmol), and triethylamine (47 μL, 0.43 mmol) in NMP (3.2 mL) was deoxygenated with argon for 10 min, then 2-hydroxythiophenol (44.3 μL, 0.428 mmol) was added and the reaction mixture was heated to 60° C. for 22 h. The reaction mixture was cooled to room temperature and then partitioned between methylene chloride and brine. The organic layer was concentrated under rlittle bearballs educed pressure and the resulting residue was purified by chromatography (silica, 85:15 CH$_2$Cl$_2$/MeOH). Further purification by reverse phase chromatography (C18, acetonitrile/water, 0.05% concentrated ammonium hydroxide) gave 12'-(2-hydroxyphenylsulfanyl)vinblastine (28 mg, 8%) as a white solid: 1H NMR (300 MHz, DMSO-d$_6$) δ 7.76 (s, 1H), 7.38 (d, J=8 Hz, 1H), 7.13 (d, J=8 Hz, 1H), 6.97 (td, J=7, 2 Hz, 1H), 6.82 (d, J=8 Hz, 1H), 6.67 (m, 3H), 6.42 (s, 1H), 5.83 (dd, J=10, 4 Hz, 1H), 5.40 (m, 1H), 5.12 (s, 2H), 4.37 (m, 1H), 3.90 (s, 3H), 3.82 (t, J=15 Hz, 1H), 3.80-3.20 (m), 3.78 (s, 3H), 3.71 (s, 3H), 3.01 (m, 2H), 2.65 (m, 1H), 2.64 (s, 3H), 2.20 (m, 2H), 2.02 (m, 1H), 2.01 (s, 3H), 1.73 (m, 1H), 1.68-1.30 (m, 5H), 1.15 (m, 1H), 0.85 (t, J=7 Hz, 3H), 0.65 (t, J=7 Hz, 3H); ESI MS m/z 935 [M+H]$^+$.

Example 56

Preparation of 12'-(2-Chlorophenylsulfanyl)vincristine Trifluoroacetate

A solution of 12'-iodovincristine (60 mg, 0.05 mmol) in NMP (1.5 mL) was deoxygenated with argon for 10 minutes. The reaction vessel was charged with 1,1'-bis(diphenylphosphino)ferrocene (20 mg, 0.035 mmol), tris(dibenzylideneacetone)dipalladium(0) (9 mg, 0.009 mmol) and Et$_3$N (13 mg, 0.13 mmol). The mixture was stirred for 20 min at room temperature, 2-chlorobenzene-thiol (15 mg, 0.105 mmol) was added and then stirred at 60° C. overnight. The mixture was cooled to room temperature, diluted with ethyl acetate (100 mL) and washed with saturated aqueous NH$_4$Cl (3×10 mL) and brine (3×10 mL). The organic layer was dried (Na$_2$SO$_4$), filtered and concentrated. The residue was purified by flash chromatography (silica, 10:1 CH$_2$Cl$_2$/MeOH) and then by reverse phase chromatography (C-18, acetonitrile/water, 0.05% trifluoroacetic acid) to give 11'-(2-chlorophenylsulfanyl)vincristinel (8 mg, 35%) trifluoroacetate: 1H NMR (500 MHz, CD$_3$OD) δ 10.25 (s, 1H), 9.00 (s, 1H), 7.81 (s, 1H), 7.44 (d, J=8.5 Hz, 1H), 7.36 (s, 1H), 7.34 (dd, J=7.5, 1.0 Hz, 1H), 7.28 (dd, J=8.5, 1.5 Hz, 1H), 7.07-6.99 (m, 3H), 6.66 (dd, J=8.0, 1.5 Hz, 1H), 5.99 (dd, J=10.0, 4.5 Hz, 1H), 5.75 (d, J=10.5 Hz, 1H), 5.21 (s, 1H), 4.69 (t, J=11.5 Hz, 2H), 4.14 (s, 1H), 4.02-3.98 (m, 2H), 3.96 (s, 3H), 3.92-3.82 (m, 2H), 3.75 (s, 3H), 3.68 (s, 3H), 3.64-3.54 (m, 3H), 3.38-3.33 (m, 2H), 3.16 (s, 2H), 2.88 (dd, J=14.5, 6.0 Hz, 1H), 2.50 (d, J=12.0 Hz, 1H), 2.43-2.38 (m, 1H), 2.05 (s, 3H), 2.01-1.96 (m, 1H), 1.68-1.55 (m, 4H), 1.51 (q, J=7.5 Hz, 2H), 1.33-1.31 (m, 1H), 0.96 (t, J=7.5 Hz, 3H), 0.84 (t, J=7.0 Hz, 3H); ESI MS m/z 967 [M+H]$^+$.

Example 57

Preparation of 12'-(Methyldisulfanyl)vinblastine Trifluoroacetate

12'-sulfanylvniblastine (26 mg, 0.031 mmol) and N-(methylthio)phthalimide (12 mg, 0.062 mmol) were combine in benzene (1 ml)under nitrogen at room temperature. After stirring for 45 min, the solvent was removed in vacuo and the residue was purified by reverse phase chromatography (C18, acetonitrile/water, 0.05% trifluoroacetic acid) to provide 12'-(methyldisulfanyl)vinblastine as a salt of thrifluoroacetic acid (11.9 mg, 35%) which was a white powder after lyophilization: $^1$H NMR (500 MHz, CD$_3$OD) δ 9.86 (br s, 1H), 7.74 (s, 1H), 7.34 (dd, J=8.5, 1.5 Hz, 1H), 7.30 (d, J=8.5 Hz, 1H), 6.69 (s, 1H), 6.42 (s, 1H), 5.94 (dd, J=10.4, 5.3 Hz, 1H), 5.66 (d, J=10.5 Hz, 1H), 5.35 (s, 1H), 4.96-3.61 (m, 7H), 4.84 (m, 1H), 4.66 (dd, J=17.2, 11.1 Hz, 1H), 3.86 (s, 3H), 3.81 (s, 3H), 3.70 (s, 3H), 3.49 (d, J=15.8 Hz, 1H), 3.34 (m, 1H), 3.24 (m, 1H), 3.18 (s, 1H), 2.87 (dd, J=14.4, 6.1 Hz, 1H), 2.78 (s, 3H), 2.47 (m, 1H), 2.41 (s, 3H), 2.34 (m, 1H), 2.07 (s, 3H), 2.03 (m, 2H), 1.73 (m, 1H), 1.65 (m, 2H), 1.57 (m, 1H), 1.52 (q, J=7.6 Hz, 2H), 1.38 (m, 1H), 0.97 (t, J=7.4 Hz, 3H), 0.81 (t, J=7.2 Hz, 3H); ESI MS m/z 889 [M+H]$^+$.

Example 58

Preparation of 12'-(Isopropyldisulfanyl)vinblastine Trifluoroacetate

12'-sulfanylvinblastine (17 mg, 0.020 mmol) and diethyl N-isopropylsulfenylhydrazodicarboxylate (15 mg, 0.060 mmol) were combined in benzene (1 ml)under nitrogen and stirred at room temperature for 5 h then at 50° C. overnight. The solvent was removed in vacuo and the non basic impurities were removed by flushing the residue through an Absolute SCX-2 column, first with methanol then with 10% aqueous ammonium hydroxide/methanol. The basic methanol fractions were evaporated in vacuo and the residue was purified by reverse phase chromatography (C18, acetonitrile/water, 0.05% trifluoroacetic acid) to provide di(12'-vinblastine) disulfide trifluoroacetate (11.5 mg, 51%) and 12'-(isopropyldisulfanyl)vinblastine (3.0 mg, 13%) as white powders after lyophilization. The data for the trifluoroacetate of 12'-isopropyldisulfanylvinblastine is as follows:

$^1$H NMR (500 MHz, CD$_3$OD) δ 7.73 (s, 1H), 7.34 (d, J=8.4 Hz, 1H), 7.27 (d, J=8.4 Hz, 1H), 6.64 (s, 1H), 6.41 (s, 1H), 5.93 (dd, J=10.7, 5.2 Hz, 1H), 5.59 (d, J=9.5 Hz, 1H), 5.35 (s, 1H), 4.86 (m, 1H), 4.62 (m, 1H), 3.96-3.57 (m, 6H), 3.85 (s, 3H), 3.81 (s, 3H), 3.69 (s, 3H), 3.34 (m, 2H), 3.18 (m, 3H), 3.04 (m, 1H), 2.90 (m, 1H), 2.77 (s, 3H), 2.71 (m, 1H), 2.49 (dd, J=12.5, 6.2 Hz, 1H), 2.28 (m, 1H), 2.07 (s, 3H), 2.06 (m, 1H), 1.96 (m, 1H), 1.74 (m, 1H), 1.66 (m, 2H), 1.52 (m, 3H), 1.38 (m, 1H), 1.28 (d, J=6.7 Hz, 6H), 0.97 (t, J=7.2 Hz, 3H), 0.79 (t, J=7.3 Hz, 3H); ESI MS m/z 917 [M+H]$^+$.

Example 59

Preparation of 12'-(tert-Butyldisulfanyl)vinblastine Trifluoroacetate

12'-sulfanylvinblastine (19 mg, 0.023 mmol) and diethyl N-tert-butylsulfenylhydrazodicarboxylate (12 mg, 0.045 mmol) were combined in benzene (1 ml)under nitrogen and stirred at 50° C. overnight. Additional diethyl N-tert-butylsulfenylhydrazodicarboxylate (30 mg, 0.113 mmol) was added and the reaction mixture was kept at 50° C. for 4 d. The solvent was removed in vacuo and the non-basic impurities were removed by flushing the residue through an Absolute SCX-2 column, first with methanol then with 10% aqueous ammonium hydroxide/methanol. The basic methanol fractions were evaporated in vacuo and the residue was purified by reverse phase chromatography (C18, acetonitrile/water, 0.05% trifluroacetic acid) to provide di(12'-vinblastine)disulfide as a triacetic acid salt (6.2 mg, 33%) and 12'-(tert-butyldisulfanyl)vinblastine as a trifluoroacetic acid salt(1.9 mg, 7.3%). The data for the trifluoroacetate of 12'-(tert-butyldisulfanyl)vinblastine is as follows: $^1$H NMR (500 MHz, CD$_3$OD) δ 9.77 (br s, 1H), 7.73 (s, 1H), 7.36 (dd, J=8.5, 1.6 Hz, 1H), 7.25 (d, J=8.5 Hz, 1H), 6.68 (s, 1H), 6.42 (s, 1H), 5.94 (dd, J=10.5, 4.4 Hz, 1H), 5.64 (d, J=9.5 Hz, 1H), 5.36 (s, 1H), 4.84 (m, 1H), 4.63 (dd, J=16.7, 10.5 Hz, 1H), 3.97-3.55 (m, 7H), 3.86 (s, 3H), 3.81 (s, 3H), 3.69 (s, 3H), 3.45 (m, 1H), 3.39 (m, 1H), 3.18 (m, 3H), 2.89 (dd, J=14.5, 5.7 Hz, 1H), 2.78 (s, 3H), 2.45 (m, 1H), 2.34 (m, 1H), 2.07 (s, 3H), 2.00 (m, 1H), 1.74 (m, 1H), 1.66 (m, 2H), 1.56 (m, 1H), 1.52 (q, J=7.6 Hz, 2H), 1.38 (m, 1H), 1.29 (s, 9H), 0.97 (t, J=7.4 Hz, 3H), 0.79 (t, J=7.3 Hz, 3H); ESI MS m/z 931 [M+H]$^+$.

Example 60

Preparation of Di-(12'-vinblastine)disulfide Trifluoroacetate

12'-sulfanylvinblastine (17 mg, 0.020 mmol) and diethyl N-isopropylsulfenylhydrazodicarboxylate (15 mg, 0.060 mmol) were combined in benzene (1 ml)under nitrogen and stirred at room temperature for 5 h then at 50° C. overnight. The solvent was removed in vacuo and the non-basic impurities were removed by flushing the residue through an Absolute SCX-2 column, first with methanol then with 10% aqueous ammonium hydroxide/methanol. The basic methanol fractions were evaporated in vacuo and the residue was purified by reverse phase chromatography (C18, acetonitrile/water, 0.05% trifluoroacetic acid) to provide di(12'-vinblastine) disulfide trifluoroacetate (11.5 mg, 51%) and 12'-isopropyldisulfanylvinblastine as a salt of trifluoroacetic acid (3.0 mg, 13% yield. The data for the trifluoroacetate of di-(12'-vinblastine)disulfide is as follows: $^1$H NMR (500 MHz, CD$_3$OD) δ 10.00 (br s, 2H), 7.47 (s, 2H), 7.26 (m, 4H), 6.71 (s, 2H), 6.42 (s, 2H), 5.96 (dd, J=11.5, 5.3 Hz, 2H), 5.67 (d, J=10.5 Hz, 2H), 5.35 (s, 2H), 4.85 (m, 2H), 4.62 (dd, J=16.1, 11.0, 2H), 3.97-3.68 (m, 10H), 3.86 (s, 6H), 3.81 (s, 6H), 3.73 (s, 6H), 3.48 (m, 6H), 3.28-3.08 (m, 8H), 2.88 (dd, J=14.6, 6.3 Hz, 2H), 2.78 (s, 6H), 2.46 (dd, J=16.1, 4.7 Hz, 2H), 2.34 (m, 2H), 2.08 (s, 6H), 2.01 (m, 2H), 1.72 (m, 2H), 1.66 (m, 4H), 1.58 (m, 2H), 1.53 (q, J=7.4 Hz, 4H), 1.38 (m, 2H), 1.00 (t, J=7.4 Hz, 6H), 0.78 (t, J=7.2 Hz, 6H); ESI MS m/z 1683 [M+H]$^+$.

Example 61

Preparation of 12'-Formylvinblastine Trifluoroacetate

Vinblastine (55 mg, 0.068 mmole) in trifluoroacetic acid (12 mL) was added via pipet to solid hexamethylenetetramine (114 mg, 0.814 mmol) then heated to reflux for 20 min. After cooling to room temperature the reaction mixture was added carefully to a magnetically stirred solution of saturated aqueous NaHCO$_3$ water (1:1, 100 mL). Solid NaHCO$_3$ was then added carefully in small portions until no gas evolution was noted. The mixture was extracted with chloroform (3×25 mL) and the combined organic extracts were washed with brine (25 mL), dried over MgSO$_4$, then evaporated to dryness in vacuo. The residue was purified by reverse phase chromatography (C18, acetonitrile/water, 0.05% trifluoroacetic acid) to provide 12'-formylvinblastine trifluoroacetate (28 mg, 40%): $^1$H NMR (500 MHz, CD$_3$OD) δ 9.95 (s, 1H), 9.66 (s, 1H), 7.59 (s, 1H), 7.28 (d, J=8.4 Hz, 1H), 7.20 (d, J=8.3 Hz, 1H), 6.72 (s, 1H), 6.42 (s, 1H), 5.94 (dd, J=10.5, 5 Hz, 1H), 5.66 (d, J=10. Hz, 1H), 5.43 (s, 1H), 5.36 (s, 1H), 4.66 (dd, J=17.4, 11.2, 1H), 3.97-3.59 (m, 6H), 3.86 (s, 3H), 3.82 (s, 3H), 3.69 (s, 3H), 3.48 (d, J=15.8 Hz, 1H), 3.33 (m, 1H), 3.20 (m, 3H), 2.89 (dd, J=14.3, 6.2 Hz, 1H), 2.78 (s, 3H), 2.47 (dd, J=16.2, 5.0 Hz, 1H), 2.35 (m, 1H), 2.07 (s, 3H), 2.03 (m, 2H), 1.75 (m, 1H), 1.66 (m, 2H), 1.52 (m, 3H), 1.39 (m, 1H), 0.97 (t, J=7.4 Hz, 3H), 0.81 (t, J=7.2 Hz, 3H); ESI MS m/z 839 [M+H]$^+$.

Example 62

Preparation of 12'-Formylvincristine Trifluoroacetate solution of 12'-iodovincristine (58 mg, 0.062 mmole) in THF (1 mL) was deoxygenated with argon for 3 minutes. The reaction vessel was charged with tetrakis(triphenylphosphine)palladium(0) (1 mg, 0.011 mmol), and the flask was sealed with a septum. CO gas (1 atm, balloon) was bubbled into the solution for 1 minute to generate a saturated solution and to establish a CO atmosphere in the flask. The reaction mixture was heated to 50° C., and stirred as a solution of tri-n-butyltin hydride (18 µl, 0.068 mmol) in deoxygenated THF (0.5 mL) was slowly added over 30 minutes (syringe pump). After the addition was complete, the mixture was stirred another 15 minutes at 50° C., and then the reaction's porgress was checked by ESI mass spectral analysis. Starting material was observed by ESI MS therefore another 8 µl of tri-n-butyltin hydride in deoxygenated THF (0.5 mL) was added over 15 min. After 30 min, no starting material remained by ESI mass. The reaction mixture was cool to room temperature, diluted with diethyl ether (75 mL), and washed with 1 N HCl (3×25 mL). The combined aqueous washes were back-extracted with diethyl ether (25 mL). The acidic water layer was partially neutralized with saturated aqueous NaHCO$_3$ (10 mL), and the resulting turbid mixture was extracted with EtOAc (3×25 mL). The combined organic extracts were dried (Na$_2$SO$_4$) and concentrated. The residue was purified by reverse phase chromatography (C18, acetonitrile/water, 0.05% trifluoroacetic acid) to provide 12'-formylvincristine trifluoroacetate (16 mg, 30%): $^1$H NMR (500 MHz, CD$_3$OD) δ 9.93 (br s, 1H), 8.97 (s, 1H), 7.59 (s, 1H), 7.35-7.32 (m, 2H), 7.22-7.19 (m, 1H), 6.99 (s, 1H), 5.98-5.95 (m, 1H), 5.75-5.72 (m, 1H), 5.43 (s, 1H), 5.16 (s, 1H), 4.71-4.66 (m, 2H), 4.04-3.88 (m, 5H), 3.85-3.67 (m, 7H), 3.63-3.57 (m, 1H), 3.52-3.45 (m, 1H), 3.23-3.15 (m, 2H), 2.88-2.84 (m, 1H), 2.54-2.49 (m, 1H), 2.43-2.38 (m, 1H), 2.08-2.03 (m, 8H), 1.99-1.94 (m, 1H), 1.69-1.62 (m, 3H), 1.55-1.49 (m, 3H), 1.35-1.30 (m, 1H), 0.97 (t, J=7.5 Hz, 3H), 083 (t, J=7.0 Hz, 3H); ESI MS m/z 853 [M+H]$^+$.

Example 63

Preparation of 12'-(Hydroxymethyl)vinblastine

An ice-cold solution of 12'-formylvinblastine (25 mg, 0.030 mmol) in THF (1 mL) was treated with lithium tri-tert-butoxyaluminum hydride (11 mg, 0.045 mmol). The resulting mixture was allowed to warm to room temperature, and after stirring for two hours, the reaction was checked by ESI mass spectral analysis. The reaction was treated again with lithium tri-tert-butoxyaluminum hydride (2×15 mg) over a 20 hour period. The reaction was then quenched with saturated aqueous ammonium chloride (5 mL), diluted with water (7 mL) and extracted with methylene chloride (3×10 mL). The combined extracts were dried (Na$_2$SO$_4$) and concentrated to a white solid. Purification by preparative TLC (silica, 7:3 EtOAc/hexanes) followed by lyophilization from acetonitrile and water gave 12'-(Hydroxymethyl)vinblastine (15 mg, 60%) as a white solid: 1H NMR (500 MHz, CDCl$_3$) δ 9.80 (s, 1H), 8.05 (s, 1H), 7.51 (s, 1H), 7.18 (dd, J=1.2, 8.6 Hz, 1H), 7.10 (d, J=4.3 Hz, 1H), 6.59 (s, 1H), 6.10 (s, 1H), 5.85 (dd, J=10.1, 3.7 Hz, 1H), 5.46 (s, 1H), 5.30 (d, J=10.2 Hz, 1H), 4.77 (s, 2H), 3.95 (t, J=14.2 Hz, 1H), 3.79 (s, 6H), 3.85-3.67 (m, 1H), 3.61 (s, 3H), 3.47-3.23 (m, 4H), 3.20-3.05 (m, 2H), 2.90-2.77 (m, 3H), 2.71 (s, 3H), 2.65 (s, 1H), 2.52-2.36 (m, 2H), 2.29 (d, J=12.4 Hz, 1H), 2.19-2.13 (m, 1H), 2.10 (s, 3H), 1.91-1.55 (m, 5H), 1.52-1.18 (m, 6H), 0.89 (t, J=7.5 Hz, 3H), 0.80 (t, J=7.2 Hz, 3H); ESI MS m/z 841 [M+H]$^+$.

Example 64

Preparation of 12'-(N-Isopropylaminomethyl)vinblastine Trifluoroacetate

A solution of 12'-formylvinblastine (30 mg, 0.036 mmol) in 1,2-dichloroethane (1 mL) was treated with isopropylamine (4.2 mg, 0.072 mmol) and sodium triacetoxyborohydride (15 mg, 0.072 mmol). The resulting mixture was stirred at room temperature, until ESI mass spectral analysis indicated no starting material remained. The reaction was quenched with saturated aqueous sodium bicarbonate (5 mL), and the resulting mixture was extracted with methylene chloride (2×10 mL). The combined organics were dried ($Na_2SO_4$) and concentrated to a tan solid. Purification by reverse phase chromatography (C18, acetonitrile/water, 0.05% trifluoroacetic acid) gave 12'-(N-isopropylaminomethyl)vinblastine trifluoroacetate (26.3 mg, 59%): $^1$H NMR (500 MHz, $CD_3OD$) δ 9.87 (s, 1H), 7.66 (s, 1H), 7.37 (d, J=8.3 Hz, 1H), 7.24 (dd, J=8.3, 1.4 Hz, 1H), 6.64 (s, 1H), 6.40 (s, 1H), 5.91 (dd, J=10.6, 4.2 Hz, 1H), 5.57 (d, J=8.9 Hz, 1H), 5.34 (s, 1H), 4.74-4.62 (m, 1H), 4.27 (d, J=3.2 Hz, 2H), 3.99-3.88 (m, 2H), 3.87-3.73 (m, 8H), 3.72-3.54 (m, 8H), 3.45-3.34 (m, 2H), 3.19 (s, 2H), 3.08-2.94 (m, 1H), 2.89 (dd, J=14.3, 5.9 Hz, 1H), 2.77 (s, 3H), 2.47 (dd, J=15.9, 4.6 Hz, 1H), 2.32-2.21 (m, 1H), 2.06 (s, 3H), 2.00-1.89 (m, 1H), 1.75-1.70 (m, 1H), 1.66 (d, J=4.1 Hz, 2H), 1.59-1.48 (m, 3H), 1.45-1.33 (m, 2H), 1.39 (d, J=6.5 Hz, 6H), 0.97 (t, J=7.5 Hz, 3H), 0.77 (t, J=7.4 Hz, 3H); ESI MS m/z 882 [M+H]$^+$.

Example 65

Preparation of 12'-Cyanovinblastine

A solution of 12'-iodovinblastine (496 mg, 0.53 mmol) in DMF (15 mL) was purged with argon for 10 min. Zinc cyanide (137 mg, 1.17 mmol), 1,1'-bis(diphenylphosphino)ferrocene (49 mg, 0.05 mmol), and tris(dibenzylideneacetone)dipalladium(0) (59 mg, 0.11 mmol) were added. The reaction mixture was purged with argon again and then heated to 65° C. for 5 h. The reaction mixture was cooled to 0° C., diluted with EtOAc, washed with 5% LiCl, and brine, dried (sodium sulfate), filtered, and concentrated under reduced pressure. Purification by flash column chromatography (silica, 96:4 to 94:6 $CH_2Cl_2$/MeOH) gave 12'-cyanovinblastine (167 mg, 38%) as a pale yellow solid: $^1$H NMR (300 MHz, $CD_3OD$) δ 7.88 (s, 1H), 7.33 (s, 2H), 6.55 (s, 1H), 6.32 (s, 1H), 5.82 (dd, J=9, 4 Hz, 1H), 5.35 (m, 2H), 4.06 (m, 2H), 3.81 (s, 3H), 3.76 (s, 3H), 3.64 (s, 3H), 3.59 (s, 1H), 3.23 (m), 3.06 (d, J=14 Hz, 1H), 2.81 (m, 4H), 2.71 (s, 3H), 2.48 (br d, J=9 Hz, 2H), 2.29 (d, J=14 Hz, 1H), 2.03 (m, 4H), 1.86 (m, 1H), 1.63 (m, 1H), 1.53 (m, 2H), 1.40 (m, 1H), 1.31 (m, 3H), 0.90 (m, 3H), 0.73 (m, 3H); ESI MS m/z 836 [M+H]$^+$.

Example 66

Preparation of 12'-Cyanovincristine

To a solution of iodovincristine (81.5 mg, 0.086 mmol) in DMF (4 mL), purged with argon, was added zinc cyanide (22 mg, 0.19 mmol) followed by 1,1'-bis(diphenylphosphino)ferrocene (10.5 mg, 0.019 mmol) and tris(dibenzylideneacetone)dipalladium(0) (8.5 mg, 0.009 mmol). The reaction mixture was heated at 65° C. for 4.5 h, cooled to room temperature, and then partitioned between methylene chloride and saturated aqueous sodium bicarbonate. The organic layer was dried (sodium sulfate), filtered, and concentrated under reduced pressure to give a brown residue. Purification by flash column chromatography (silica, 97:3 $CH_2Cl_2$/MeOH) followed by reversed phase chromatography (C18, water/MeOH) gave 12'-cyanovincristine (2.8 mg, 4%) as a white solid: $^1$H NMR (300 MHz, $CD_3OD$) δ 8.95 (s, 1H), 7.89 (s, 1H), 7.39 (d, J=8 Hz, 1H), 7.33 (d, J=8 Hz, 1H), 7.22 (s, 1H), 6.86 (s, 1H), 5.89 (dd, J=10, 5 Hz, 1H), 5.41 (d, J=10 Hz, 1H), 5.17 (s, 1H), 4.57 (s, 1H), 4.11 (t, J=14 Hz, 1H), 4.00 (m, 1H), 3.95 (s, 3H), 3.87 (s, 1H), 3.72 (s, 1H), 3.68 (s, 3H), 3.63 (s, 3H), 3.40-3.10 (m), 3.07 (s, 1H), 3.04 (m, 1H), 2.87 (d, J=15 Hz, 1H), 2.79 (m, 2H), 2.63 (td, J=14, 3 Hz, 1H), 2.44 (dd, J=15, 3 Hz, 1H), 2.30 (d, J=11 Hz, 1H), 2.05 (m, 2H), 2.00 (s, 3H), 1.75 (td, J=12, 7 Hz, H), 1.50 (m, 3H), 1.38 (m, 1H), 1.31 (q, J=7 Hz, 2H), 0.89 (t, J=7 Hz, 3H), 0.73 (t, J=7 Hz, 3H); ESI MS m/z 850 [M+H]$^+$.

Example 67

Preparation of 12'-(Methylcarbonyl)vinblastine Trifluoroacetate

Carbon monoxide was bubbled through a solution of 12'-iodovinblastine (81 mg, 0.086 mmol), triethylamine (87 mg, 0.86 mmol) and bis(triphenylphosphine)palladium(II) dichloride (12 mg, 0.017 mmol) in a mixture of DMF/methanol (3 mL, 1:1) for 5 min. The reaction mixture was heated at 50° C. for 14 h under one atmosphere of carbon monoxide (balloon). The solution then was diluted with ethyl acetate (20 mL) then washed with saturated aqueous $NaHCO_3$ (2×5 mL) and brine (5 mL), dried over $MgSO_4$, and evaporated to dryness in vacuo. The residue was purified by reverse phase chromatography (C18, acetonitrile/water, 0.05% trifluoroacetic acid) to provide 12'-(methylcarbonyl)vinblastine trifluoroacetate (53 mg, 56%) as a white powder after lyophilization: $^1$H NMR (500 MHz, $CD_3OD$) δ 10.13 (br s, 1H), 8.28 (s, 1H), 7.81 (dd, J=8.7, 1.4 Hz, 1H), 7.34 (d, J=8.6 Hz, 1H), 6.67 (s, 1H), 6.42 (s, 1H), 5.93 (dd, J=10.5, 4.5 Hz, 1H), 5.66 (d, J=10.5 Hz, 1H), 5.35 (s, 1H), 4.83 (m, 1H), 4.71 (dd, J=17.2, 10.9, 1H), 3.98-3.50 (m, 6H), 3.90 (s, 3H), 3.86 (s, 3H), 3.81 (s, 3H), 3.70 (s, 3H), 3.46 (d, J=16.2 Hz, 1H), 3.40 (dd, J=17.4, 8.4 Hz, 1H), 3.21 (m, 1H), 3.20 (s, 2H), 2.90 (dd, J=14.4, 6.1 Hz, 1H), 2.78 (s, 3H), 2.48 (dd, J=16.2, 4.9 Hz, 1H), 2.33 (m, 1H), 2.07 (s, 3H), 2.00 (m, 2H), 1.72 (m, 1H), 1.67 (m, 2H), 1.57 (m, 1H), 1.53 (q, J 7.5 Hz, 2H), 1.38 (m, 1H), 0.98 (t, J 7.4 Hz, 3H), 0.86 (t, J 7.2 Hz, 3H); ESI MS m/z 869 [M+H]$^+$.

Example 68

Preparation of 12'-(2,2,2-Trichloroethylcarbonyl) vinblastine Trifluoroacetate

Carbon monoxide was bubbled through a solution of 12'-iodovinblastine (53 mg, 0.057 mmol), triethylamine (57 mg, 0.565 mmol) and bis(triphenylphosphine)palladium (II) dichloride (8 mg, 0.011 mmol) in a mixture of DMF/2,2,2-trichloroethanol (2 mL, 1:1) for 5 min, then the reaction mixture was heated at 50° C. for 9 h under one atmosphere of carbon monoxide (balloon). The solution was diluted with ethyl acetate (15 mL) then washed with saturated aqueous $NaHCO_3$ (2×5 mL) and brine (5 mL), dried over $MgSO_4$ and evaporated to dryness in vacuo. The residue was purified by reverse phase chromatography (C18, acetonitrile/water, 0.05% trifluoroacetic acid) to provide 12'-(2,2,2-trichloroethylcarbonyl)vinblastine trifluoroacetate (33 mg, 48%) as a white powder after lyophilization: $^1$H NMR (500 MHz, $CD_3OD$) δ 10.25 (br s, 1H), 8.36 (s, 1H), 7.90 (dd, J=8.8, 1.5 Hz, 1H), 7.39 (d, J=8.7 Hz, 1H), 6.64 (s, 1H), 6.42 (s, 1H), 5.93 (dd, J=10.4, 4.2 Hz, 1H), 5.64 (d, J=10.5 Hz, 1H), 5.35 (s, 1H), 5.08 (d, J=12.2 Hz, 1H), 5.05 (d, J=12. Hz, 1H), 4.84 (m, 1H), 4.71 (dd, J=17.0, 11.3 Hz, 1H), 3.98-3.62 (m, 6H), 3.87 (s, 3H), 3.81 (s, 3H), 3.71 (s, 3H), 3.41 (m, 2H), 3.33 (m, 1H), 3.20 (s, 2H), 3.16 (m, 1H), 2.90 (dd, J=14.3, 6.0 Hz, 1H), 2.78 (s, 3H), 2.49 (dd, J=16.0, 3.6 Hz, 1H), 2.31 (m, 1H), 2.07

(s, 3H), 1.97 (m, 1H), 1.74 (m, 1H), 1.66 (m, 2H), 1.58 (m, 1H), 1.53 (q, J=7.5 Hz, 2H), 1.38 (m, 1H), 0.97 (t, J=7.4 Hz, 3H), 0.78 (t, J=7.2 Hz, 3H); ESI MS m/z 985 [M+H]$^+$.

Example 69

Preparation of 12'-(N-Methylaminocarbonyl)vinblastine Trifluoroacetate

Diisopropylethyl amine (36 mg, 0.276 mmol) was added to 12'-(carboxy)vinblastine (15 mg, 0.014 mmol) HATU (10 mg, 0.028 mmol), and N-methylamine (2.0 M in THF, 35 μL, 0.069 mmol) in DMF (0.6 mL). After stirring overnight only the 1-hydroxy-7-azabenztriazole ester was detected by ESI MS. N-Methylamine (40% aqueous solution, 0.5 mL) was added to the reaction mixture and the solvent was removed in vacuo. This procedure was repeated and the residue was then diluted with ethyl acetate (15 mL), washed with saturated aqueous NaHCO$_3$ (2×5 mL) and brine (5 mL), dried over MgSO$_4$, and evaporated to dryness in vacuo. The residue was purified by reverse phase chromatography (C18, acetonitrile/water, 0.05% trifluoroacetic acid) to provide 12'-(N-methylamino)vinblastine trifluoroacetate (3.4 mg, 22%): $^1$H NMR (500 MHz, CD$_3$OD) δ 10.01 (br s, 1H), 8.07 (s, 1H), 7.64 (dd, J=8.5, 1.5 Hz, 1H), 7.33 (d, J=8.5 Hz, 1H), 6.65 (s, 1H), 6.42 (s, 1H), 5.93 (dd, J=10.8, 4.7 Hz, 1H), 5.64 (d, J=10.3 Hz, 1H), 5.36 (s, 1H), 4.85 (m, 1H), 4.67 (dd, J=16.7, 11.8 Hz, 1H), 3.98-3.63 (m, 8H), 3.86 (s, 3H), 3.81 (s, 3H), 3.69 (s, 3H), 3.38 (m, 2H), 3.19 (m, 3H), 2.94 (s, 3H), 2.92 (m, 1H), 2.78 (s, 3H), 2.48 (dd, J=15.9, 4.2 Hz, 1H), 2.35 (m, 1H), 2.07 (s, 3H), 2.00 (m, 1H), 1.75 (m, 1H), 1.67 (m, 2H), 1.57 (m, 1H), 1.52 (q, J=7.6 Hz, 2H), 1.41 (m, 1H), 0.98 (t, J=7.4 Hz, 3H), 0.79 (t, J=7.1 Hz, 3H); ESI MS m/z 868 [M+H]$^+$.

Example 70

Preparation of 12'-Acetylvinblastine

A solution of 12'-(trimethylsilylethynyl)vinblastine (130 mg, 0.143 mmol) in formic acid (5 mL) was heated at 80° C. for 2 h. After cooling, the mixture was diluted with dichloromethane (25 mL) and poured slowly into saturated aqueous NaHCO$_3$. The organic layer was washed with brine, dried (Na$_2$SO$_4$), and concentrated under reduced pressure. Purification by flash chromatography (silica, 98:2:0.5 to 96:4:0.5 CHCl$_3$/MeOH/triethylamine) gave 12'-acetylvinblastine (88 mg, 84%). $^1$H NMR (300 MHz, CD$_3$OD) 8.19 (s, 1H), 7.78 (d, J=8 Hz, 1H), 7.25 (d, J=8 Hz, 1H), 6.56 (s, 1H), 6.31 (s, 1H), 5.85 (dd, J=10, 5 Hz, 1H), 5.35 (s, 1H), 5.30 (d, J=10 Hz, 1H), 4.07 (t, J=14 Hz, 1H), 4.01 (m, 1H), 3.81 (s, 3H), 3.76 (s, 3H), 3.65 (s, 3H), 3.14 (m, 1H), 2.82 (m), 2.83 (m, 1H), 2.78 (s, 1H), 2.75 (s, 1H), 2.72 (s, 3H), 2.64 (s, 3H), 2.44 (m, 2H), 2.31 (d, J=14 Hz, 1H), 2.08 (m, 1H), 2.01 (s, 3H), 1.88 (m, 1H), 1.67 (m, 1H), 1.56-1.33 (m, 5H), 0.90 (t, J=7 Hz, 3H), 0.75 (t, J=7 Hz, 3H); ESI m/z 853 [M+H]$^+$.

Example 71

Preparation of 12'-(3-Methylbutanoyl)vincristine

A solution of 12'-(3-methylbutynyl)vincristine (75 mg, 0.08 mmol) in formic acid (2 mL) was heated at 80° C. for 4 h. The reaction mixture was cooled to room temperature and neutralized by the addition of solid sodium bicarbonate. Water was added and the mixture was extracted with methylene chloride. The organic layer was dried (sodium sulfate), filtered, and concentrated under reduced pressure to give a brown residue. Purification by flash chromatography (silica, 97:3 to 95:5 CH$_2$Cl$_2$/MeOH) gave 12'-(3-methylbutanoyl)vincristine (27 mg, 35%) as a tan solid:
$^1$H NMR (300 MHz, CD$_3$OD) δ 8.95 (s, 1H), 8.18 (s, 1H), 7.78 (m, 2H), 7.32 (d, J=7 Hz, 1H), 7.23 (s, 1H), 6.88 (s, 1H), 5.89 (dd, J=10, 5 Hz, 1H), 5.40 (d, J=10 Hz, 1H), 5.19 (s, 1H), 4.57 (s, 1H), 4.15-4.05 (m, 2H), 3.90 (s, 3H), 3.87 (m, 1H), 3.72 (s, 1H), 3.69 (s, 3H), 3.62 (s, 3H), 3.40 (d, J=14 Hz, 1H), 3.32 (m), 3.17 (br d, J=14 Hz, 1H), 3.06 (s, 1H), 3.00-2.75 (m, 5H), 2.62 (t, J=10 Hz, 1H), 2.47 (dd, J=14, 4 Hz, 1H), 2.33 (dd, J=14, 4 Hz, 1H), 2.25 (m, 1H), 2.08 (m, 1H), 2.03 (s, 1H), 2.00 (s, 3H), 1.76 (m, 1H), 1.54-1.47 (m, 3H), 1.42-1.28 (m, 2H), 1.34 (q, J=7 Hz, 2H), 1.01 (d, J=7 Hz, 6H), 0.90 (t, J=7 Hz, 3H), 0.75 (t, J=7 Hz, 3H); ESI MS m/z 909 [M+H]$^+$.

Example 72

Preparation of 12'-(Hexanoyl)vincristine

Preparation of 12'-(hexanoyl)vinblastine from 12'-(hexynyl)vinblastine was carried out following the procedure described in Example 71 (29 mg, 40%): $^1$H NMR (300 MHz, CDCl$_3$) δ 8.95 (s, 1H), 8.18 (s, 1H), 7.78 (d, J=9 Hz, 1H), 7.31 (d, J=9 Hz, 1H), 7.23 (s, 1H), 6.87 (s, 1H), 5.89 (dd, J=10, 5 Hz, 1H), 5.41 (d, J=10 Hz, 1H), 5.17 (s, 1H), 4.58 (s, 1H), 4.12 (d, J=14 Hz, 1H), 4.05 (m, 2H), 3.91 (s, 3H), 3.87 (s, 1H), 3.72 (s, 1H), 3.69 (s, 3H), 3.63 (s, 3H), 3.42-3.00 (m, 7H), 2.83-2.70 (m, 3H), 2.62 (br t, J=10 Hz, 1H), 2.43 (dd, J=15, 4 Hz, 1H), 2.29 (dd, J=15, 4 Hz, 1H), 2.14-2.00 (m, 1H), 2.00 (s, 3H), 1.74 (m, 3H), 1.60-1.25 (m, 11H), 0.93 (t, J=7 Hz, 3H), 0.90 (t, J=7 Hz, 3H), 0.73 (t, J=7 Hz, 3H); ESI MS m/z 923 [M+H]$^+$.

Example 73

Preparation of 12'-(3-Methylbutyl)vincristine

To a solution of 12'-(3-methylbutynl)vincristine (15 mg, 0.02 mmol) in trifluoroacetic acid (1 mL) was added Et$_3$SiH (0.05 mg, 0.31 mmol) and the reaction mixture was stirred overnight. Saturated aqueous sodium bicarbonate was added to quench the reaction and the mixture was extracted with methylene chloride. The organic layer was dried (sodium sulfate), filtered, and concentrated under reduced pressure to give a tan solid. Purification by flash column chromatography (silica, 95:5 to 90:10 CH$_2$Cl$_2$/MeOH) gave 12'-(3-methylbutyl)vincristine (9 mg, 50%) as an off-white solid: $^1$H NMR (300 MHz, CD$_3$OD) δ 8.93 (s, 1H), 7.22 (s, 1H), 7.15 (d, J=9 Hz, 1H), 6.96-6.94 (m, 2H), 5.90-5.88 (m, 1H), 5.40 (d, J=10 Hz, 1H), 5.15 (s, 1H), 4.58 (s, 1H), 4.09-4.07 (m, 1H), 3.90 (s, 3H), 3.73-3.71 (m, 3H), 3.68 (s, 3H), 3.63 (s, 3H), 3.44-3.19 (m, 3H), 3.07-3.05 (m, 2H), 2.89-2.65 (m, 6H), 2.49-2.39 (m, 2H), 2.03-2.01 (m, 1H), 1.99 (s, 3H), 1.82-1.80 (m, 1H), 1.57-1.50 (m, 3H), 1.41-1.28 (m, 9H), 0.96 (d, J=5 Hz, 6H), 0.89-0.78 (m, 8H); ESI MS m/z 895 [M+H]$^+$.

Example 74

Preparation of 12'-Hexylvincristine

12'-hexylvincristine was prepared from 12'-(hexanoyl)vincristine following the procedure described in Example 73 (87 mg, 44%). $^1$H NMR (300 MHz, CD$_3$OD) δ 8.92 (s, 1H), 7.89 (s, 1H), 7.20 (s, 2H), 7.21 (d, J=8 Hz, 1H), 6.95 (s, 1H), 6.92

(d, J=8 Hz, 1H), 5.88 (dd, J=10, 5 Hz, 1H), 5.40 (d, J=10 Hz, 1H), 5.15 (s, 1H), 4.58 (s, 1H), 4.08 (t, J=14 Hz, 1H), 3.99-3.97 (m, 1H), 3.90 (s, 3H), 3.85 (s, 1H), 3.70 (s, 1H), 3.67 (s, 3H), 3.63 (s, 3H), 3.45-3.15 (m, 2H), 3.08-3.06 (m, 2H), 2.90-2.55 (m, 6H), 2.39 (dd, J=15, 5 Hz, 1H), 2.32 (dd, J=15, 5 Hz, 1H), 2.04-2.03 (m, 1H), 2.00 (s, 3H), 1.81-1.79 (m, 1H), 1.60-1.20 (m, 16H), 0.89 (t, J=7 Hz, 6H), 0.81 (t, J=7 Hz, 3H); ESI MS m/z 909 [M+H]$^+$.

Example 75

Preparation of 12'-Methylvinblastine Trifluoroacetate

Dimethylzinc (2.0 M in toluene, 0.054 mL, 0.109 mmol) was added to 12'-iodovinblastine (51 mg, 0.054 mmol) and [1,1'-bis(diphenylphosphino)ferrocene]dichloropalladium (II) (4.4 mg, 0.005 mmol) in anhydrous 1,4-dioxane (2 mL) under nitrogen. The reaction mixture was heated at 45° C. for 45 min then quenched by the addition of saturated aqueous NaHCO$_3$ (3 mL). After extraction with chloroform (3×5 mL), the combined organic extracts were washed with brine (5 mL), dried over MgSO$_4$, and evaporated to dryness in vacuo. The residue was purified by reverse phase chromatography (C18, acetonitrile/water, 0.05% trifluoroacetic acid) to provide 12'methylvinblastine trifluoroacetate (9.4 mg, 16%): $^1$H NMR (500 MHz, CD$_3$OD) δ 9.33 (s, 1H), 7.30 (s, 1H), 7.16 (d, J=8.3 Hz, 1H), 6.97 (d, J=8.3 Hz, 1H), 6.68 (s, 1H), 6.42 (s, 1H), 5.93 (dd, J=10.4, 4.1 Hz, 1H), 5.64 (d, J=10.5 Hz, 1H), 5.36 (s, 1H), 4.61 (dd, J=16.8, 11.0, 1H), 3.92 (m, 3H), 3.86 (s, 3H), 3.82 (s, 3H), 3.75-3.58 (m, 5H), 3.69 (s, 3H), 3.47 (d, J=15.7 Hz, 1H), 3.30 (m, 1H), 3.21 (m, 1H), 2.88 (dd, J=14.3, 7.0 Hz, 1H), 2.77 (s, 3H), 2.48-2.32 (m, 3H), 2.41 (s, 3H), 2.07 (s, 3H), 2.04 (m, 2H), 1.76 (m, 1H), 1.66 (m, 2H), 1.52 (m, 3H), 1.38 (m, 1H), 0.97 (t, J=7.4 Hz, 3H), 0.81 (t, J=7.3 Hz, 3H); ESI MS m/z 825 [M+H]$^+$.

Example 76

Preparation of 12'-Methylvincristine Trifluoroacetate

Dimethylzinc (0.080 mL of a 2.0 M solution in toluene, 0.160 mmol) was added to 12'-iodovincristine (61 mg, 0.064 mmol) and [1,1'-bis(diphenylphosphino)ferrocene]-dichloropalladium (II) (9.4 mg, 0.012 mmol) in anhydrous 1,4-dioxane (1 mL) under nitrogen. The reaction mixture was heated to 80° C. for 2 h then quenched by the addition of saturated aqueous NaHCO$_3$ (3 mL). After extraction with EtOAc (2×5 mL), the combined organic extracts were dried (Na$_2$SO$_4$), and evaporated to dryness in vacuo. The residue was purified by reverse phase chromatography (C18, acetonitrile/water, 0.05% trifluoroacetic acid) to provide 12'-methylvincristine trifluoroacetate (16 mg, 30%): $^1$H NMR (500 MHz, CD$_3$OD) δ 9.42 (br s, 1H), 8.98 (s, 1H), 7.33 (s, 1H), 7.30 (s, 1H), 7.20 (d, J=8.5 Hz, 1H), 6.99-6.96 (m, 2H), 5.97 (dd, J=10.5, 5 Hz, 1H), 7.73 (d. J=10.5 Hz, 1H), 5.18 (s, 1H), 4.67-4.64 (m, 2H), 4.06-4.02 (m, 1H), 3.99-3.87 (m, 6H), 3.84-3.60 (m, 10H), 3.52 (d, J=15.5 Hz, 1H), 3.34-3.12 (m, 1H), 3.16 (br s, 2H), 2.82 (dd, J=14.0, 6.0 Hz, 1H), 2.51-2.48 (m, 1H), 2.41-2.37 (m, 4H), 2.07-1.96 (m, 4H), 1.67-1.57 (m, 3H), 1.53-1.46 (m, 3H), 1.30-1.28 (m, 1H), 0.96 (t, J=7.0 Hz, 3H), 0.83 (t, J=7.0 Hz, 3H); ESI MS m/z 839 [M+H]$^+$.

Example 77

Preparation of 12'-Ethylvinblastine Trifluoroacetate

Diethylzinc (1.1 M in toluene, 0.103 mL, 0.113 mmol) was added to 12'-iodovinblastine (53 mg, 0.057 mmol) and [1,1'-bis(diphenylphosphino)ferrocene]dichloropalladium (II) (4.6 mg, 0.006 mmol) in anhydrous 1,4-dioxane (2 mL) under nitrogen. The reaction mixture was heated at 45° C. for 45 min then quenched by the addition of saturated aqueous NaHCO$_3$ (3 mL). After extraction with chloroform (3×4 mL) the combined organic extracts were washed with brine (5 mL), dried over MgSO$_4$, and evaporated to dryness in vacuo. The residue was purified by reverse phase chromatography (C18, acetonitrile/water, 0.05% trifluoroacetic acid) to provide 12'-ethylvinblastine as a salt of thrifluoroacetic acid (33.2 mg, 55%): $^1$H NMR (500 MHz, CD$_3$OD) δ 9.34 (br s, 1H), 7.31 (s, 1H), 7.19 (d, J=8.3 Hz, 1H), 7.00 (dd, J=8.4, 1.1 Hz, 1H), 6.68 (s, 1H), 6.42 (s, 1H), 5.94 (dd, J=10.5, 4.2 Hz, 1H), 5.64 (d, J=10.2 Hz, 1H), 5.36 (s, 1H), 4.84 (m, 1H), 4.62 (dd, J=17.0, 11.6, 1H), 3.58-3.95 (m, 6H), 3.86 (s, 3H), 3.82 (s, 3H), 3.69 (s, 3H), 3.48 (d, J=15.8 Hz, 1H), 3.33 (m, 1H), 3.18 (m, 3H), 2.88 (dd, J=14.3, 6.0 Hz, 1H), 2.77 (s, 3H), 2.71 (q, J=7.5 Hz, 2H), 2.46 (m, 1H), 2.36 (m, 1H), 2.07 (s, 3H), 2.03 (m, 2H), 1.78 (m, 1H), 1.66 (m, 2H), 1.52 (m, 3H), 1.39 (m, 1H), 1.24 (t, J=7.5 Hz, 3H), 0.97 (t, J=7.4 Hz, 3H), 0.81 (t, J=7.3 Hz, 3H); ESI MS m/z 839 [M+H]$^+$.

Example 78

Preparation of 12'-Ethylvincristine Trifluoroacetate

Diethylzinc (0.174 mL of a 1.0 M solution in toluene, 0.174 mmol) was added to 12'-iodovincristine (66 mg, 0.069 mmol) and [1,1'-bis(diphenylphosphino)ferrocene]dichloropalladium (II) (10.2 mg, 0.014 mmol) in anhydrous 1,4-dioxane (1 mL) under nitrogen. The reaction mixture was heated to 80° C. for 2 h then quenched by the addition of saturated aqueous NaHCO$_3$ (3 mL). After extraction with EtOAc (2×5 mL), the combined organic extracts were dried (Na$_2$SO$_4$), and evaporated to dryness in vacuo. The residue was purified by reverse phase chromatography (C18, acetonitrile/water, 0.05% trifluroacetic acid) to provide 12'-ethylvincristine trifluoroacetate (28 mg, 46%): $^1$H NMR (500 MHz, CD$_3$OD) δ 9.65 (br s, 1H), 8.98 (s, 1H), 7.33 (s, 2H), 7.31 (s, 1H), 7.23 (d, J=8 Hz, 1H), 7.01-6.99 (m, 2H), 5.98 (dd, J=10.5, 5.0 Hz, 1H), 5.73 (dd, J=10.5 Hz, 1H), 5.18 (s, 1H), 4.69-4.67 (m, 2H), 4.07-4.04 (m, 1H), 4.00-3.87 (m, 6H), 3.84-3.58 (m, 8H), 3.54-3.51 (m, 2H), 3.36-3.35 (m, 1H), 3.19-3.15 (m, 2H), 2.82 (dd, J=14.5, 6 Hz, 1H), 2.71 (q, J=10.0 Hz, 2H), 2.51-2.49 (m, 1H), 2.41-2.36 (m, 1H), 2.08-1.94 (m, 5H), 1.67-1.58 (m, 3H), 1.53-1.47 (m, 3H), 1.31-1.26 (m, 1H), 1.22 (t, J=8.0 Hz, 3H), 0.96 (t, J=7.5 Hz, 3H), 0.83 (t, J=7.0 Hz, 3H); ESI MS m/z 853 [M+H]$^+$.

Example 79

Preparation of 12'-(N-Methyl-N-phenylamino)vinblastine Trifluoroacetate

12'-(N-Methyl-N-phenylamino)vinblastine was prepared according to the scheme below.

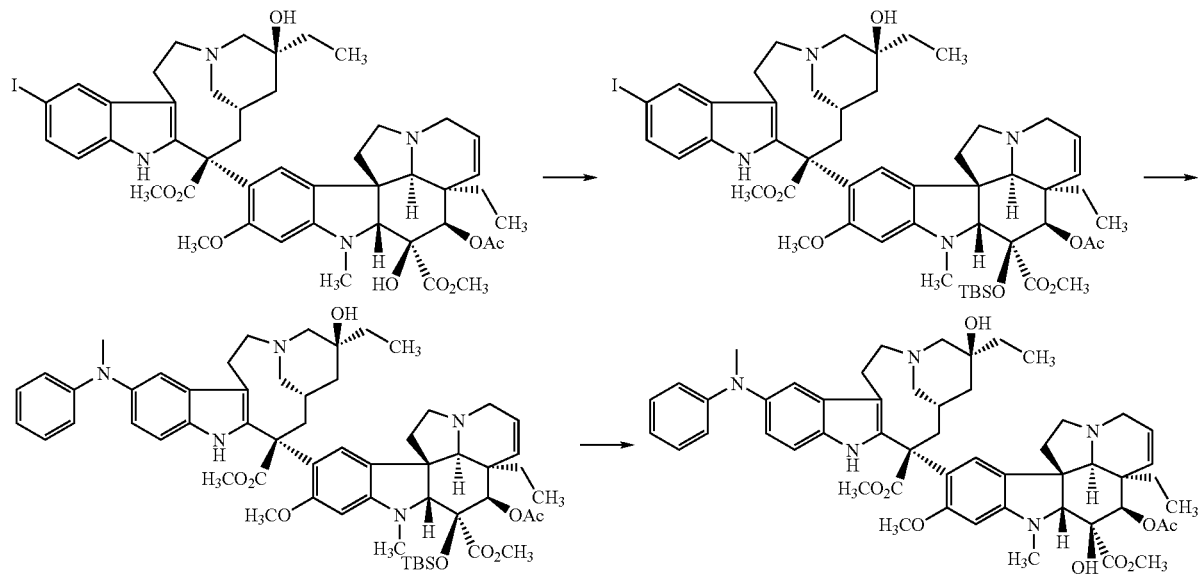

Step 1: A solution of 12'-iodovinblastine (308 mg, 0.328 mmol) in CH$_2$Cl$_2$ (3 mL) was charged with N,N-diisopropylethylamine (575 µL, 3.28 mmol) and tert-butyldimethylsilyl trifluoromethanesulfonate (128 µL, 0.558 mmol). After 2 h, the reaction mixture was diluted with saturated aqueous NaHCO$_3$ (8 mL) and extracted with CH$_2$Cl$_2$ (2×10 mL). The combined extracts were dried (Na$_2$SO$_4$) and concentrated to a brown solid which was purified by flash chromatography (silica, [CHCl$_3$/MeOH/NH$_4$OH (40:18:2)]/CH$_2$Cl$_2$, 1:99 to 10:90) to yield 12'-Iodo-3,4'-(tert-butyldimethylsilanyloxy) vinblastine (88 mg, 25%) as a white solid and 12'-Iodo-3-(tert-butyl-dimethylsilanyloxy)vinblastine (80 mg, 23%) as a white solid. The data for 12'-Iodo-3,4'-(tert-butyl-dimethylsilanyloxy)vinblastine is as ffollows: ESI MS m/z 1165 [C$_{58}$H$_{85}$IN$_4$O$_9$Si$_2$+H]$^+$. 12'-Iodo-3-(tert-butyldimethylsilanyloxy)vinblastine: ESI MS m/z 1051 [M+H]$^+$.

Step 2: 12'-Iodo-3,4'-(tert-butyldimethylsilanyloxy)vinblastine (32 mg, 0.030 mmol), N-methylaniline (7.4 mg, 0.070 mmol), and NaOt-Bu (9.2 mg, 0.10 mmol) were dissolved in anhydrous toluene (1.0 mL) while stirring under argon atmosphere in a sealed tube. The reaction mixture was deoxygenated with argon at room temperature for 3 min then tris(dibenzylideneacetone)dipalladium(0) (2.5 mg, 2.7 µmol) and 2-(dicyclohexyl-phosphino)-2',4',6'-tri-i-propyl-1,1'-biphenyl (2.6 mg, 10 µmol) were added. The reaction mixture was sealed and heated to 80° C. for 4 h. The reaction mixture was cooled to room temperature, diluted with EtOAc, filtered through diatomaceous earth, and then concentrated to provide crude 12'-(N-methyl-N-phenylamino)-3,4'-(tert-butyl-dimethylsilanyloxy)vinblastine: ESI MS m/z 1144 [M+H]$^+$.

Step 3: A solution of crude 12'-(N-methylphenylamino)-3,4'-(tert-butyldimethylsilanyloxy)vinblastine (32 mg, 0.030 mmol) in THF (1.5 mL) was treated with tetrabutylammonium fluoride (400 µL of a 1N solution in THF, 0.40 mmol). After 16 h, the reaction mixture was diluted with saturated aqueous NaHCO$_3$ (10 mL) and then extracted with CH$_2$Cl$_2$ (2×10 mL). The combined organics were dried (Na$_2$SO$_4$), concentrated, and purified by purified by flash chromatography (silica gel, [CHCl$_3$/MeOH/NH$_4$OH (40:18:2)]/CH$_2$Cl$_2$, 1:99 to 10:90) to yield 12'-(N-methyl-N-phenylamino)-4'-(tert-butyldimethylsilanyloxy)vinblastine: ESI MS m/z 1030 [M+H]$^+$.

Step 4: A solution of 12'-(N-methyl-N-phenylamino)-4'-(tert-butyldimethylsilanyloxy)vinblastine (32 mg, 0.030 mmol) was stirred HF-pyridine (100 µL) as a neat solution in a flask. After 16 h, the reaction mixture was diluted with saturated aqueous NaHCO$_3$ (10 mL) and then extracted with CH$_2$Cl$_2$ (2×10 mL). The combined organics were dried (Na$_2$SO$_4$), concentrated, and purified by reverse phase chromatography (C18, acetonitrile/water, 0.05% trifluoroacetic acid) to provide 12'-(N-methyl-N-phenylamino)vinblastine trifluoroacetate (6 mg, 24%): $^1$H NMR (500 MHz, CD$_3$OD) δ 9.67 (br s, 1H), 7.31-7.28 (m, 2H), 7.11-7.09 (m, 2H), 6.94 (dd, J=9.0, 2.0 Hz, 1H), 6.76 (s, 1H), 6.70-6.66 (m, 3H), 6.43 (s, 1H), 5.95 (dd, J=10.5, 4.5 Hz, 1H), 5.66 (d, J=110 Hz, 1H), 5.36 (s, 1H), 4.61 (dd, J=17.0, 12.0 Hz, 1H), 3.99-3.86 (m, 3H), 3.85-3.83 (m, 4H), 3.82-3.78 (m, 4H), 3.77-3.70 (m, 5H), 3.65-3.51 (m, 3H), 3.34-3.22 (m, 6H), 3.16 (br s, 2H), 2.90 (dd, J=14.5, 4.5 Hz, 1H), 2.78 (s, 3H), 2.46-2.44 (m, 1H), 2.38-2.34 (m, 1H), 2.07-2.02 (m, 4H), 1.78-1.74 (m, 1H), 1.65-1.64 (m, 1H), 1.60-1.49 (m, 2H), 1.41-1.39 (m, 1H), 0.96 (t, J=7.5 Hz, 3H), 0.84 (t, J=7.5 Hz, 3H); ESI MS m/z 916 [M+H]$^+$.

Example 80

Preparation of 12'-Aminovinblastine Trifluoroacetate

Step 1: 12'-Iodo-3-(tert-butyldimethylsilanyloxy)-vinblastine (100 mg, 0.0951 mmol), benzophenone imine (39 µL, 0.23 mmol), and NaOt-Bu (32 mg, 0.33 mmol) were dissolved in anhydrous toluene (3 mL) while stirring under argon atmosphere in a sealed tube. The mixture was deoxygenated with argon at room temperature for 3 min then tris(dibenzylideneacetone)dipalladium(0) (8.7 mg, 9.5 μmol) and 2-(dicyclohexylphosphino)-2',4',6'-tri-i-propyl-1,1'-biphenyl (9.0 mg, 19 μmol) were added. The reaction vessel was sealed and the mixture heated to 80° C. for 3 h. The reaction mixture was cooled to room temperature, diluted with EtOAc, filtered through diatomaceous earth, and concentrated to provide crude 12'-benzhydrylideneamino-3-(tert-butyldimethylsilanyloxy)-vinblastine.

Step 2: A solution of crude 12'-benzhydrylideneamino-3-(tert-butyldimethylsilanyloxy)vinblastine (105 mg, 0.0952 mmol) in methanol (1.5 mL) was treated with NaOAc (54 mg, 0.66 mmol) and hydroxylamine hydrochloride (33 mg, 0.47 mmol). After 4 h, the reaction appeared complete as indicated by ESI mass spectral analysis and the reaction mixture was concentrated to dryness. The residue was diluted with saturated aqueous NaHCO$_3$ (10 mL) and extracted with CH$_2$Cl$_2$ (2×10 mL). The combined extracts were dried (Na$_2$SO$_4$), and then concentrated to provide crude 12'-amino-3-(tert-butyldimethylsilanyloxy)-vinblastine as a brown oil. A solution of crude 12'-amino-3-(tert-butyldimethylsilanyloxy)vinblastine (89 mg, 0.094 mmol) in THF (1.5 mL) was treated with tetrabutylammonium fluoride (450 μL of a 1 N solution in THF, 0.450 mmol). After 3 h, the reaction appeared complete as indicated by ESI mass spectral analysis. The reaction mixture was diluted with saturated aqueous NaHCO$_3$ (10 mL) and extracted with EtOAc (2×10 mL). The combined extracts were dried (Na$_2$SO$_4$) and concentrated. The residue was purified by reverse phase chromatography (C18, acetonitrile/water, 0.05% trifluoroacetic acid) to provide 12'-aminovinblastine trifluoroacetate (32 mg, 32% yield over 3 steps): 1H NMR (500 MHz, CD$_3$OD) δ 10.24 (br s, 1H), 7.50 (d, J=2.0 Hz, 1H), 7.43 (d, J=8.5 z, 1H), 7.11 (dd, J=8.5, 2.0 Hz, 1H), 6.70 (s, 1H), 6.42 (s, 1H), 5.93 (dd, J=10.5, 4.0 Hz, 1H), 5.68 (d, J=10.5 Hz, 1H), 5.34 (s, 1H), 4.74-4.72 (m, 1H), 3.98-3.90 (m, 4H), 3.86-3.84 (m, 4H), 3.78-3.70 (m, 3H), 3.70-3.63 (m, 6H), 3.48 (d, J=16.0 Hz, 1H), 3.30-3.23 (m, 2H), 3.19-3.17 (m, 2H), 2.89 (dd, J=14.5, 6.0 Hz, 1H), 2.79-2.77 (m, 4H), 2.48-2.45 (m, 1H), 2.34-2.31 (m, 1H), 2.07-1.97 (m, 5H), 1.77-1.51 (m, 6H), 1.41-1.35 (m, 1H), 0.97 (t, J=7.5 Hz, 3H), 0.78 (t, J=7.0 Hz, 3H); ESI MS m/z 826 [M+H]$^+$.

Example 81

Preparation of 12'-(N,N-Dimethylamino)vinblastine Trifluoroacetate

Step 1: 12'-Iodo-3-(tert-butyl-dimethylsilanyloxy)vinblastine (31 mg, 0.030 mmol), dimethylamine hydrochloride (6.0 mg, 0.070 mmol), and NaOt-Bu (17 mg, 0.18 mmol) were dissolved in anhydrous toluene (1.0 mL) while stirring under argon atmosphere in a sealed tube. The mixture was deoxygenated with an argon at room temperature for 3 min then tris(dibenzylideneacetone)dipalladium(0) (2.7 mg, 2.9 μmol) and 2-(dicyclohexylphosphino)-2',4',6'-tri-i-propyl-1,1'-biphenyl (2.8 mg, 6.0 μmol) were added. The reaction vessel was sealed and the mixture was heated to 80° C. for 3.5 h. The reaction mixture was cooled to room temperature, diluted with EtOAc, filtered through diatomaceous earth, and then concentrated to provide crude 12'-(N,N-dimethylamino)-3-(tert-butyldimethyl-silanyloxy)vinblastine.

Step 2: A solution of 12'-(N,N-dimethylamino)-3-(tert-butyldimethylsilanyloxy)vinblastine (28.7 mg, 0.030 mmol) in THF (1.0 mL) was treated with tetrabutylammonium fluoride (400 μL of a 1 N solution in THF, 0.42 mmol). After 3.5 h, the reaction mixture was diluted with saturated aqueous NaHCO$_3$ (10 mL) and then extracted with CH$_2$Cl$_2$ (2×10 mL). The combined extracts were dried (Na$_2$SO$_4$), concentrated, and purified by reverse phase chromatography (C18, acetonitrile/water, 0.05% trifluoroacetic acid) to provide 12'-(N,N-dimethylamino)vinblastine trifluoroacetate (8.8 mg, 25%): $^1$H NMR (500 MHz, CD$_3$OD) δ 10.34 (br s, 1H), 7.83 (d, J=2.0 Hz, 1H), 7.47 (d, J=8.5 Hz, 1H), 7.33 (dd, J=9.0, 2.5 Hz, 1H), 6.69 (s, 1H), 6.42 (s, 1H), 5.95-5.92 (m, 1H), 5.68 (d, J=10.5 Hz, 1H), 5.34 (s, 1H), 4.75-4.71 (m, 1H), 3.97-3.81 (m, 10H), 3.78-3.65 (m, 7H), 3.50-3.47 (m, 1H), 3.40-3.30 (m, 7H), 3.27-3.22 (m, 1H), 3.19 (br s, 2H), 2.89 (dd, J=14.5, 6.5 Hz, 1H), 2.78 (s, 3H), 2.47 (dd, J=16.0, 4.5 Hz, 1H), 2.35-2.32 (m, 1H), 2.07-1.99 (m, 4H), 1.75-1.66 (m, 3H), 1.61-1.51 (m, 3H), 1.40-1.37 (m, 1H), 0.97 (t, J=7.5 Hz, 3H), 0.77 (t, J=7.5 Hz, 3H); ESI MS m/z 854 [M+H]$^+$.

Example 82

Preparation of 12'-(4-Methoxyphenylamino)vinblastine Trifluoroacetate

Step 1: 12'-Iodo-3-(tert-butyldimethylsilanyloxy)vinblastine (33 mg, 0.030 mmol), aniline (7.3 mg, 0.080 mmol), and NaOt-Bu (10 mg, 0.11 mmol) were dissolved in anhydrous toluene (1.0 mL) while stirring under an argon atmosphere in a sealed tube. The mixture was deoxygenated with argon at room temperature for 3 min then tris(dibenzylideneacetone)dipalladium(0) (2.9 mg, 3.2 μmol) and 2-(dicyclohexylphosphino)-2',4',6'-tri-i-propyl-1,1'-biphenyl (3.0 mg, 6.4 μmol) were added. The reaction was sealed and heated to 80° C. for 3.5 h. The reaction mixture was cooled to room temperature, diluted with EtOAc, filtered through diatomaceous earth, and then concentrated to provide crude 12'-(phenylamino)-3-(tert-butyldimethylsilanyloxy)vinblastine.

A solution of crude 12'-(phenylamino)-3-(tert-butyldimethylsilanyloxy)vinblastine (32.7 mg, 0.030 mmol) in THF (1.0 mL) was treated with tetrabutylammonium fluoride (400 μL of a 1 N solution in THF, 0.42 mmol). After 3.5 h, the reaction mixture was diluted with saturated aqueous NaHCO$_3$ (10 mL) and then extracted with CH$_2$Cl$_2$ (2×10 mL). The combined organics were dried (Na$_2$SO$_4$), concentrated, and purified by reverse phase chromatography (C18, acetonitrile/water, 0.05% trifluoroacetic acid) to provide 12'-(phenylamino)vinblastine trifluoroacetate (6 mg, 20%): $^1$H NMR (500 MHz, CD$_3$OD) δ 7.21 (d, J=2.0 Hz, 1H), 7.13-7.09 (m, 3H), 6.95-6.90 (m, 3H), 6.70-6.66 (m, 2H), 6.32 (s, 1H), 5.88-5.83 (m, 1H), 5.37 (s, 1H), 5.29 (d, J=10.0 Hz, 1H), 4.08-3.95 (m, 2H), 3.83-3.81 (m, 4H), 3.76 (s, 3H), 3.65 (s, 3H), 3.50-3.46 (m, 2H), 3.34-3.30 (m, 1H), 3.29-3.18 (m, 3H), 2.99-2.95 (m, 1H), 2.82-2.78 (m, 3H), 2.71 (s, 3H), 2.51-2.47 (m, 2H), 2.32-2.28 (m, 1H), 2.13-2.07 (m, 4H), 1.95-1.88 (m, 1H), 1.72-1.67 (m, 1H), 1.54-1.49 (m, 1H), 1.44-1.39 (m, 2H), 1.35-1.28 (m, 3H), 0.90 (t, J=7.5 Hz, 3H), 0.81 (t, J=7.5 Hz, 3H); ESI MS m/z 902 [M+H]$^+$.

Example 83

Preparation of 12'-(4-Methoxyphenylamino)vinblastine Trifluoroacetate

Step 1: 12'-Iodo-3-(tert-butyl-dimethylsilanyloxy)vinblastine (54.4 mg, 0.0501 mmol), p-anisidine (14 mg, 0.13 mmol), and NaOt-Bu (17 mg, 0.18 mmol) were dissolved in anhydrous toluene (1.0 mL) while stirring under argon atmosphere in a sealed tube. The reaction mixture was deoxygenated with argon at room temperature for 3 min then tris(dibenzylideneacetone)dipalladium(0) (4.7 mg, 5.2 μmol) and 2-(dicyclohexylphosphino)-2',4',6'-tri-i-propyl-1,1'-biphenyl (4.9 mg, 10 μmol) were added. The reaction vessel was sealed and heated to 80° C. for 4 h. The reaction mixture was cooled to room temperature, diluted with EtOAc, filtered through diatomaceous earth, and then concentrated to provide crude 12'-(4-methoxyphenylamino)-3-(tert-butyl-dimethylsilanyloxy)vinblastine: ESI MS m/z 1046 [M+H]$^+$.

Step 2: A solution of 12'-(4-methoxyphenylamino)-3-(tert-butyldimethylsilanyloxy)vinblastine (54 mg, 0.051 mmol) in THF (1.0 mL) was treated with tetrabutylammonium fluoride (154 μL of a 1 N solution in THF, 0.154 mmol). After 4 h, the reaction mixture appeared complete as indicated by ESI mass spectral analysis. The reaction mixture was diluted with saturated aqueous NaHCO$_3$ (10 mL) and extracted with CH$_2$Cl$_2$ (2×10 mL). The combined extracts were dried (Na$_2$SO$_4$), concentrated, and purified by reverse phase chromatography (C18, acetonitrile/water, 0.05% trifluoroacetic acid) to provide 12'-(4-methoxyphenylamino)vinblastine trifluoroacetate (23 mg, 48%): $^1$H NMR (500 MHz, CD$_3$OD) δ 9.98 (br s, 1H), 7.33 (s, 1H), 7.27 (d, J=8.5 Hz, 1H), 7.03 (d, J=7 Hz, 2H), 6.91 (d, J=8.0 Hz, 1H), 6.82 (d, J=8.5 Hz, 2H), 6.63 (s, 1H), 6.42 (s, 1H), 5.94 (dd, J=10.5, 4.0 Hz, 1H), 5.85 (d, J=4.5 Hz, 1H), 5.63 (d, J=9.5 Hz, 1H), 5.32 (s, 1H), 4.76 (d, J=14.5 Hz, 1H), 4.65-4.63 (m, 1H), 4.03 (d, J=16.5 Hz, 1H), 3.94 (dd, J=15.0, 5.0 Hz, 1H), 3.92-3.87 (m, 4H), 3.85 (m, 4H), 3.78-3.71 (m, 10H), 3.47-3.44 (m, 1H), 3.45-3.29 (m, 2H), 3.20-3.08 (m, 2H), 2.82 (dd, J=13.5, 4.5 Hz, 1H), 2.78 (s, 3H), 2.63-2.57 (m, 1H), 2.37-2.32 (m, 1H), 2.17-2.03 (m, 7H), 1.95-1.92 (m, 1H), 1.70-1.64 (m, 1H), 1.12 (t, J=7.5 Hz, 3H), 0.76 (t, J=7.0 Hz, 3H); ESI MS m/z 932 [C$_{53}$H$_{65}$N$_5$O$_{10}$+H]$^+$.

Example 84

Preparation of 12'-(4-Trifluoromethylphenylamino)vinblastine Trifluoroacetate

Step 1: 12'-Iodo-3-(tert-butyldimethylsilanyloxy)vinblastine (31 mg, 0.030 mmol), 4-trifluoromethylaniline (11 mg, 0.070 mmol), and NaOt-Bu (9.0 mg, 0.090 mmol) were dissolved in anhydrous toluene (1.0 mL) while stirring under an argon atmosphere in a sealed tube. The mixture was deoxygenated with argon at room temperature for 3 min then tris(dibenzylideneacetone)dipalladium(0) (2.4 mg, 2.6 μmol) and 2-(dicyclohexylphosphino)-2',4' 6'-tri-i-propyl-1,1'-biphenyl (2.5 mg 5.3 μmol) were added. The reaction was sealed and heated to 80° C. for 3 h. The reaction mixture was cooled to room temperature, diluted with EtOAc, filtered through diatomaceous earth, and then concentrated to provide crude 12'-(4-trifluoromethylphenylamino)-3-(tert-butyldimethylsilanyloxy)vinblastine.

Step 2: A solution of crude 12'-(4-trifluoromethylphenylamino)-3-(tert-butyldimethylsilanyloxy)vinblastine (29 mg, 0.030 mmol) in THF (1.0 mL) was treated with tetrabutylammonium fluoride (700 μL of a 1 N solution in THF, 0.70 mmol). After 16 h, the reaction mixture was diluted with saturated aqueous NaHCO$_3$ (10 mL) and then extracted with CH$_2$Cl$_2$ (2×10 mL). The combined organics were dried (Na$_2$SO$_4$), concentrated, and purified by reverse phase chromatography (C18, acetonitrile/water, 0.05% trifluoroacetic acid) to provide 12'-(4-trifluoromethylphenylamino)vinblastine trifluoroacetate (5 mg, 19%): $^1$H NMR (500 MHz, CD$_3$OD) δ 7.37-7.33 (m, 3H), 7.26 (d, J=8.5 Hz, 1H), 7.02 (dd, J=8.5, 1.5 Hz, 1H), 6.94 (d, J=8.5 Hz, 2H), 6.58 (br s, 1H), 6.39 (s, 1H), 5.90 (dd, J=9.5, 4.5 Hz, 1H), 5.47-5.43 (m, 1H), 5.35 (s, 1H), 4.61-4.58 (m, 1H), 3.96-3.90 (m, 2H), 3.85 (s, 3H), 3.81-3.79 (m, 4H), 3.69-3.57 (m, 8H), 3.44-3.24 (m, 4H), 3.17 (br s, 2H), 2.89-2.88 (m, 1H), 2.74 (s, 3H), 2.49-2.46 (m, 1H), 2.23-2.21 (m, 1H), 2.05 (s, 3H), 1.92-1.90 (m, 1H), 1.74-1.66 (m, 2H), 1.53-1.38 (m, 3H), 1.29-1.27 (m, 1H), 0.96 (t, J=7.5 Hz, 3H), 0.80 (t, J=7.0 Hz, 3H); ESI MS m/z 970 [M+H]$^+$.

Example 85

Preparation of 12'-(4-Piperidinyl)vinblastine Trifluoroacetate

Step 1: 12'-Iodo-3-(tert-butyldimethylsilanyloxy)vinblastine (23 mg, 0.022 mmol), piperidine (5.4 mg, 0.055 mmol), and NaOt-Bu (7.4 mg, 0.077 mmol) were dissolved in anhydrous toluene (1.0 mL) while stirring under argon atmosphere in a sealed tube. The mixture was deoxygenated with argon at room temperature for 3 min then tris(dibenzylideneacetone)dipalladium(0) (2.0 mg, 2.2 μmol) and 2-(dicyclohexylphosphino)-2',4',6'-tri-i-propyl-1,1'-biphenyl (2.1 mg, 4.4 μmol) were added. The reaction vessel was sealed and heated to 80° C. for 4 h. The reaction mixture was cooled to room temperature, diluted with EtOAc, filtered through diatomaceous earth, and then concentrated to provide crude 12'-(1-piperidinyl)-3-(tert-butyldimethylsilanyloxy)vinblastine: ESI MS m/z 1008 [M+H]$^+$.

Step 2: A solution of 12'-(1-piperidinyl)-3-(tert-butyldimethylsilanyloxy)vinblastine (24 mg, 0.023 mmol) in THF (1.0 mL) was treated with tetrabutylammonium fluoride (95 μL of a 1 N solution in THF, 0.095 mmol). After 3 h, the reaction appeared complete as indicated by ESI mass spectral analysis. The reaction mixture was diluted with saturated aqueous NaHCO$_3$ (10 mL) and extracted with CH$_2$Cl$_2$ (2×10 mL). The combined extracts were dried (Na$_2$SO$_4$), concentrated, and purified by reverse phase chromatography (C18, acetonitrile/water, 0.05% trifluoroacetic acid) to provide 12'-(1-piperidinyl)vinblastine trifluoroacetate (6.1 mg, 25%): $^1$H NMR (500 MHz, CD$_3$OD) δ 10.36 (br s, 1H), 7.84 (d, J=2.0 Hz, 1H), 7.47 (d, J=8.5 Hz, 1H), 7.35 (dd, J=8.5, 2.0 Hz, 1H), 6.69 (s, 1H), 6.40 (s, 1H), 5.95-5.92 (m, 1H), 5.68 (d, J=10.5 Hz, 1H), 5.34 (s, 1H), 4.77-4.71 (m, 1H), 3.98-3.81 (m, 9H), 3.77-3.62 (m, 7H), 3.50-3.34 (m, 3H), 3.33-3.19 (m, 3H), 2.89 (dd, J=14.5, 6.0 Hz, 1H), 2.77-2.76 (m, 3H), 2.50-2.46 (m, 1H), 2.37-2.31 (m, 1H), 2.07-1.98 (m, 8H), 1.77-1.35 (m, 13H), 0.97 (t, J=7.5 Hz, 3H), 0.77 (t, J=7.5 Hz, 3H); ESI MS m/z 894 [M+H]$^+$.

Example 86

Preparation of 12'-(4-Morpholino)vinblastine Trifluoroacetate

Step 1: 12'-Iodo-3-(tert-butyldimethylsilanyloxy)vinblastine (23.3 mg, 0.022 mmol), piperidine (6.8 mg, 0.055 mmol), and NaOt-Bu (7.4 mg, 0.077 mmol) were dissolved in anhydrous toluene (1.0 mL) while stirring under argon atmosphere in a sealed tube. The reaction mixture was deoxygenated with argon at room temperature for 3 min then tris(dibenzylideneacetone)dipalladium(0) (2.0 mg, 2.2 μmol) and 2-(dicyclohexylphosphino)-2',4',6'-tri-i-propyl-1,1'-biphenyl (2.1 mg, 4.4 μmol) were added. The reaction mixture was sealed and heated to 80° C. for 4 h. The reaction mixture was cooled to room temperature, diluted with EtOAc, filtered through diatomaceous earth, and then concentrated to provide crude 12'-(4-morpholino)-3-(tert-butyldimethylsilanyloxy)vinblastine: ESI MS m/z 1010 [M+H]$^+$.

Step 2: A solution of 12'-(4-morpholino)-3-(tert-butyldimethylsilanyloxy)vinblastine (24 mg, 0.023 mmol) in THF (1.0 mL) was treated with tetrabutylammonium fluoride (95 μL in a 1 N solution in THF, 0.095 mmol). After 3 h, the reaction appeared complete as indicated by ESI mass spectral analysis. The reaction mixture was diluted with saturated aqueous NaHCO$_3$ (10 mL) and extracted with CH$_2$Cl$_2$ (2×10 mL). The combined extracts were dried (Na$_2$SO$_4$), concentrated, and purified by reverse phase chromatography (C18, acetonitrile/water, 0.05% trifluoroacetic acid) to provide 12'-(4-morpholino)vinblastine trifluoroacetate (5.1 mg, 20: $^1$H NMR (500 MHz, CD$_3$OD) δ 9.91 (br s, 1H), 7.48 (s, 1H), 7.36 (d, J=9.0 Hz, 1H), 7.18 (d, J=7.0 Hz, 1H), 6.88 (s, 1H), 6.42 (s, 1H), 5.93 (dd, J=10.5, 4.5 Hz, 1H), 5.66 (d, J=11.0 Hz, 1H), 5.35 (s, 1H), 4.71-465 (m, 1H), 4.02-3.89 (m, 5H), 3.86 (s, 3H), 3.81 (s, 3H), 3.77-3.71 (m, 2H), 3.69-3.63 (m, 5H), 3.49-3.40 (m, 5H), 3.36-3.18 (m, 6H), 2.88-2.87 (m, 1H), 2.78 (s, 3H), 2.47 (dd, J=16.5, 5.5 Hz, 1H), 2.38-2.32 (m, 1H), 2.07-1.98 (m, 5H), 1.77-1.63 (m, 4H), 1.58-1.51 (m, 2H), 1.43-1.37 (m, 1H), 0.97 (t, J=7.5 Hz, 3H), 0.79 (t, J=7.5 Hz, 3H); ESI MS m/z 896 [M+H]$^+$.

Example 87

Preparation of 12'-(Pyrrolidin-1-yl)vinblastine Trifluoroacetate

Step 1: 12'-Iodo-3-(tert-butyldimethylsilanyloxy)vinblastine (100 mg, 0.10 mmol), pyrrolidine (19 μL, 0.24 mmol), and NaOt-Bu (32 mg, 0.33 mmol) were dissolved in anhydrous toluene (2.0 mL) while stirring under an argon atmosphere in a sealed tube. The reaction mixture was deoxygenated with argon at room temperature for 3 min then tris(dibenzylideneacetone)dipalladium(0) (8.7 mg, 9.5 μmol) and 2-(dicyclohexylphosphino)-2',4',6'-tri-i-propyl-1,1'-biphenyl (9.1 mg, 20 μmol) were added. The reaction mixture was sealed and heated to 80° C. for 2 h. The reaction mixture was cooled to room temperature, diluted with EtOAc, filtered through diatomaceous earth, and then concentrated. Purification of the residue by flash chromatography (silica, 8:1 to 1:1 EtOAc/hexanes) gave 12'-(pyrrolidin-1-yl)-3-(tert-butyldimethylsilanyloxy)vinblastine: ESI MS m/z 994 [M+H]$^+$.

Step 2: A solution of 12'-(pyrrolidin-1-yl)-3-(tert-butyldimethylsilanyloxy)vinblastine (12 mg, 0.012 mmol) in THF (2.0 mL) was treated with tetrabutylammonium fluoride (1 mL of a 1 N solution in THF). After 3 h, the reaction appeared complete as indicated by ESI mass spectral analysis. The reaction mixture was diluted with saturated aqueous NaHCO$_3$ (10 mL) and then extracted with EtOAc (2×10 mL). The combined extracts were dried (Na$_2$SO$_4$) and concentrated. Purification by reverse phase chromatography (C18, acetonitrile/water, 0.05% trifluoroacetic acid) gave 12'-(pyrrolidin-1-yl)vinblastine trifluoroacetate (2 mg, 2%): ESI MS m/z 880 [M+H]$^+$.

Example 88

Preparation of 12'-(Azetidin-1-yl)vinblastine Trifluoroacetate

Step 1: 12'-Iodo-3-(tert-butyldimethylsilanyloxy)vinblastine (716 mg, 0.68 mmol), azetidine (160 μL, 2.3 mmol), and NaOt-Bu (229 mg, 2.38 mmol) were dissolved in anhydrous toluene (5.0 mL) while stirring under argon atmosphere in a sealed tube. The reaction mixture was deoxygenated with argon at room temperature for 3 min then tris(dibenzylideneacetone)dipalladium(0) (62 mg, 68 μmol) and 2-(dicyclohexylphosphino)-2',4',6'-tri-i-propyl-1,1'-biphenyl (64 mg, 140 μmol) were added. The reaction mixture was sealed and heated to 60° C. for 3 h. The reaction mixture was cooled to room temperature, diluted with EtOAc, filtered through diatomaceous earth, and then concentrated: ESI MS m/z 980 [M+H]$^+$.

Step 2: A solution of crude 12'-(azetidin-1-yl)-3-(tert-butyldimethylsilanyloxy)vinblastine in THF (2.0 mL) was treated with tetrabutylammonium fluoride (1 mL in a 1 N solution in THF). After 3 h, the reaction appeared complete as indicated by ESI mass spectral analysis. The reaction mixture was diluted with saturated aqueous NaHCO$_3$ (10 mL) and extracted with EtOAc (2×10 mL). The combined extracts were dried (Na$_2$SO$_4$), concentrated, and purified by reverse phase chromatography (C18, acetonitrile/water, 0.05% trifluoroacetic acid) to provide 12'-(azetidin-1-yl)vinblastine (230 mg, 39%) as a trifluoroacetic acid salt which was converted to an L-tartaric acid salt (200 mg, 64% yield). 12'-(Azetidin-1-yl)vinblastine L-tartaric acid was isolated as a white powder: 1H NMR (500 MHz, CD$_3$OD) δ 7.18-7.13 (m, 1H), 6.62 (s, 1H), 6.54-6.51 (m, 2H), 6.35 (s, 1H), 5.88-5.85 (m, 1H), 5.38-5.32 (m, 2H), 4.58-4.50 (m, 1H), 4.42 (s, 4H), 3.90-3.82 (m, 6H), 3.79-3.75 (m, 3H), 3.69-3.60 (m, 6H), 3.49-3.40 (m, 2H), 3.35-3.27 (m, 4H), 3.26-3.15 (m, 3H), 2.95-2.83 (m, 3H), 2.77-2.70 (m, 4H), 2.46-2.34 (m, 2H), 2.16-2.12 (m, 1H), 2.07-2.05 (m, 3H), 1.93-1.88 (m, 1H), 1.70-1.61 (m, 3H), 1.53-1.48 (m, 2H), 1.47-1.32 (m, 2H), 0.96 (t, J=7.5 Hz, 3H), 0.76 (t, J=7.5 Hz, 3H); ESI MS m/z 866 [M+H]$^+$.

Example 89

Preparation of 12'-(3-Methylpyrazol-1-yl)vinblastine Trifluoroacetate

Step 1: 12'-Iodo-3-(tert-butyl-dimethylsilanyloxy)vinblastine (34 mg, 0.030 mmol), 3-methyl-1H-pyrazole (5.9 μL, 0.070 mmol), and K$_2$CO$_3$ (14 mg, 0.10 mmol) were dissolved in anhydrous toluene (1.0 mL) while stirring under argon atmosphere in a sealed tube. The mixture was deoxygenated with argon at room temperature for 3 min then copper (I) iodide (2.7 mg, 2.9 μmol) and N,N-dimethylethylenediamine (5.6 μL, 10 μmol) were added. The reaction vessel was sealed and the mixture was heated to 80° C. for 2 days. The reaction mixture was cooled to room temperature, diluted with EtOAc, filtered through diatomaceous earth, and then concentrated to provide crude 12'-(3-methylpyrazol-1-yl)-3-(tert-butyldimethylsilanyloxy)vinblastine: ESI MS m/z 1005 [M+H]$^+$.

Step 2: A solution of crude 12'-(3-methylpyrazol-1-yl)-3-(tert-butyldimethylsilanyloxy)vinblastine (30 mg, 0.030 mmol) in THF (1.0 mL) was treated with tetrabutylammonium fluoride (1.2 mL of a 1 N solution in THF, 1.2 mmol). After 5 h, the reaction mixture was diluted with saturated aqueous NaHCO$_3$ (10 mL) and then extracted with CH$_2$Cl$_2$ (2×10 mL). The combined organics were dried (Na$_2$SO$_4$), concentrated, and purified by reverse phase chromatography (C18, acetonitrile/water, 0.05% trifluoroacetic acid) to provide 12'-(3-methylpyrazol-1-yl)vinblastine trifluoroacetate (5.0 mg, 19%): $^1$H NMR (500 MHz, CD$_3$OD) δ 9.92 (br s, 1H), 7.99 (d, J=2.0 Hz, 1H), 7.77 (d, J=2.0 Hz, 1H), 7.44-7.41 (m, 1H), 7.37 (d, J=8.5 Hz, 1H), 6.70 (s, 1H), 6.44 (d, J=2.5 Hz, 1H), 6.29 (d, J=2.0 Hz, 1H), 5.94 (dd, J=10.5, 4.0 Hz, 1H), 5.68 (d, J=10.5 Hz, 1H), 5.36 (d, J=3.0 Hz, 1H), 4.71-4.67 (m, 1H), 3.99-3.90 (m, 3H), 3.87-3.84 (m, 4H), 3.82 (s, 3H), 3.78-3.73 (m, 3H), 3.70-3.65 (m, 4H), 3.51-3.48 (m, 1H), 3.38-3.31 (m, 2H), 3.27-3.16 (m, 3H), 2.91 (dd, J=14.0, 6.0 Hz, 1H), 2.78 (s, 3H), 2.48 (dd, J=15.5, 4.5 Hz, 1H), 2.38-2.34 (m, 4H), 2.08-2.02 (m, 5H), 1.78-1.74 (m, 1H), 1.67-1.66 (m, 1H), 1.60-1.50 (m, 2H), 1.41-1.38 (m, 1H), 0.97 (t, J=7.0 Hz, 3H), 0.82 (t, J=7.5 Hz, 3H); ESI MS m/z 891 [M+H]$^+$.

Example 90

Preparation of 12',13'-Diiodovincristine Trifluoroacetate

An ice cold solution of N-iodosuccinimide (65 mg, 0.288 mmol) in 1:1 trifluoroacetic acid/CH$_2$Cl$_2$ (5.0 mL) was added dropwise over 30 minutes to a solution of vincristine sulfate (188 mg, 0.190 mmol) in 1:1 trifluoroacetic acid/CH$_2$Cl$_2$ (5.0 mL) at 0° C. When the reaction was complete as indicated by HPLC, the reaction mixture was poured into a solution of saturated aqueous NaHCO$_3$ (50 mL) and 10% aqueous NaHSO$_3$ (30 mL) and then extracted with EtOAc (2×30 mL). The combined organics were washed with brine (30 mL), dried over Na$_2$SO$_4$, and evaporated to dryness in vacuo. The residue was purified by reverse phase chromatography (C18, acetonitrile/water, 0.05% trifluoroacetic acid) to provide 12',13' diiodovincristine trifluoroacetate (44 mg, 18%): $^1$H NMR (500 MHz, CD$_3$OD) δ 10.24 (br s, 1H), 8.98 (s, 1H), 8.14 (s, 1H), 7.99 (s, 1H), 7.34 (s, 1H), 6.88-6.64 (m, 1H), 6.00-5.97 (m, 1H), 5.74 (d, J=10 Hz, 1H), 5.18 (s, 1H), 4.67-4.58 (m, 2H), 4.01-3.90 (m, 5H), 3.82-3.66 (m, 8H), 3.59-3.43 (m, 3H), 3.35-3.25 (m, 1H), 3.19-3.15 (m, 3H), 2.88-2.82 (m, 1H), 2.53-2.48 (m, 1H), 2.41-2.38 (m, 1H), 2.04-2.02 (m, 4H), 1.95-1.93 (m, 1H), 1.66-1.63 (m, 3H), 1.55-1.50 (m, 3H), 1.32-1.27 (m, 1H), 0.97-0.95 (m, 3H), 0.82-0.79 (m, 3H); ESI MS m/z 1077 [M+H]$^+$.

Example 91

Preparation of 12',13'-Diiodovinblastine Trifluoroacetate

An ice cold solution of N-iodosuccinimide (112 mg, 0.498 mmol) in 1:1 trifluoroacetic acid/CH$_2$Cl$_2$ (10 mL) was added dropwise over 40 minutes to a solution of vinblastine sulfate (261 mg, 0.249 mmol) in 1:1 trifluoroacetic acid/CH$_2$Cl$_2$ (10 mL) at 0° C. When the reaction was complete as indicated by HPLC, the reaction mixture was poured into a solution of saturated aqueous NaHCO$_3$ (50 mL) and 10% aqueous NaHPO$_3$ (30 mL) and then extracted with EtOAc (2×30 mL). The combined organics were washed with brine (30 mL), dried over Na$_2$SO$_4$, and evaporated to dryness in vacuo. The residue was purified by reverse phase chromatography (C18, acetonitrile/water, 0.05% trifluoroacetic acid) to provide 12',13'-diiodovinblastine trifluoroacetate (79.5 mg, 25%): $^1$H NMR (500 MHz, DMSO-d$_6$) 10.34 (br s, 1H), 8.17 (s, 1H), 7.97 (s, 1H), 6.70 (s, 1H), 6.45 (s, 1H), 5.88 (dd, J=11.0, 5.5 Hz, 1H), 5.68 (d, J=10.5 Hz, 1H), 5.15-5.13 (m, 2H), 4.33-427 (m, 1H), 3.95-3.91 (m, 1H), 3.88-3.77 (m, 7H), 3.73-3.60 (m, 8H), 3.55-3.42 (m, 3H), 3.23-3.05 (m, 3H), 2.83-2.81 (m, 1H), 2.70 (s, 3H), 2.30-2.28 (m, 1H), 2.17-2.15 (m, 1H), 2.03 (s, 3H), 1.83-1.79 (m, 1H), 1.58-1.39 (m, 5H), 1.15-1.12 (m, 1H), 0.85 (t, J=7.0 Hz, 3H), 0.63 (t, J=7.0 Hz, 3H); ESI MS m/z 1063 [M+H]$^+$.

Example 92

Preparation of 13'-Iodo-12'-methylvincristine Trifluoroacetate

A ice cold solution of N-iodosuccinimide (8.2 mg, 0.037 mmol) in 1:1 trifluoroacetic acid/CH$_2$Cl$_2$ (4.0 mL) was added dropwise over 30 minutes to a solution of 12'-methylvincristine (31 mg, 0.37 mmol) in 1:1 trifluoroacetic acid/CH$_2$Cl$_2$ (4.0 mL) at 0° C. When the reaction was complete as indicated by HPLC, the reaction mixture was poured into a solution of saturated aqueous NaHCO$_3$ (50 mL) and 10% aqueous NaHSO$_3$ (30 mL) and the resulting mixture was extracted with EtOAc (2×30 mL). The combined organics were washed with brine (30 mL), dried (Na$_2$SO$_4$), and evaporated to dryness in vacuo. The residue was purified by reverse phase chromatography (C18, acetonitrile/water, 0.05% trifluoroacetic acid) to provide 13'-iodo-12'-methylvincristine trifluoroacetate (6 mg, 17%): $^1$H NMR (500 MHz, DMSO-d$_6$) δ 10.18 (br s, 1H), 9.07 (s, 1H), 7.87 (s, 1H), 7.53 (s, 1H), 7.43 (s, 1H), 6.98 (s, 1H), 5.88 (dd, J=10.0, 4.5 Hz, 1H), 5.58-5.54 (m, 1H), 5.14 (br s, 1H), 5.00 (s, 1H), 4.56 (br s, 1H), 4.39-4.33 (m, 1H), 3.92-3.81 (m, 5H), 3.72-3.45 (m, 10H), 3.21-3.18 (m, 1H), 3.13-3.05 (m, 2H), 2.71-2.68 (m, 1H), 2.51-2.45 (m, 4H), 3.99-3.97 (m, 1H), 2.23-2.18 (m, 2H), 2.00 (s, 3H), 1.77-1.75 (m, 1H), 1.56-1.52 (m, 1H), 1.46-1.40 (m, 5H), 1.08-1.06 (m, 1H), 0.86 (t, J=7.5 Hz, 3H), 0.67 (t, J=7.0 Hz, 3H); ESI MS m/z 965 [M+H]$^+$.

Example 93

Preparation of 12',13'-Dimethylvincristine Trifluoroacetate

Dimethylzinc (0.162 mL of 2.0 M solution in toluene, 0.324 mmol) was added to 12',13'-diiodovincristine (70 mg, 0.064 mmol) and [1,1'-bis(diphenylphosphino)ferrocene] dichloropalladium (II) (9.4 mg, 0.013 mmol) in anhydrous 1,4-dioxane under nitrogen. The reaction mixture was heated to 80° C. for 3 h then quenched by the addition of saturated aqueous NaHCO$_3$ (10 mL). After extraction with CH$_2$Cl$_2$ (2×10 mL), the combined organics were washed with brine (5 mL), dried (Na$_2$SO$_4$), and evaporated to dryness in vacuo. The residue was purified by reverse phase chromatography (C18, acetonitrile/water, 0.05% trifluoroacetic acid) to provide 12',13'-dimethylvincristine trifluoroacetate (12 mg, 21%): $^1$H NMR (500 MHz, CD$_3$OD) δ 9.46 (br s, 1H), 8.98 (s, 1H), 7.33 (s, 1H), 7.25 (s, 1H), 7.11 (s, 1H), 6.95 (d, J=3.0 Hz, 1H), 5.96 (dd, J=10.0, 4.5 Hz, 1H), 5.71 (d, J=10.5, 1H), 5.18 (s, 1H), 4.67 (s, 1H), 4.56-4.48 (m, 1H), 3.95-3.87 (m, 7H), 3.79-3.66 (m, 9H), 3.61-3.56 (m, 1H), 3.48-3.44 (m, 1H), 3.34-3.27 (m, 1H), 3.24-3.15 (m, 2H), 2.83 (dd, J=14.5, 6.5 Hz, 1H), 2.54-2.48 (m, 1H), 2.41-2.29 (m, 7H), 2.08-1.93 (m, 4H), 1.67-1.59 (m, 3H), 1.52-1.45 (m, 3H), 1.33-1.29 (m, 1H), 0.96 (t, J=7.5 Hz, 3H), 0.84 (t, J=7.5 Hz, 3H); ESI MS m/z 853 [C$_{48}$H$_{60}$N$_4$O$_{10}$+H]$^+$.

Example 94

Preparation of 13'-Ethyl-12'-methylvincristine Trifluoroacetate

Diethylzinc (0.074 mL of a 1.0 M solution in toluene, 0.074 mmol) was added to 13'-iodo-12'-methylvincristine (28 mg, 0.029 mmol) and [1,1'-bis(diphenylphosphino)ferrocene] dichloropalladium (II) (21 mg, 0.029 mmol) in anhydrous 1,4-dioxane (1 mL) under nitrogen. The reaction mixture was heated to 80° C. for 2 h then quenched by the addition of saturated aqueous NaHCO$_3$ (3 mL). After extraction with EtOAc (2×5 mL), the combined organics were dried (Na$_2$SO4), and evaporated to dryness in vacuo. The residue was purified by reverse phase chromatography (C18, acetonitrile/water, 0.05% trifluoroacetic acid) to provide 13'-ethyl-12'-methylvincristine trifluoroacetate (5.0 mg, 19%): $^1$H NMR (500 MHz, CD$_3$OD) δ 9.53 (br s, 1H), 8.92 (s, 1H), 7.32 (s, 1H), 7.25 (s, 1H), 7.13 (s, 1H), 6.94 (s, 1H), 5.96 (dd, J=10.4, 5.6 Hz, 1H), 5.70 (d, J=10.4 Hz, 1H), 5.18 (s, 1H), 4.66 (s, 1H), 4.61 (dd, J=18.0, 11.5 Hz, 1H), 3.98-3.87 (m, 6H), 3.75-3.72 (m, 4H), 3.68-3.57 (m, 5H), 3.44-3.27 (m, 3H), 3.20-3.13 (m, 3H), 2.82 (dd, J=7.0, 14.5 Hz, 1H), 2.70-2.64 (m, 2H), 2.51-2.47 (m, 1H), 2.39-2.35 (m, 4H), 2.06-1.91 (m, 4H), 1.67-1.59 (m, 3H), 1.53-1.48 (m, 3H), 1.31-1.28 (m, 1H), 1.18 (t, J=7.5 Hz, 3H), 0.96 (t, J=7.5 Hz, 3H), 0.85 (t, J=7.5 Hz, 3H); ESI MS m/z 867 [M+H]$^+$.

Example 95

Preparation of 12′,13′-Diethylvincristine Trifluoroacetate

Diethylzinc (0.308 mL of a 1.0 M solution in toluene, 0.308 mmol) was added to 12′,13′-diiodovincristine (66 mg, 0.061 mmol) and [1,1′-bis(diphenylphosphino)ferrocene]dichloropalladium (II) (13.5 mg, 0.018 mmol) in anhydrous 1,4-dioxane under nitrogen. The reaction mixture was heated to 80° C. for 30 minutes then quenched by the addition of saturated aqueous NaHCO$_3$ (10 mL). After extraction with CH$_2$Cl$_2$ (2×10 mL), the combined organics were washed with brine (5 mL), dried (Na$_2$SO$_4$), and evaporated to dryness in vacuo. The residue was purified by reverse phase chromatography (C18, acetonitrile/water, 0.05% trifluoroacetic acid) to provide 12′,13′-diethylvincristine trifluoroacetate (25 mg, 36%): $^1$H NMR (500 MHz, DMSO-d$_6$) δ 11.13 (br s, 1H), 9.08 (s, 1H), 7.43 (s, 1H), 7.25 (s, 1H), 7.18 (s, 1H), 7.11 (s, 1H), 5.88 (dd, J=10.5, 5.5 Hz, 1H), 5.59 (d, J=10.5 Hz, 1H), 5.19-5.12 (m, 1H), 5.01 (s, 1H), 4.59 (s, 1H), 4.40-4.35 (m, 1H), 4.05-4.01 (m, 1H), 3.93-3.78 (m, 6H), 3.72-3.62 (m, 5H), 3.56-3.53 (m, 4H), 3.41-3.37 (m, 1H), 3.23-2.18 (m, 1H), 3.12-3.10 (m, 2H), 3.05-3.01 (m, 1H), 2.77-2.57 (m, 4H), 2.29-2.17 (m, 2H), 2.03-2.00 (m, 4H), 1.87-1.82 (m, 1H), 1.56-1.39 (m, 6H), 1.19 (t, J=7.5 Hz, 3H), 1.12 (t, J=7.5 Hz, 3H), 0.70 (t, J=7.5 Hz, 3H), 0.65 (t, J=7.0 Hz, 3H); ESI MS m/z 881 [M+H]$^+$.

Example 96

Preparation of 13′-Acetyl-12′-diethylvincristine Trifluoroacetate

Step 1: 13′-Iodo-12′-methylvincristine (28 mg, 0.030 mmol), copper(I) iodide (0.83 mg, 0.0044 mmol), dichlorobis(triphenylphosphine)palladium (II) (2.0 mg, 0.0029 mmol), toluene (2 mL), and triethylamine (1 mL) were combined in a resealable glass test tube. Argon was bubbled through the solution for 3 min, then (trimethylsilyl)acetylene (24 μL, 0.17 mmol) was added and the mixture was heated at 55° C. for 1 h. Saturated aqueous NaHCO$_3$ (5 mL) was added and the mixture was extracted with ethyl acetate (3×5 mL). The combined organics were washed with brine (5 mL), dried over Na$_2$SO$_4$, and evaporated to dryness in vacuo to yield crude 12′-methyl-13′-trimethylsilanylethynylvincristine: ESI MS m/z 935 [M+H]$^+$.

Step 2: Crude 12′-methyl-13′-trimethylsilanylethynylvincristine (27 mg, 0.028 mmol) was added to a solution of CH$_2$Cl$_2$ (1 mL) and trifluoroacetic acid (1 mL). The reaction was monitored by ESI MS. After 30 min, the reaction mixture was poured into a solution of saturated aqueous NaHCO$_3$ (50 mL) and the resulting mixture was extracted with EtOAc (2×30 mL). The combined organics were washed with brine (30 mL), dried (Na$_2$SO$_4$), and evaporated to dryness in vacuo.

The residue was purified by reverse phase chromatography (C18, acetonitrile/water, 0.05% trifluoroacetic acid) to provide 13′-acetyl-12′-methylvincristine trifluoroacetate (6 mg, 17%): $^1$H NMR (500 MHz, CD$_3$OD) δ 10.24 (br s, 1H), 8.99 (s, 1H), 7.90 (s, 1H), 7.39 (s, 1H), 7.35 (s, 1H), 6.95 (s, 1H), 5.97 (dd, J=10.0, 4.5 Hz, 1H), 5.73 (d, J=10.0 Hz, 1H), 5.19 (s, 1H), 4.68-4.66 (m, 2H), 4.02-3.91 (m, 6H), 3.84-3.74 (m, 5H), 3.71-3.62 (m, 5H), 3.51-3.48 (m, 1H), 3.37-3.25 (m, 2H), 3.17 (br s, 2H), 2.85 (dd, J=14.5, 6.0 Hz, 1H), 2.60 (m, 7H), 2.39-2.36, (m, 1H), 2.08-1.94 (m, 4H), 1.68-1.49 (m, 6H), 1.33-1.28 (m, 1H), 0.96 (t, J=7.5 Hz, 3H), 0.85 (t, J=7.0 Hz, 3H); ESI MS m/z 881 [M+H]$^+$.

Example 97

Preparation of 12′-Bromoanhydrovinblastine

To an ice cold solution of 12′-bromovinblastine (0.1 g, 0.09 mmol) in DMF (1 mL) was added thionyl chloride (0.04 mL, 0.45 mmol) and the mixture stirred for 2 hours. The reaction mixture was diluted with 5% LiCl (aq) and extracted with dichloromethane (3×). The organic layer was concentrated under reduced pressure and the residue dried under high vacuum. Purification by column chromatography (silica, 94:4 CHCl$_3$/MeOH) followed by reversed phase chromatography (C18, acetonitrile/water, 0.05% concentrated ammonium hydroxide) gave 12′-bromoanhydrovinblastine (26 mg, 26%): $^1$H NMR (300 MHz, CDCl$_3$) δ 7.62 (d, J=1 Hz, 1H), 7.22 (dd, J=9, 1 Hz, 1H), 6.98 (d, J=8 Hz, 1H), 6.49 (s, 1H), 6.11 (s, 1H), 5.86 (dd, J=10, 4 Hz, 1H), 5.45 (m, 1H), 5.45 (s, 1H), 5.30 (d, J=10 Hz, 1H), 3.81 (s, 3H), 3.81 (m, 2H), 3.79 (s, 3H), 3.73 (s, 1H), 3.64 (s, 3H), 3.53 (m, 1H), 3.45-3.05 (m, 4H), 3.00 (m, 2H), 2.80 (m, 2H), 2.71 (s, 3H), 2.62 (s, 1H), 2.42 (m, 2H), 2.13 (m, 1H), 2.11 (s, 3H), 2.03 (s, 1H), 1.93 (q, J=7 Hz, 2H), 1.76 (obs m), 1.21 (m, 2H), 0.9 (t, J=7 Hz, 3H), 0.77 (t, J=7 Hz, 3H); ESI MS m/z 871, 873 [M+H]$^+$.

Example 98

Preparation of 12′-Iodoanhydrovinblastine

12′-iodoanhydrovinblastine was prepared from 12′-iodovinblastine following the procedure described in Example 98 and was used without purification, yield (0.25 g, quant.): $^1$H NMR (free base, 300 MHz, MeOD) δ 7.34 (s, 1H), 7.33 (d, J=8 Hz, 1H), 7.01 (d, J=8 Hz, 1H), 6.56 (s, 1H), 6.33 (s, 1H), 5.85 (dd, J=10, 4 Hz, 1H), 5.49 (m, 1H), 5.35 (s, 1H), 5.30 (m, 1H), 4.61 (m, 1H), 3.90-3.55 (m, 7H), 3.83 (s, 3H), 3.76 (s, 3H), 3.65 (s, 3H), 3.60 (s, 1H), 3.45 (d, J=16 Hz, 1H), 3.10-3.37 (m, 4H), 2.88 (dd, J=14, 5 Hz, 1H), 2.73 (s, 3H), 2.47 (d, J=16 Hz, 1H), 2.32 (m, 1H), 2.02 (s, 3H), 2.00 (m, 1H), 1.45-1.80 (m, 6H), 1.02 (t, J=7 Hz, 3H), 0.72 (t, J=7 Hz, 3H); ESI m/z 919 [M+H]$^+$.

Example 99

Preparation of 12′-Bromoanhydrovincristine

12′-bromoanhydrovincristine was prepared from 12′-bromovincristine and purified following the procedure described in Example 98, yield (32 mg, 23%).

$^1$H NMR (300 MHz, MeOD) δ 8.89 (s, 1H), 7.52 (s, 1H), 7.18 (s, 1H), 7.10 (m, 2H), 6.82 (s, 1H), 5.82 (dd, J=10, 4 Hz, 1H), 5.40 (m, 1H), 5.43-5.30 (m, 2H), 5.07 (s, 1H), 4.52 (s, 1H), 3.85 (s, 3H), 3.62 (t, J=10 Hz, 1H), 3.61 (s, 3H), 3.55 (s, 3H), 3.40-3.08 (m), 3.08-2.87 (m, 3H), 2.80 (d, J=16 Hz, 1H), 2.56 (m, 1H), 2.38 (m, 2H), 1.93 (s, 3H), 1.89 (q, J=8 Hz, 2H), 1.70 (m, 2H), 1.42 (m, 2H), 1.22 (m, 2H), 0.94 (t, J=8 Hz, 3H), 0.64 (t, J=7 Hz, 3H); ESI m/z 885, 887 [M+H]$^+$.

Example 100

Description of Biological Assays

A. HeLa GI$_{50}$ Determinations

Growth inhibition (GI$_{50}$) values were measured on the human cervical carcinoma cell line, HeLa S-3, which were selected for growth on plastic. The HeLa cell assay was based on the description of Skehan et al., *J Natl. Cancer Inst.*, 82:1107-12 (1990), which is hereby incorporated by reference in its entirety. HeLa cells were plated at 2×10$^4$ cells/well in 96 well plates. One day later, a control plate was fixed by the addition of TCA to 5%. After five rinses with tap water, the plate was air-dried and stored at 4° C. Test compounds were added to the remaining plates at 10-fold dilutions. Two days later, all plates were fixed as described above. Cells were then stained by the addition of 100 μL per well of 0.4% sulforhodamine B (SRB) in 1% acetic acid for 30 min at 4° C. Wells were then quickly rinsed 5× with 1% acetic acid and allowed to air dry. The SRB was then solubilized by the addition of 100 μL per well of unbuffered 10 mM Tris base. Dye was quantified by measuring absorbance at 490 nm on a Molecular Devices microplate reader. Growth inhibition was calculated according to the following equation: GI=100×(T−T$_0$)/(C−T$_0$), where the optical density (OD) of the test well after 2 days of treatment was T, the OD of the wells in the control plate on day 0 was T$_0$ and C was the OD of untreated wells. Plots of percent growth inhibition versus inhibitor concentration were used to determine the GI$_{50}$.

B. MCF-7 GI$_{50}$ Determinations

Growth inhibition (GI$_{50}$) values were measured on the human breast carcinoma line, MCF-7. MCF-7 cells were plated at 2×10$^4$ cells/well in 96 well plates and grown for 24 hours in drug free media. On day 2, test compounds were added to the plates at 10-fold dilutions. Four days later, cells were fixed by the addition of glutaraldehyde to 0.75%. After 30 min, the fixed cells were extensively rinsed with distilled water and dried at room temperature for one hour. The cells were then stained with a 0.2% crystal violet solution for one hour at room temperature. Unbound stain was removed by ten rinses with tap water and plates were allowed to air dry for 30 min. The crystal violet was then solubilized by the addition of 10% acetic acid for 15 min and quantified by measuring absorbance at 570 nm on a Molecular Devices microplate reader. Growth inhibition was calculated according to the following equation: GI=100×(T/T$_0$), where the optical density (OD) of the test well after 4 days of treatment was T, the OD of the wells in the control plate on day 0 was T$_0$. Plots of percent growth inhibition versus inhibitor concentration were used to determine the GI$_{50}$.

TABLE 3

Growth Inhibition (GI$_{50}$) of HeLa Cells for Compounds of the Current Invention.

| Example | HeLa Cells GI$_{50}$ (nM) | MCF-7 Cells GI$_{50}$ (nM) |
|---|---|---|
| 5 | 50 | 30 |
| 6 | 400 | 300 |
| 7 | 400 | 100 |
| 8 | ND | ND |
| 9 | 300 | 500 |
| 10 | 250 | 95 |
| 11 | 300 | 300 |
| 12 | 200 | 300 |
| 13 | >1000 | 600 |
| 14 | 300 | 300 |
| 15 | 200 | 100 |
| 16 | 300 | 40 |
| 17 | ND | ND |
| 18 | 300 | 300 |
| 19 | >1000 | 800 |
| 20 | 500 | >1000 |
| 21 | 300 | 300 |
| 22 | 300 | 300 |
| 23 | 40 | 50 |
| 24 | 300 | 400 |
| 25 | 3 | 9 |
| 26 | 165 | 70 |
| 27 | 200 | 300 |
| 28 | 100 | 300 |
| 29 | 515 | 515 |
| 30 | 65 | 45 |
| 31 | 600 | 300 |
| 32 | 35 | 30 |
| 33 | 20 | 30 |
| 35 | 200 | 60 |
| 36 | 30 | 50 |
| 37 | 100 | 200 |
| 38 | 100 | 200 |
| 39 | 25 | 25 |
| 40 | 6 | 8 |
| 41 | 2 | 3 |
| 42 | 3 | 3 |
| 43 | 0.6 | 2 |
| 44 | 70 | 100 |
| 45 | 50 | 200 |
| 46 | 200 | 500 |
| 47 | 20 | 40 |
| 48 | 30 | 40 |
| 49 | 8 | 30 |
| 50 | 20 | 40 |
| 52 | 200 | 300 |
| 53 | 20 | 30 |
| 54 | 100 | 50 |
| 55 | 19 | 6 |
| 56 | 30 | 30 |
| 57 | 300 | 300 |
| 58 | 200 | 100 |
| 59 | 300 | 300 |
| 60 | 10 | 20 |
| 61 | 3 | 3 |
| 62 | 10 | 30 |
| 63 | 40 | 60 |
| 64 | 900 | >1000 |
| 65 | 3 | 3 |
| 66 | 10 | 4 |
| 67 | 20 | 30 |
| 68 | 30 | 200 |
| 69 | 600 | >1000 |
| 70 | 200 | 100 |
| 71 | 200 | 100 |
| 72 | 40 | 50 |
| 73 | 200 | 300 |
| 74 | 30 | 40 |
| 75 | 0.3 | 0.3 |
| 76 | 1 | 3 |
| 77 | 0.3 | 0.6 |
| 78 | 5 | 10 |
| 79 | 700 | >1000 |
| 80 | 200 | 200 |
| 81 | 30 | 50 |
| 82 | 300 | 600 |
| 83 | 300 | 500 |

TABLE 3-continued

Growth Inhibition (GI$_{50}$) of HeLa Cells for Compounds of the Current Invention.

| Example | HeLa Cells GI$_{50}$ (nM) | MCF-7 Cells GI$_{50}$ (nM) |
|---|---|---|
| 84 | 30 | 500 |
| 85 | 20 | 30 |
| 86 | 30 | 50 |
| 87 | 50 | 60 |
| 90 | 30 | 30 |
| 91 | 60 | 200 |
| 92 | 30 | 30 |
| 93 | 20 | 30 |
| 94 | 30 | 50 |
| 95 | 20 | 30 |
| 96 | 300 | 600 |
| 97 | 30 | 50 |
| 98 | 50 | 305 |
| 99 | 4 | 1 |

D. NCI Sixty Cell Line Data

The following data in Table 4 summarize the growth inhibition properties of several compounds of the present invention against 60-human transformed cell lines. These data were cooperatively obtained at the National Cancer Institute in their 60-cell line growth inhibition assay according to published procedures (Boyd, M. R., "Anticancer Drug Development Guide," *Preclinical Screening, Clinical Trials, and Approval*; Teicher, B. Ed.; Humana Press; Totowa, N.J., 23-42 (1997), which is hereby incorporated by reference).

TABLE 4

In Vitro Growth Inhibition (GI$_{50}$) of NCI Human Transformed Cell Lines of Several Compounds of the Current Invention.

| Cancer Type | Cell Line | 17 GI$_{50}$ (nM) | 19 GI$_{50}$ (nM) | 29 GI$_{50}$ (nM) | 97 GI$_{50}$ (nM) |
|---|---|---|---|---|---|
| Breast | BT-549 | <10 | 1890 | — | — |
| Breast | HS 578T | <10 | 1850 | 628 | <10 |
| Breast | MCF7 | <10 | 396 | 10.5 | <10 |
| Breast | MDA-MB-231/ATCC | <10 | 2020 | <10 | <10 |
| Breast | MDA-MB-435 | <10 | 60.5 | 34.3 | <10 |
| Breast | NCI/ADR-RES | 2090 | 1440 | 18100 | 77.9 |
| Breast | T-47D | — | 4750 | — | 19400 |
| CNS | SF-268 | — | 731 | 901 | <10 |
| CNS | SF-295 | <10 | 293 | 568 | <10 |
| CNS | SF-539 | <10 | 1790 | 21 | <10 |
| CNS | SNB-19 | <10 | 1790 | <10 | <10 |
| CNS | SNB-75 | <10 | 530 | — | 12200 |
| CNS | U251 | <10 | 9970 | <10 | <10 |
| Colon | COLO 205 | <10 | 1190 | <10 | <10 |
| Colon | HCC-2998 | <10 | 182 | <10 | <10 |
| Colon | HCT-116 | <10 | 300 | <10 | <10 |
| Colon | HCT-15 | 44 | 8350 | 274 | <10 |
| Colon | HT29 | <10 | 423 | <10 | <10 |
| Colon | KM12 | <10 | 206 | 212 | <10 |
| Colon | SW-620 | <10 | 1770 | 1300 | <10 |
| Leukemia | CCRF-CEM | — | 263 | 28.8 | <10 |
| Leukemia | HL-60(TB) | — | — | 244 | <10 |
| Leukemia | K-562 | 53.1 | — | <10 | <10 |
| Leukemia | MOLT-4 | <10 | 196 | 11 | <10 |
| Leukemia | RPMI-8226 | — | 252 | 14.1 | <10 |
| Leukemia | SR | — | — | 396 | — |
| Melanoma | LOX IMVI | <10 | >100000 | <10 | <10 |
| Melanoma | M14 | <10 | 260 | <10 | <10 |
| Melanoma | MALME-3M | <10 | 254 | — | 1420 |
| Melanoma | SK-MEL-2 | <10 | 2290 | 9770 | — |
| Melanoma | SK-MEL-28 | — | 1270 | — | 3310 |
| Melanoma | SK-MEL-5 | <10 | 757 | 420 | <10 |
| Melanoma | UACC-257 | 22400 | 46000 | 19300 | 3950 |
| Melanoma | UACC-62 | <10 | 2040 | <10 | <10 |
| Non-Small Cell Lung | A549/ATCC | 16.9 | 37300 | 28.7 | <10 |
| Non-Small Cell Lung | EKVX | <10 | 2790 | 10800 | 10200 |
| Non-Small Cell Lung | HOP-62 | <10 | 571 | <10 | <10 |
| Non-Small Cell Lung | HOP-92 | 160 | 335 | 9930 | 12200 |
| Non-Small Cell Lung | NCI-H226 | — | — | <10 | <10 |
| Non-Small Cell Lung | NCI-H23 | <10 | 541 | — | 325 |
| Non-Small Cell Lung | NCI-H322M | <10 | 429 | 955 | — |
| Non-Small Cell Lung | NCI-H460 | <10 | 353 | 176 | <10 |
| Non-Small Cell Lung | NCI-H522 | <10 | 1810 | 31.4 | <10 |

TABLE 4-continued

In Vitro Growth Inhibition ($GI_{50}$) of NCI Human Transformed Cell Lines of Several Compounds of the Current Invention.

| Cancer Type | Cell Line | 17 $GI_{50}$ (nM) | 19 $GI_{50}$ (nM) | 29 $GI_{50}$ (nM) | 97 $GI_{50}$ (nM) |
|---|---|---|---|---|---|
| Ovarian | IGROV1 | — | 2210 | 1710 | <10 |
| Ovarian | OVCAR-3 | <10 | 207 | 59.7 | <10 |
| Ovarian | OVCAR-4 | 15.3 | 1550 | 21.1 | — |
| Ovarian | OVCAR-5 | <10 | 1780 | — | 12.4 |
| Ovarian | OVCAR-8 | <10 | 32200 | 22.6 | <10 |
| Ovarian | SK-OV-3 | <10 | 1880 | 16.9 | <10 |
| Prostate | DU-145 | <10 | 2460 | 15.2 | <10 |
| Prostate | PC-3 | <10 | 280 | 44.2 | <10 |
| Renal | 786-0 | <10 | 889 | <10 | <10 |
| Renal | A498 | <10 | — | — | — |
| Renal | ACHN | <10 | 22000 | 93.7 | 64.1 |
| Renal | CAKI-1 | 73.4 | 557 | 1200 | 589 |
| Renal | RXF393 | <10 | 619 | 268 | — |
| Renal | SN12C | <10 | 2470 | <10 | <10 |
| Renal | TK-10 | <10 | 313 | 3240 | <10 |
| Renal | UO-31 | 98.6 | 2200 | — | — |
| Renal | RPMI-8226 | — | 252 | 14.1 | <10 |

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method for treating a condition selected from the group consisting of leukemia, carcinoma of the breast, lymphosarcoma, ovarian cancer, squamous cell cancer of the lung, and Hodgkin's disease in mammals comprising:
administering to a mammal a therapeutically effective amount of the compound of Formula (I) as follows:

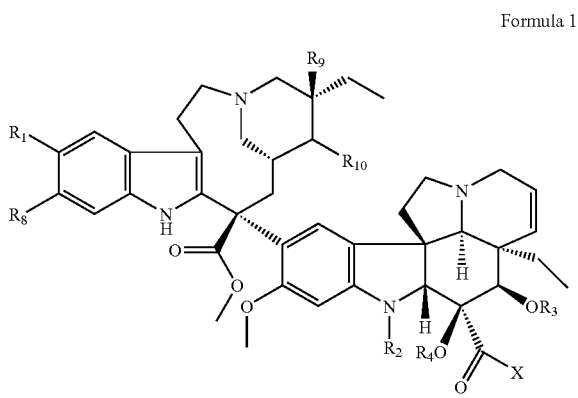

Formula 1 where:
$R_1$ is:
  alkyl;
  alkenyl;
  alkynyl;
  aryl;
  3-methylpyrazol-1-yl;
  pyridyl;
  thienyl;
  thiazolyl;
  piperidinyl;
  morpholinyl;
  pyrrolidinyl;
  azetidinyl;
  Cl;
  Br;
  F;
  CN;
  $C(O)NR_5R_6$;
  $C(O)NHR_5$;
  $C(O)NH_2$;
  $C(O)NHNH_2$;
  $C(O)NR_5NH_2$;
  $C(O)NR_5NHR_6$;
  $C(O)NR_5NR_6R_7$;
  $C(O)NHNHR_5$;
  $C(O)NHNR_5R_6$;
  $C(O)NHOH$;
  $SO_2NHNH_2$;
  $SO_2NR_5NH_2$;
  $SO_2NR_5NHR_6$;
  $SO_2NR_5NR_6R_7$;
  $SO_2NHNHR_5$;
  $SO_2NHNR_5R_6$;
  $CO_2R_5$;
  $SR_5$;
  $SSR_5$;
  $SO_2NHR_5$;
  $SO_2NR_5R_6$;
  $B(OR_5)_2$;
  $CF_3$;
  SH;
  $SO_2NH_2$;
  $NH_2$;
  $NHR_5$;
  $NHSO_2R_5$;
  $NR_5R_6$;
  $NHCOR_5$;
  $NR_5COR_6$; or
  $NR_5SO_2R_6$;
$R_2$ = alkyl or CH(O);
$R_3$ = hydrogen, alkyl, or $C(O)R_5$;
$R_4$ = hydrogen or $C(O)R_5$;
$R_5$, $R_6$ and $R_7$ each are independently alkyl, alkenyl, alkynyl, or aryl;
$R_8$ = hydrogen, halogen, alkyl, alkenyl, alkynyl, aryl, acyl, or thioalkyl;
$R_9$=OH and $R_{10}$=H or $R_9$ and $R_{10}$ together form a bridging double bond;

$R_5$ and $R_6$ can form a ring or $R_6$ and $R_7$ can form a ring; $X=OR_5$, $NR_5R_6$, $NHNH_2$, $NHNHC(O)R_5$, $OH$, $NHR_5$, $NH_2$, or $NHNHC(O)H$;

$R_4$ and X can be linked together with intervening atoms to form a ring; $R_1$ and $R_8$ can be linked together; or a pharmaceutically acceptable salt thereof, wherein the alkyl and alkenyl groups can be branched or straight, with the proviso, that when $R_8=H$, $R_9=OH$, and $R_{10}=H$, then $R_1 \neq Br$ and the proviso that if $R_1$ is an unsubstituted aryl, then $R_2 \neq CH_3$.

2. The method according to claim 1, wherein $R_3$=acetyl.

3. The method according to claim 1, wherein $R_4$=hydrogen.

4. The method according to claim 1, wherein X=OMe.

5. The method according to claim 1, wherein $R_3$=acetyl, $R_4$=hydrogen, and X=OMe.

6. The method according to claim 1, wherein $R_2$=CH(O).

7. The method according to claim 1, wherein $R_2$=alkyl.

8. The method of claim 1, wherein the mammal is human.

9. The method according to claim 1, wherein the compound has the following chemical formula:

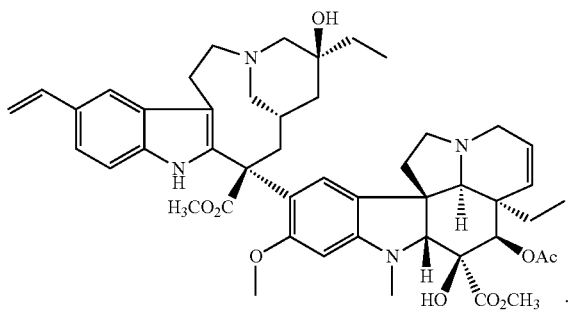

10. The method according to claim 1, wherein the compound has the following chemical formula:

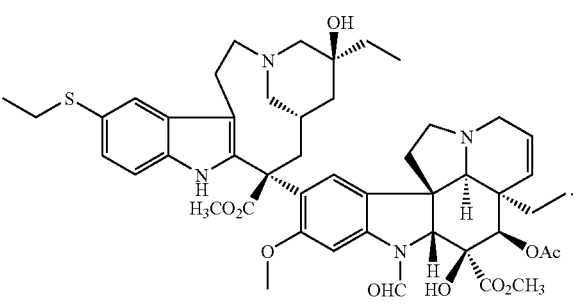

11. The method according to claim 1, wherein the compound has the following chemical formula:

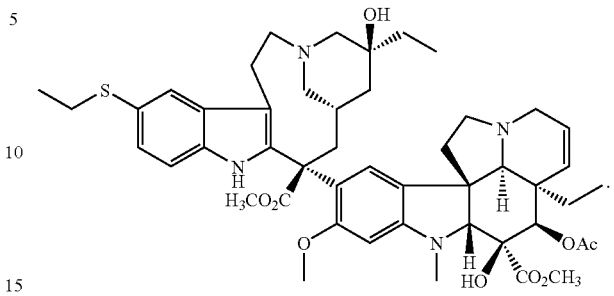

12. The method according to claim 1, wherein the compound has the following chemical formula:

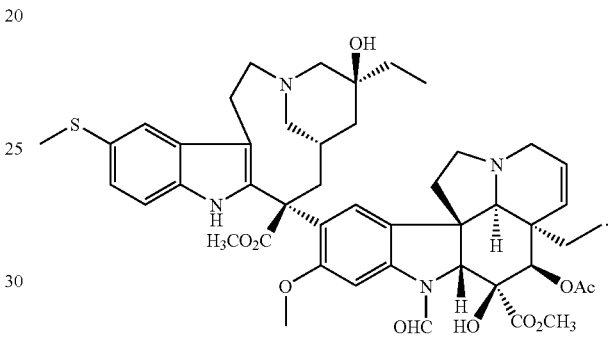

13. The method according to claim 1, wherein the compound has the following chemical formula:

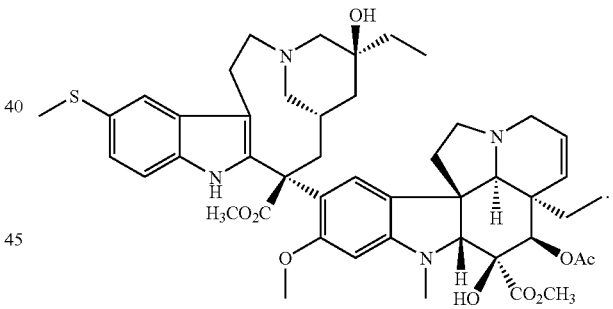

14. The method according to claim 1, wherein the compound has a substituted form of $R_1$ with the following chemical formula:

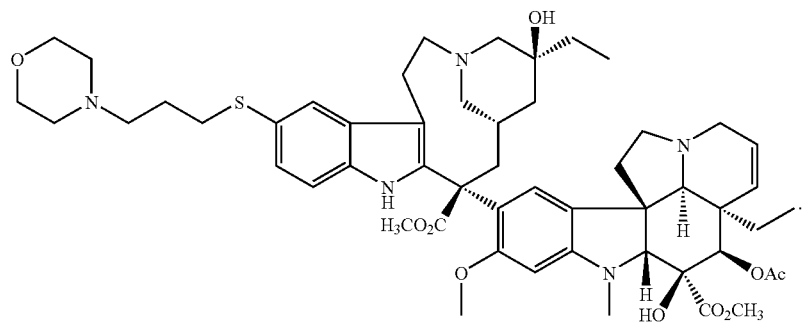

15. The method according to claim 1, wherein the compound has a substituted form of $R_1$ with the following chemical formula:

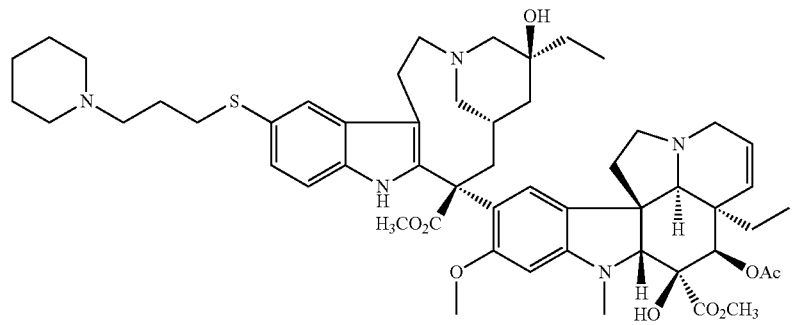

16. The method according to claim 1, wherein the compound has a substituted form of $R_1$ with the following chemical formula:

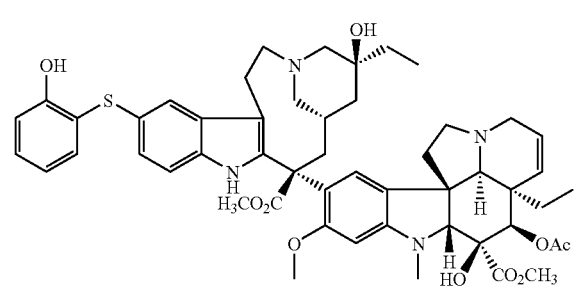

17. The method according to claim 1, wherein the compound has the following chemical formula:

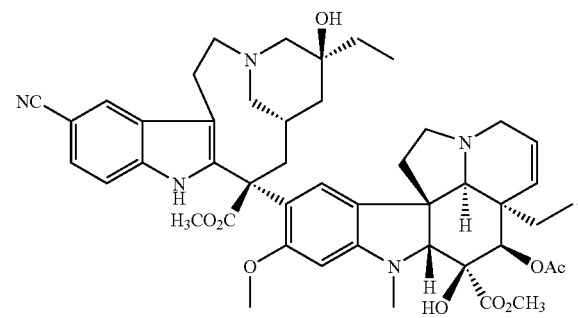

18. The method according to claim 1, wherein the compound has the following chemical formula:

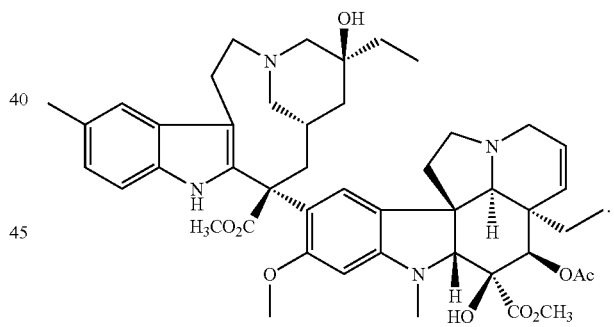

19. The method according to claim 1, wherein the compound has the following chemical formula:

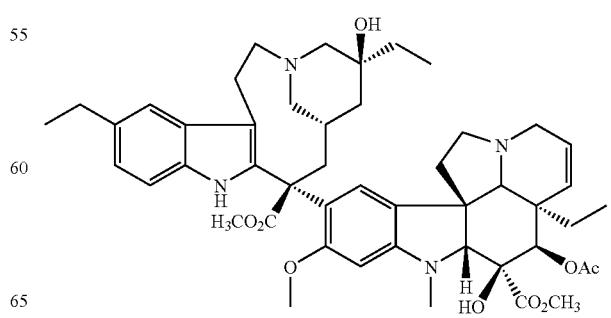

20. The method according to claim 1, wherein the compound has the following chemical formula:

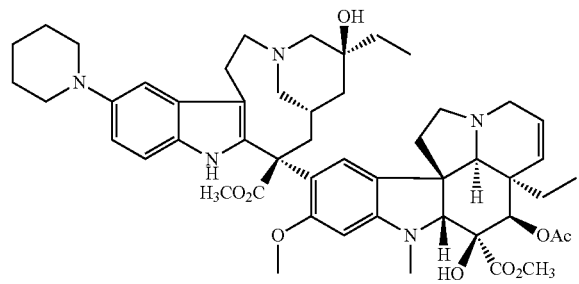

21. A method for treating a condition selected from the group consisting of leukemia, carcinoma of the breast, lymphosarcoma, ovarian cancer, squamous cell cancer of the lung, and Hodgkin's disease in mammals comprising:
administering to a mammal a therapeutically effective amount of a compound having the following chemical formula:

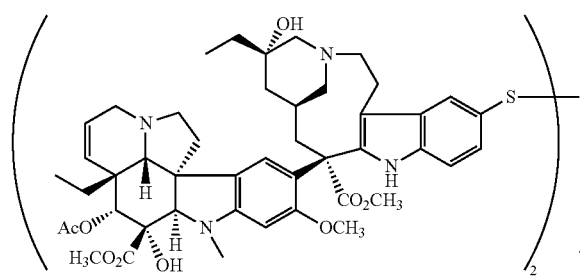

22. A method for treating a condition selected from the group consisting of leukemia, carcinoma of the breast, lymphosarcoma, ovarian cancer, squamous cell cancer of the lung, and Hodgkin's disease in mammals comprising:
administering to a mammal a therapeutically effective amount of a compound having the following chemical formula:

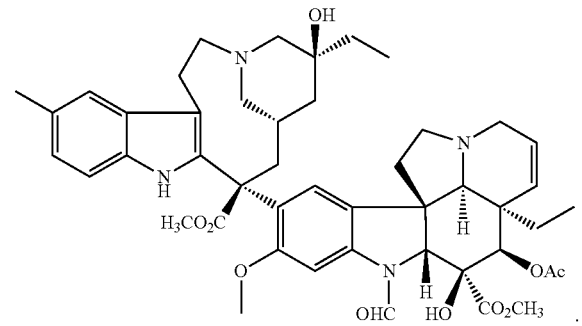

23. A method for treating a condition selected from the group consisting of leukemia, carcinoma of the breast, lymphosarcoma, ovarian cancer, squamous cell cancer of the lung, and Hodgkin's disease in mammals comprising:
administering to a mammal a therapeutically effective amount of a compound having the following chemical formula:

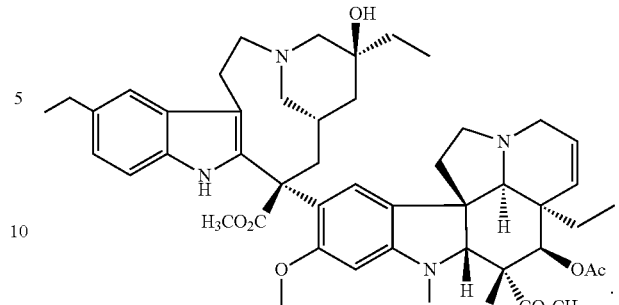

24. A method for treating a condition selected from the group consisting of leukemia, carcinoma of the breast, lymphosarcoma, ovarian cancer, squamous cell cancer of the lung, and Hodgkin's disease in mammals comprising:
administering to a mammal a therapeutically effective amount of a compound having the following chemical formula:

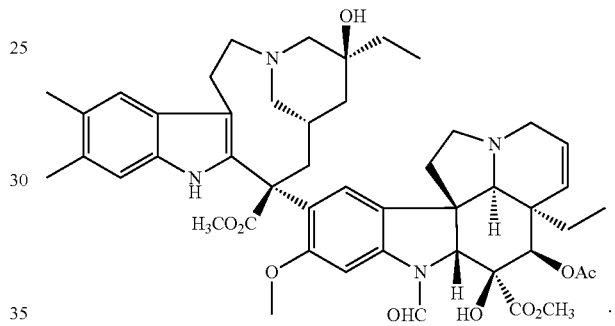

25. A method for treating a condition selected from the group consisting of leukemia, carcinoma of the breast, lymphosarcoma, ovarian cancer, squamous cell cancer of the lung, and Hodgkin's disease in mammals comprising:
administering to a mammal a therapeutically effective amount of a compound having the following chemical formula:

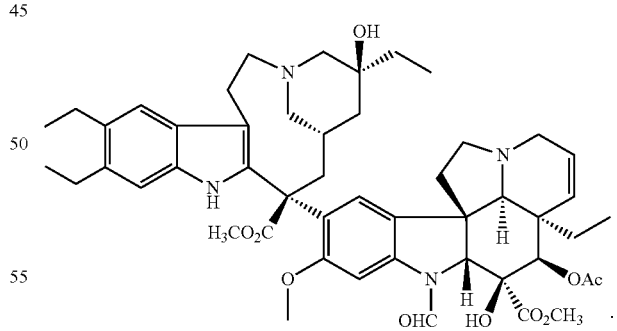

26. A method for treating a condition selected from the group consisting of choricarcinoma, neuroblastoma, acute lung organs leukemia, chronic lung organs leukemia, testicular cancers, non-Hodgkin's lymphoma, acute childhood leukemia, lymphatic leukemia, Wilm's tumor, rhabdosarcoma, reticulum cell sarcoma, melanoma, and squamous cell cancer of the cervix in mammals comprising:
administering to a mammal a therapeutically effective amount of the compound of Formula (I) as follows:

Formula I

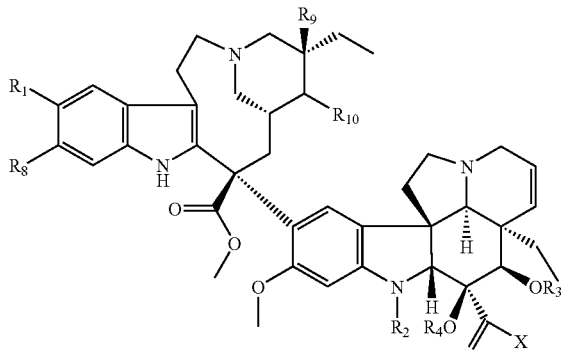

where:
R₁ is:
  alkyl;
  alkenyl;
  alkynyl;
  aryl;
  3-methylpyrazol-1-yl;
  pyridyl;
  thienyl;
  thiazolyl;
  piperidinyl;
  morpholinyl;
  pyrrolidinyl;
  azetidinyl;
  Cl;
  Br;
  F;
  CN;
  C(O)NR₅R₆;
  C(O)NHR₅;
  C(O)NH₂;
  C(O)NHNH₂;
  C(O)NR₅NH₂;
  C(O)NR₅NHR₆;
  C(O)NR₅NR₆R₇;
  C(O)NHNHR₅;
  C(O)NHNR₅R₆;
  C(O)NHOH;
  SO₂NHNH₂;
  SO₂NR₅NH₂;
  SO₂NR₅NHR₆;
  SO₂NR₅NR₆R₇;
  SO₂NHNHR₅;
  SO₂NHNR₅R₆;
  CO₂R₅;
  SR₅;
  SSR₅;
  SO₂NHR₅;
  SO₂NR₅R₆;
  B(OR₅)₂;
  CF₃;
  SH;
  SO₂NH₂;
  NH₂;
  NHR₅;
  NHSO₂R₅;
  NR₅R₆;
  NHCOR₅;
  NR₅COR₆; or
  NR₅SO₂R₆;
R₂=alkyl or CH(O);
R₃=hydrogen, alkyl, or C(O)R₅;
R₄=hydrogen or C(O)R₅;
R₅, R₆ and R₇ each are independently alkyl, alkenyl, alkynyl, or aryl;
R₈=hydrogen, halogen, alkyl, alkenyl, alkynyl, aryl, acyl, or thioalkyl;
R₉=OH and R₁₀=H or R₉ and R₁₀ together form a bridging double bond;
R₅ and R₆ can form a ring or R₆ and R₇ can form a ring;
X=OR₅, NR₅R₆, NHNH₂, NHNHC(O)R₅, OH, NHR₅, NH₂, or NHNHC(O)H;
R₄ and X can be linked together with intervening atoms to form a ring; R₁ and R₈ can be linked together; or a pharmaceutically acceptable salt thereof, wherein the alkyl and alkenyl groups can be branched or straight, with the proviso, that when R₈=H, R₉=OH, and R₁₀=H, then R₁≠Br and the proviso that if R₁ is an unsubstituted aryl, then R₂≠CH₃.

27. The method according to claim 26, wherein R₃=acetyl.

28. The method according to claim 26, wherein R₄=hydrogen.

29. The method according to claim 26, wherein X=OMe.

30. The method according to claim 26, wherein R₃=acetyl, R₄=hydrogen, and X=OMe.

31. The method according to claim 26, wherein R₂=CH(O).

32. The method according to claim 26, wherein R₂=alkyl.

33. The method of claim 26, wherein the mammal is human.

34. The method according to claim 26, wherein the compound has the following chemical formula:

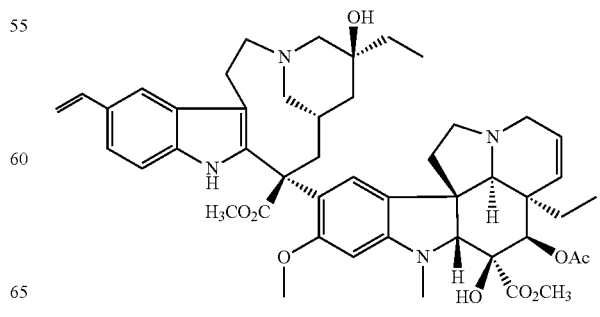

35. The method according to claim 26, wherein the compound has the following chemical formula:

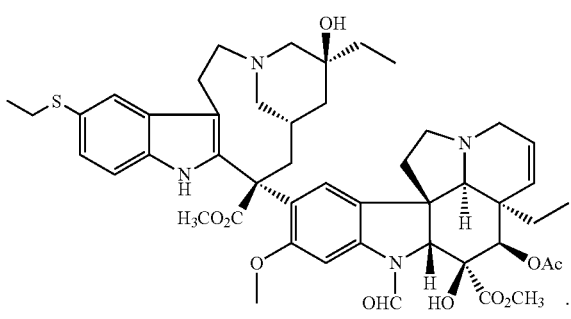

36. The method according to claim 26, wherein the compound has the following chemical formula:

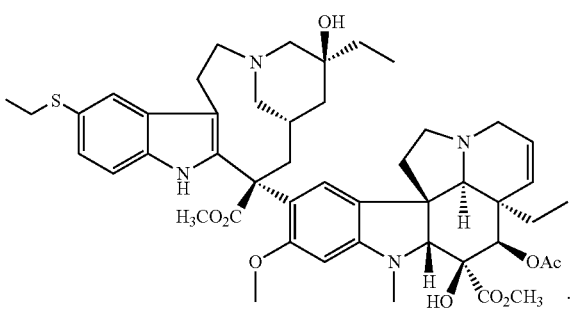

37. The method according to claim 26, wherein the compound has the following chemical formula:

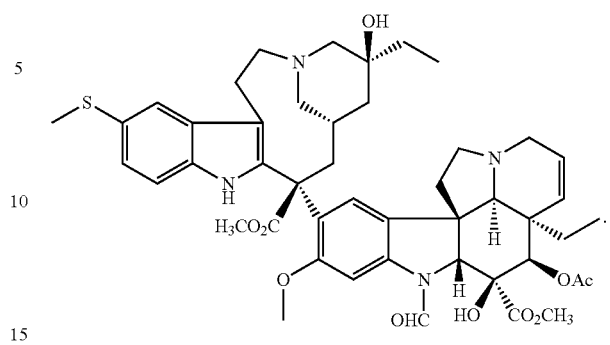

38. The method according to claim 26, wherein the compound has the following chemical formula:

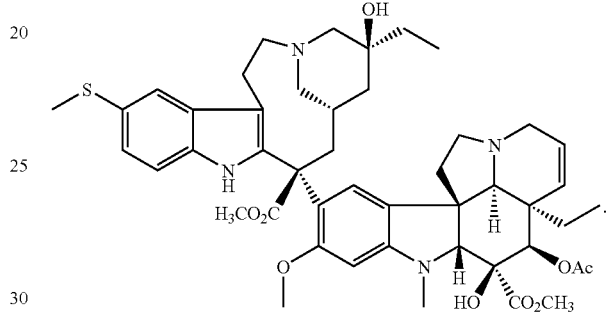

39. The method according to claim 26, wherein the compound has a substituted form of $R_1$ with the following chemical formula:

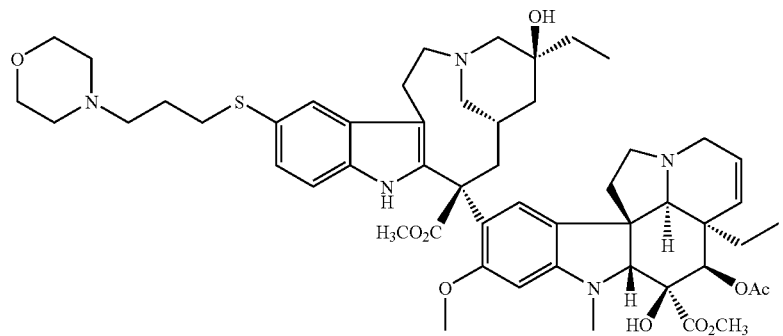

40. The method according to claim 26, wherein the compound has a substituted form of $R_1$ with the following chemical formula:

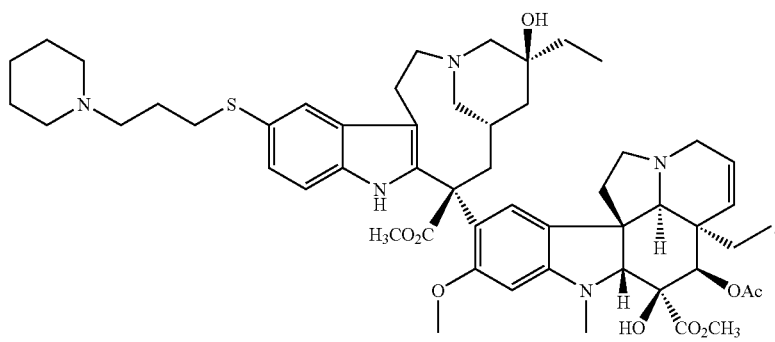

41. The method according to claim 26, wherein the compound has a substituted form of $R_1$ with the following chemical formula:

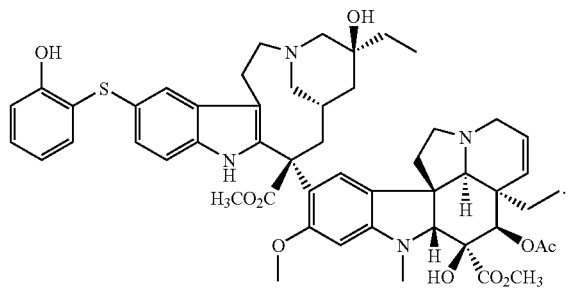

42. The method according to claim 26, wherein the compound has the following chemical formula:

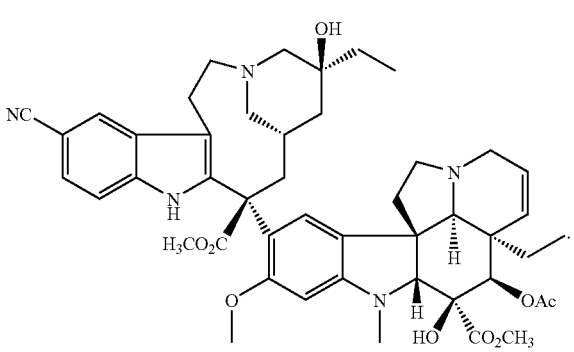

43. The method according to claim 26, wherein the compound has the following chemical formula:

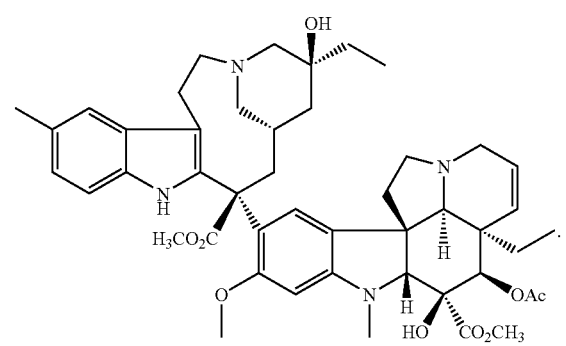

44. The method according to claim 26, wherein the compound has the following chemical formula:

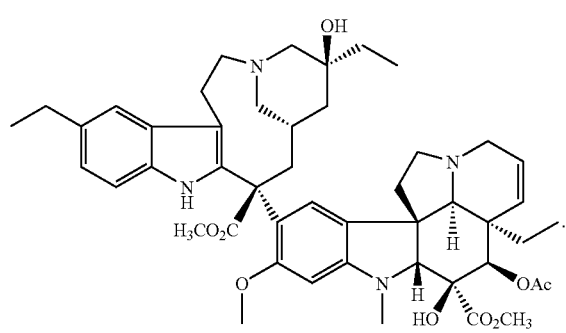

45. The method according to claim 26, wherein the compound has the following chemical formula:

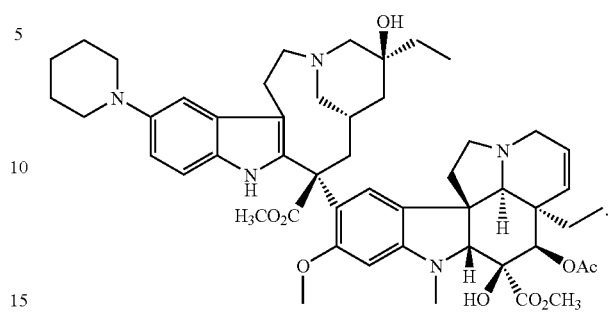

46. A method for treating a condition selected from the group consisting of choricarcinoma, neuroblastoma, acute lung organs leukemia, chronic lung organs leukemia, testicular cancers, non-Hodgkin's lymphoma, acute childhood leukemia, lymphatic leukemia, Wilm's tumor, rhabdosarcoma, reticulum cell sarcoma, melanoma, and squamous cell cancer of the cervix in mammals comprising:
   administering to a mammal a therapeutically effective amount of a compound having the following chemical formula:

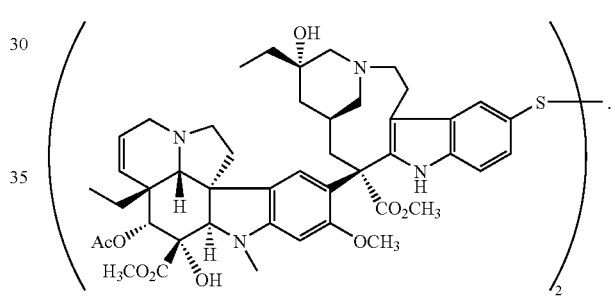

47. A method for treating a condition selected from the group consisting of choricarcinoma, neuroblastoma, acute lung organs leukemia, chronic lung organs leukemia, testicular cancers, non-Hodgkin's lymphoma, acute childhood leukemia, lymphatic leukemia, Wilm's tumor, rhabdosarcoma, reticulum cell sarcoma, melanoma, and squamous cell cancer of the cervix in mammals comprising:
   administering to a mammal a therapeutically effective amount of a compound having the following chemical formula:

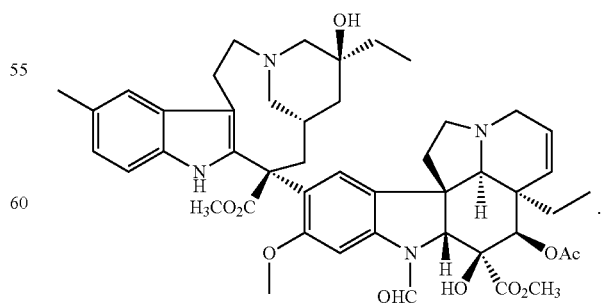

48. A method for treating a condition selected from the group consisting of choricarcinoma, neuroblastoma, acute lung organs leukemia, chronic lung organs leukemia, testicular cancers, non-Hodgkin's lymphoma, acute childhood leukemia, lymphatic leukemia, Wilm's tumor, rhabdosarcoma, reticulum cell sarcoma, melanoma, and squamous cell cancer of the cervix in mammals comprising:

administering to a mammal a therapeutically effective amount of a compound having the following chemical formula:

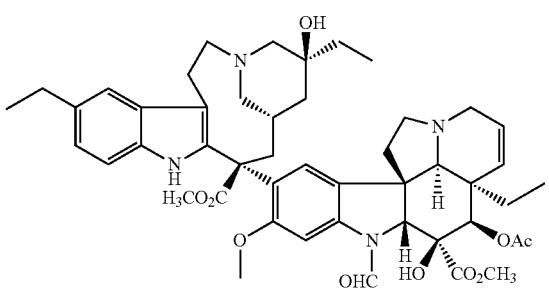

49. A method for treating a condition selected from the group consisting of choricarcinoma, neuroblastoma, acute lung organs leukemia, chronic lung organs leukemia, testicular cancers, non-Hodgkin's lymphoma, acute childhood leukemia, lymphatic leukemia, Wilm's tumor, rhabdosarcoma, reticulum cell sarcoma, melanoma, and squamous cell cancer of the cervix in mammals comprising:

administering to a mammal a therapeutically effective amount of a compound having the following chemical formula:

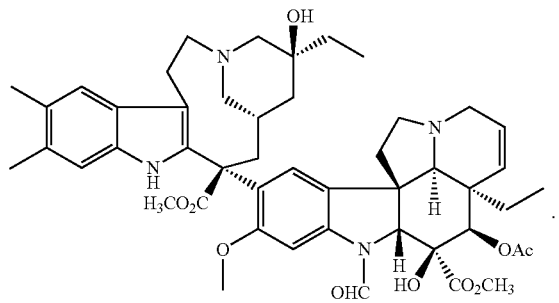

50. A method for treating a condition selected from the group consisting of choricarcinoma, neuroblastoma, acute lung organs leukemia, chronic lung organs leukemia, testicular cancers, non-Hodgkin's lymphoma, acute childhood leukemia, lymphatic leukemia, Wilm's tumor, rhabdosarcoma, reticulum cell sarcoma, melanoma, and squamous cell cancer of the cervix in mammals comprising:

administering to a mammal a therapeutically effective amount of a compound having the following chemical formula:

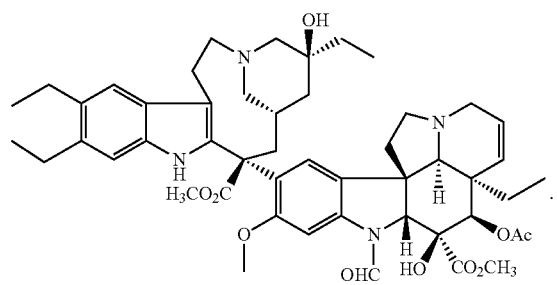

* * * * *